United States Patent
Miller-Moslin et al.

(10) Patent No.: US 8,809,352 B2
(45) Date of Patent: Aug. 19, 2014

(54) SULFONAMIDES AS INHIBITORS OF BCL-2 FAMILY PROTEINS FOR THE TREATMENTS OF CANCER

(75) Inventors: Karen Miller-Moslin, Princeton, NJ (US); Bakary-Barry Toure, Weston, MA (US); Michael Scott Visser, Braintree, MA (US); Naeem Yusuff, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/394,525

(22) PCT Filed: Sep. 8, 2010

(86) PCT No.: PCT/EP2010/063169
§ 371 (c)(1),
(2), (4) Date: Mar. 6, 2012

(87) PCT Pub. No.: WO2011/029842
PCT Pub. Date: Mar. 17, 2011

(65) Prior Publication Data
US 2012/0165298 A1    Jun. 28, 2012

Related U.S. Application Data

(60) Provisional application No. 61/241,251, filed on Sep. 10, 2009.

(51) Int. Cl.
| | |
|---|---|
| *A01N 43/62* | (2006.01) |
| *A61K 31/55* | (2006.01) |
| *A61K 31/497* | (2006.01) |
| *A01N 43/90* | (2006.01) |
| *A61K 31/519* | (2006.01) |
| *A01N 43/64* | (2006.01) |
| *A61K 31/41* | (2006.01) |
| *C07D 471/00* | (2006.01) |
| *C07D 487/00* | (2006.01) |
| *C07D 471/04* | (2006.01) |

(52) U.S. Cl.
CPC .................................. *C07D 471/04* (2013.01)
USPC ................... 514/264.1; 514/221; 514/254.06; 514/265.1; 514/383; 544/279; 544/280; 544/350

(58) Field of Classification Search
None
See application file for complete search history.

(56) References Cited

U.S. PATENT DOCUMENTS
2010/0056517 A1    3/2010  Baell et al.

OTHER PUBLICATIONS

Neidle, Cancer Drug Design and Discovery, Elsevier/Academic Press, 2008, pp. 427-431.*
Parikh et al. "Phase II Study of Obatoclax Mesylate (GX15-070), a Small-Molecule BCL-2 Family Antagonist, for Patients with Myelofibrosis", Clin.Lymph.Myel.Leuk., 2010, vol. 10, No. 4, pp. 285-289.*

* cited by examiner

*Primary Examiner* — James D Anderson
*Assistant Examiner* — Stephanie Springer
(74) *Attorney, Agent, or Firm* — Scott W. Reid

(57) ABSTRACT

The present invention includes novel compound and methods of treating a disease or disorder by antagonizing Bcl-2 family proteins, particularly compounds of formula (I):

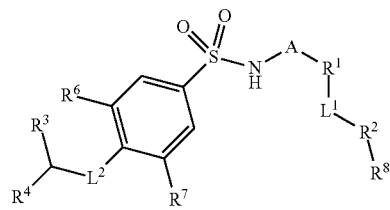

or pharmaceutically acceptable salt thereof, as well as methods of treating a disease, disorder, or syndrome associated with Bcl-2 inhibition, particularly hyperproliferative diseases. The present invention also includes pharmaceutical compositions including compounds of formula I and pharmaceutically acceptable salts thereof.

4 Claims, No Drawings

SULFONAMIDES AS INHIBITORS OF BCL-2 FAMILY PROTEINS FOR THE TREATMENTS OF CANCER

FIELD OF THE INVENTION

The present invention relates to sulfonamide compounds that bind to and inhibit Bcl-2 family proteins, and uses thereof for the treatment of diseases associated with such inhibition. Consequently, the present invention includes sulfonamide compounds, compositions thereof, methods of their use, and methods of their manufacture, where such compounds are generally pharmacologically useful in therapies whose mechanism of action rely on the inhibition of Bcl-2 family proteins, and more particularly in therapies for the treatment of proliferative diseases, including cancer.

BACKGROUND

Bcl-2 family proteins are anti-apoptotic proteins associated with cancer and other diseases. Bcl-2 family proteins under investigation as therapeutic targets include Bcl-2 (BCL2), Bcl-xL (BCL2L1), Bcl-w (BCL2L2), A1 (BCL2A1), and MCL1 (MCL1). Numerous cancers express one or more Bcl-2 family proteins leading to cancer cell survival and resistance to chemotherapeutics. For example, chromosomal translocation of Bcl-2, t(14; 18), is a transforming event in some cancer cells (Raffeld, et al. *Cancer Research* 1987, 47(10):2537-42), and these cancer cells demonstrate dependence on Bcl-2 for survival based on RNAi (FIG. 1), and sensitivity to recently described small molecule inhibitors of Bcl-2 family proteins (Oltersdorf, et al. *Nature* 2005, 435, 677-681; Deng et al. *Cancer Cell* 2007, 12(2), 171-185). This invention is directed to a series of compounds that inhibit Bcl-2 family proteins and promote apoptosis of cancer cells, alone or in combination with other chemotherapeutics.

In addition to B-cell lymphomas, Bcl-2 family antagonists have been shown to be useful for treating cancers that express Bcl-2 family members and/or have deregulated apoptosis such as chronic lymphocytic leukemia, diffuse large B-cell lymphomas, follicular lymphomas, chronic or acute leukemia, chronic myeloid leukemia, lymphoid malignancies of T-cell or B-cell origin, small cell lung cancer, non-small cell lung cancer, melanoma or other skin cancers, multiple myeloma, ovarian cancer, breast cancer, colon cancer, gastrointestinal cancer (gastric, colorectal, and duodenal), prostate cancer, bladder cancer, uterine cancer, cervical cancer, sarcoma of soft tissue origin, pancreatic cancer, kidney cancer, brain tumors, hepatocellular cancer, head and neck cancer, cervical cancer, fibrosarcoma, and other cancers.

SUMMARY

The present invention provides compounds and pharmaceutical formulations thereof that are useful in the treatment of diseases and/or disorders modulated by the inhibition of Bcl-2.

Compounds of formula (I) are provided herein

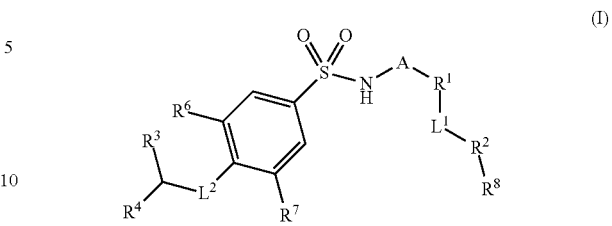

wherein

A is a divalent bicyclic radical comprising a saturated cyclic structure and an unsaturated cyclic structure, wherein said unsaturated cyclic structure is attached to NH, and said saturated cyclic structure is attached to $R^1$, wherein A is unsubstituted or substituted with one or more of halogen, OH, $(C_1\text{-}C_6)$alkyl, halo-substituted$(C_1\text{-}C_6)$alkyl, CN or $NR^{10}R^{11}$;

$R^1$ is a 3- to 8-membered cycloheteroalkyl group, a $(C_3\text{-}C_8)$cycloalkyl group, or a $(C_6\text{-}C_{14})$aryl group which is unsubstituted or substituted with $(C_1\text{-}C_6)$alkyl, halogen, $OR^{57}$, $NR^{58}R^{59}$, or deuterium;

$L^1$ is $(C_1\text{-}C_3)$alkylene, $(C_1\text{-}C_4)$alkenylene, —C(O)—, —C(O)O—, —C(O)N—, —$(C_1\text{-}C_3)$alkylene-C(O)—, —$(C_1\text{-}C_3)$alkylene-C(O)O—, or a bond, wherein $L^1$ is unsubstituted or substituted by one or more $(C_1\text{-}C_4)$alkyl, halo-substituted $(C_1\text{-}C_4)$haloalkyl, or $(C_3\text{-}C_8)$cycloalkyl;

$L^2$ is $(C_1\text{-}C_3)$alkylene, $NR^9$, —O—, or —S—;

$R^2$ is $(C_6\text{-}C_{14})$aryl group, 5- to 14-membered heteroaryl, 3- to 8-membered cycloheteroalkyl group, or $(C_3\text{-}C_{14})$cycloalkyl group, each of which is unsubstituted or substituted with one or more of halogen, OH, $(C_1\text{-}C_6)$alkyl, halo-substituted$(C_1\text{-}C_6)$alkyl, or CN;

$R^8$ is $(C_1\text{-}C_6)$alkyl, $(C_6\text{-}C_{14})$aryl, $(C_3\text{-}C_{14})$cycloalkyl, halogen, or 3- to 14-membered cycloheteroalkyl, in which any the aforementioned hydrocarbon groups (e.g., $(C_1\text{-}C_6)$alkyl, $(C_6\text{-}C_{14})$aryl, and $(C_3\text{-}C_{14})$cycloalkyl) is optionally substituted with one or more substituents each independently selected from halogen, $(C_1\text{-}C_6)$alkyl, halo-substituted $(C_1\text{-}C_6)$alkyl, OH, or $NR^{44}R^{45}$;

$R^3$ and $R^4$ are each independently H, $(C_1\text{-}C_6)$alkyl, —$(C_1\text{-}C_6)$alkylene-$(C_6\text{-}C_{14})$aryl, —$(C_1\text{-}C_6)$alkylene-(5-to 14-membered heteroaryl), —$(C_1\text{-}C_6)$alkylene-$CONR^{16}R^{17}$, —$(C_1\text{-}C_6)$alkylene-O—$R^{15}$, —$(C_1\text{-}C_6)$alkylene-$NR^{13}R^{14}$, —$(C_1\text{-}C_3)$alkylene-(3- to 14-membered cycloheteroalkyl), —$(C_1\text{-}C_3)$alkylene-S—$(C_6\text{-}C_{14})$aryl group, —$(C_1\text{-}C_6)$alkylene-$COR^{18}$, —$(C_1\text{-}C_6)$alkylene-C(O)O—$R^{19}$, —$(C_1\text{-}C_6)$alkylene-O—C(O)—$R^{20}$, —$(C_1\text{-}C_3)$alkylene-S—$R^{21}$, —$(C_1\text{-}C_3)$alkylene-$SOR^{22}$, or —$(C_1\text{-}C_3)$alkylene-$SO_2R^{23}$;

$R^6$ and $R^7$ are each independently H, $NO_2$, —$SO_2CF_3$, —$SO_2(C_1\text{-}C_6)$alkyl, halo-substituted $(C_1\text{-}C_6)$alkyl, halogen, $(C_3\text{-}C_{14})$cycloalkyl, or CN;

$R^9$ is H, $(C_1\text{-}C_6)$alkyl, —$(C_1\text{-}C_6)$alkylene-$(C_6\text{-}C_{14})$aryl, —$(C_1\text{-}C_3)$alkylene-(5- to 14-membered heteroaryl), —$(C_1\text{-}C_3)$alkylene-$CONR^{46}R^{47}$, —$(C_1\text{-}C_3)$alkylene-O—$R^{48}$, —$(C_1\text{-}C_3)$alkyene-$NR^{49}R^{50}$, —$(C_1\text{-}C_3)$alkylene-(3- to 14-membered cycloheteroalkyl), —$(C_1\text{-}C_3)$alkyene-S—$(C_6\text{-}C_{14})$aryl group, —$(C_1\text{-}C_3)$alkylene-$C(O)R^{51}$, —$(C_1\text{-}C_3)$alkylene-C(O)O—$R^{52}$, —$(C_1\text{-}C_3)$alkylene-O—C(O)—$R^{53}$, —$(C_1\text{-}C_3)$alkylene-S—$R^{54}$, —$(C_1\text{-}C_3)$alkylene-$SOR^{55}$, —$(C_1\text{-}C_3)$alkylene-$SO_2R^{56}$, —C(O)—$(C_1\text{-}C_6)$alkyl, —C(O)—$(C_1\text{-}C_3)$alkylene-$(C_6\text{-}C_{14})$aryl, —C(O)—$(C_1\text{-}C_6)$alkylene-(5- to 14-membered heteroaryl), —C(O)—$(C_1\text{-}C_3)$alkylene-(3- to 14-membered cycloheteroalkyl), —C(O)—$(C_1\text{-}C_3)$alkylene-$C(O)NR^{46}R^{47}$, —C(O)—$(C_1\text{-}C_3)$alkylene-O—$R^{48}$, —C(O)—$(C_1\text{-}C_3)$alkylene-$NR^{49}R^{50}$, —C(O)—$(C_1\text{-}C_3)$alkylene-S—$(C_6\text{-}C_{14})$aryl, —C(O)—$(C_1\text{-}C_3)$alkylene-C (O)R$^{51}$, —C(O)—(C$_1$-C$_3$)alkylene-C(O)O—R$^{52}$, —C(O)—(C$_1$-C$_3$)alkylene-O—C(O)—R$^{53}$, —C(O)—(C$_1$-C$_3$)alkylene-S—R$^{54}$, —C(O)—(C$_1$-C$_3$)alkylene-SOR$^{55}$, or C(O)—(C$_1$-C$_3$)alkylene-SO$_2$R$^{56}$;

R$^{10}$, R$^{11}$, R$^{13}$, R$^{14}$, R$^{16}$, R$^{17}$R$^{44}$, R$^{45}$, R$^{46}$, R$^{47}$, R$^{49}$, R$^{50}$, R$^{57}$, R$^{58}$, and R$^{59}$ are each independently H, (C$_1$-C$_6$)alkyl, (C$_2$-C$_6$)alkenyl, (C$_2$-C$_6$)alkynyl, OH, —C(O)—(C$_1$-C$_6$)alkyl, (C$_1$-C$_6$)alkoxy, halogen, (C$_3$-C$_{14}$)cycloalkyl, (C$_6$-C$_{14}$)aryl, 4- to 14-membered cycloheteroalkyl, or 5- to 14-membered heteroaryl, wherein each of the aforementioned hydrocarbon groups (e.g., (C$_1$-C$_6$)alkyl, (C$_2$-C$_6$)alkenyl, (C$_2$-C$_6$)alkynyl, (C$_3$-C$_{14}$)cycloalkyl), (C$_6$-C$_{14}$)aryl, and the (C$_1$-C$_6$)alkyl moieties of —C(O)—(C$_1$-C$_6$)alkyl, and (C$_1$-C$_6$)alkoxy) is optionally substituted by one or more halogen, hydroxyl, (C$_1$-C$_6$)alkoxy, amino, (C$_1$-C$_6$)alkylamino, d((C$_1$-C$_6$)alkyl)amino or cyano;

or R$^{13}$ and R$^{14}$ together with the N to which they are attached form a 4- to 8-membered cycloheteroalkyl, or a 5- to 14-membered heteroaryl, each of which is substituted or unsubstituted;

or R$^{16}$ and R$^{17}$ together with the N to which they are attached form a 4- to 8-membered cycloheteroalkyl, or a 5-14 membered heteroaryl, each of which is substituted or unsubstituted;

or R$^{58}$ and R$^{59}$ together with the N to which they are attached form a 4- to 8-membered cycloheteroalkyl, or a 5-14 membered heteroaryl, each of which is substituted or unsubstituted;

or R$^{44}$ and R$^{45}$ together with the N to which they are attached form a 4- to 8-membered cycloheteroalkyl, or a 5- to 14-membered heteroaryl, each of which is substituted or unsubstituted;

or R$^{46}$ and R$^{47}$ together with the N to which they are attached form a 4- to 8-membered cycloheteroalkyl, or a 5- to 14-membered heteroaryl, each of which is substituted or unsubstituted;

or R$^{49}$ and R$^{50}$ together with the N to which they are attached form a 4- to 8-membered cycloheteroalkyl, or a 5- to 14-membered heteroaryl, each of which is substituted or unsubstituted;

R$^{15}$, R$^{18}$, R$^{19}$, R$^{20}$, R$^{22}$, R$^{23}$, R$^{48}$, R$^{51}$, R$^{52}$, R$^{53}$, R$^{55}$, and R$^{56}$ are each independently —(C$_1$-C$_6$)alkylene-(C$_6$-C$_{14}$)aryl, or —(C$_1$-C$_6$)alkylene-(5- to 14-membered heteroaryl), each of which is unsubstituted or substituted with one or more of halogen, OH, (C$_1$-C$_6$)alkyl, halo-substituted (C$_1$-C$_6$)alkyl, or CN; and R$^{21}$ and R$^{54}$ are each independently (C$_6$-C$_{14}$)aryl, 5- to 14-membered heteroaryl, —(C$_1$-C$_6$)alkylene-(C$_6$-C$_{14}$)aryl, or —(C$_1$-C$_6$)alkylene-(5- to 14-membered heteroaryl), each of which is unsubstituted or substituted with one or more of halogen, OH, (C$_1$-C$_6$)alkyl, halo-substituted (C$_1$-C$_6$)alkyl, or CN;

or a pharmaceutically acceptable salt thereof.

In one embodiment, the present invention includes compounds of formula (I) where A is a divalent bicyclic radical comprising a saturated cyclic structure and an unsaturated cyclic structure, wherein said unsaturated cyclic structure is attached to NH, and said saturated cyclic structure is attached to R$^1$, wherein A is unsubstituted or substituted with one or more of halogen, OH, (C$_1$-C$_6$)alkyl (e.g., methyl, ethyl, propyl, or butyl), halo-substituted (C$_1$-C$_6$)alkyl (e.g., CF$_3$, CH$_2$CF$_3$), or CN.

In a preferred embodiment, A is

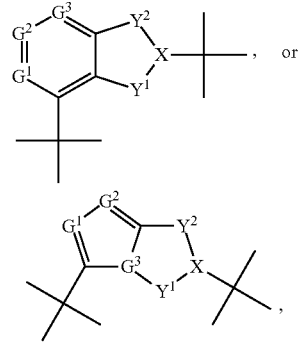

where
G$^1$, G$^2$, and G$^3$ are independently CR$^{29}$ or N; Y$^1$ and Y$^2$ are each independently —CR$^{30}$R$^{31}$—, —CR$^{32}$R$^{33}$—CR$^{34}$R$^{35}$—, —NR$^{36}$—, —CR$^{37}$R$^{38}$—NR$^{39}$—, —O—, —S—, —CR$^{40}$R$^{41}$—O—, or —CR$^{42}$R$^{43}$—S—;

X is CH or N; and

R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, and R$^{43}$ are each independently H, (C$_1$-C$_6$)alkyl, halogen, halo-substituted (C$_1$-C$_6$)alkyl, or (C$_3$-C$_{14}$)cycloalkyl. Preferably, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, and R$^{43}$ are each independently H, methyl, ethyl, propyl, F, Cl, CF$_3$, cyclopropyl, cyclobutyl, cyclopentyl, or cyclohexyl; or a pharmaceutically acceptable salt thereof.

In another embodiment, the present invention includes compounds of formula (I) where A is:

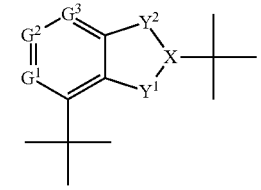

and at least one of G$^1$, G$^2$, and G$^3$ is N;

Y$^1$ and Y$^2$ are independently —CR$^{30}$R$^{31}$—, —CR$^{32}$R$^{33}$—CR$^{34}$R$^{35}$—; and X is N, and R$^{30}$, R$^{31}$, R$^{32}$, R$^{33}$, R$^{34}$, and R$^{35}$ are each independently H, methyl, ethyl, propyl, Cl, F, or CF$_3$; or a pharmaceutically acceptable salt thereof.

In a preferred embodiment, G$^1$, G$^2$, and G$^3$ are each independently CH, C—CH$_3$, C—CN, C—NR$^{10}$R$^{11}$, C—CF$_3$, C—F, C—Cl, or N.

In another preferred embodiment, G$^1$ and G$^3$ are N.

In another embodiment, Y$^1$ and Y$^2$ are each independently —CH$_2$—, —CH$_2$—CH$_2$—, —NH—, —NCH$_3$—, —CH$_2$NH—, —O—, —S—, —CH$_2$—O—, or —CH$_2$—S—.

In yet another preferred embodiment, Y$^1$ is —CH$_2$CH$_2$— and Y$^2$ is —CH$_2$—. In another embodiment, X is CH. In another preferred embodiment, X is N.

In another embodiment, X is N, and N is attached to a carbon atom of a heteroaryl or cycloheteroalkyl of R$^1$, and L$^1$ is a bond.

In another embodiment where X is CH, X is attached to a heteroatom of a heteroaryl or cycloheteroalkyl of R$^1$, and L$^1$ is a bond.

In another embodiment, the present invention includes compounds of formula (I) where two of $G^1$, $G^2$, and $G^3$ are N, and the remaining G is $CR^{29}$;
$Y^1$ is $-CR^{32}R^{33}-CR^{34}R^{35}-$;
$Y^2$ is $-CR^{30}R^{31}-$;
$R^{29}$ is Fl, methyl, Cl, F, $CF_3$;
$R^{32}$, $R^{33}$, $R^{34}$, and $R^{35}$ are H;
$R^{30}$ and $R^{31}$ are H; and X is N.

In another embodiment, the present invention includes compounds of formula (I) where $G^1$ and $G^3$ are N, and $G^2$ is $CR^{29}$; $Y^1$ is $-CR^{32}R^{33}-CR^{34}R^{35}-$; $Y^2$ is $-CR^{30}R^{31}-$; $R^{29}$ is H, methyl, Cl, F, or $CF_3$; $R^{32}$, $R^{33}$, $R^{34}$, and $R^{35}$ are H; and X is N.

In yet another embodiment of the present invention, compounds of formula (I) are included wherein A is:

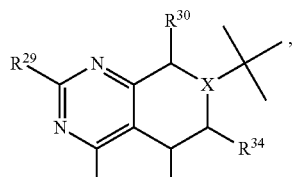

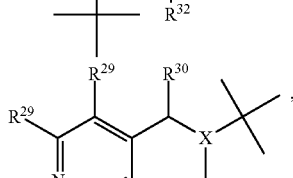

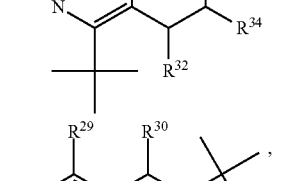

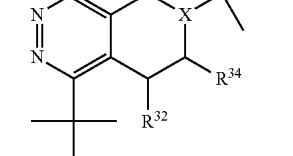

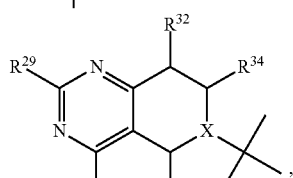

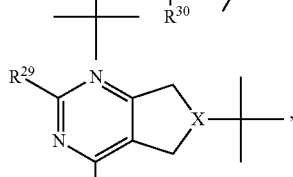

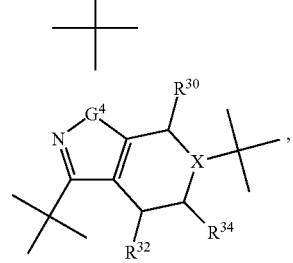

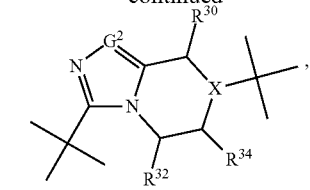

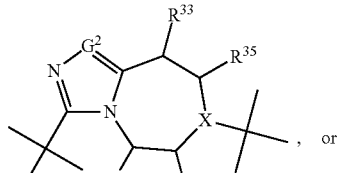

, or

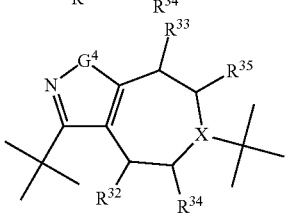

where X is CH or N; $G^2$ is $CR^{29}$, or N; $G^4$ is O, S, or $NR^{60}$; and $R^{29}$, $R^{30}$, $R^{31}$, $R^{32}$, $R^{33}$, $R^{34}$, $R^{35}$, and $R^{60}$ are each independently H, methyl, ethyl, propyl, Cl, F, or $CF_3$; or a pharmaceutically acceptable salt thereof.

In another embodiment, A is

, or

each of which is unsubstituted or substituted with one or more substituents each independently selected from halogen, OH, $(C_1-C_6)$alkyl (e.g., methyl, ethyl, propyl, or butyl), halo-substituted $(C_1-C_6)$alkyl (e.g., $CF_3$), CN, or $NR^{10}R^{11}$.

In an embodiment, $R^1$ is 3-to 8-membered cycloheteroalkyl (e.g., piperidinyl, piperazinyl, morpholinyl, or tetrahydrofuranyl), $(C_3-C_8)$cycloalkyl (e.g., cyclopropyl, cyclobutyl, cyclopentyl, or cyclohexyl), or $(C_6-C_{14})$aryl (e.g., phenyl or naphthyl), each of which is unsubstituted or substituted with one or more substituents each independently selected from $(C_1-C_6)$alkyl (e.g., methyl, ethyl, propyl, butyl, or pentyl), halogen, $NR^{58}R^{59}$ (e.g., $NH_2$, $NHCH_3$, or $NCH_3CH_3$), deuterium, or $OR^{57}$, where $R^{57}$ is $(C_1-C_6)$alkyl or H.

In yet another embodiment, the present invention includes compounds of formula (I) wherein $R^1$ is piperidinyl, piperazinyl, morpholinyl, tetrahydrofuranyl, cyclopropyl, cyclobutyl, cyclopentyl, cyclohexyl, or phenyl which is unsubstituted or substituted with methyl, ethyl, propyl, Cl, F, Br, I, or methoxy. In another embodiment, $R^1$ is piperidinyl, piperazinyl, morpholinyl, cyclopentyl, or cyclohexyl, each of which is unsubstituted or substituted with methyl, methoxy, Cl, or F. In another embodiment, $R^1$ is piperidinyl, piperazinyl, or cyclohexyl, each of which is unsubstituted or substituted with methyl, ethyl, F, Cl, or Br. In another embodiment, $R^1$ is piperidinyl which is unsubstituted or substituted with methyl or F.

In another embodiment, $L^1$ is $(C_1-C_3)$alkylene (e.g., methylene, ethylene or propylene), $(C_1-C_4)$alkenylene (e.g., =C—, —C=C—, —C=C—C—, or —C—C=C—; —C(O)—, —C(O)O—, —C(O)N—, —$((C_1-C_3)$alkyl)-C(O)— (e.g., —CH$_2$C(O)—, —CH$_2$CH$_2$C(O)— or CH$_2$—CH$_2$—CH$_2$—C(O)—), $((C_1-C_3)$alkyl)-C(O)O— (e.g., —CH$_2$C(O)O—, —CH$_2$CH$_2$C(O)O— or CH$_2$—CH$_2$—CH$_2$—C(O)O—), or a bond, wherein $L^1$ is unsubstituted or substituted by one or more substituents each independently selected from $(C_1-C_4)$alkyl (e.g., methyl, ethyl, propyl, or butyl), halo-substituted $(C_1-C_4)$alkyl (e.g., CF$_3$ or CH$_2$CF$_3$) or $(C_3-C_8)$cycloalkyl (e.g., cyclopropyl, cyclobutyl, cyclopentyl, or cyclohexyl).

In another embodiment, $L^1$ is methylene, ethylene, propylene, =C—, —C=C—, —C=C—C—, —C(O)—, —C(O)O—, C(O)N—, —CH$_2$C(O)—, —CH$_2$C(O)O—, or a bond, wherein $L^1$ is unsubstituted or substituted by one or more substituents each independently selected from methyl, ethyl, or CF$_3$. In another embodiment, $L^1$ is methylene ethylene, or a bond. In another embodiment, $L^1$ is methylene.

In another embodiment, $L^2$ is $(C_1-C_3)$alkylene (e.g., methylene, ethylene, or propylene), NR$^9$, —O—, or —S—, where R$^9$ is H, $(C_1-C_6)$alkyl (e.g., methyl, ethyl, propyl, or butyl), —$(C_1-C_3)$alkylene-$(C_6-C_{14})$aryl (e.g., —CH$_2$-phenyl, —CH$_2$CH$_2$-phenyl, or CH$_2$CH$_2$CH$_2$-phenyl), —$(C_1-C_3)$alkylene-(5- to 14-membered heteroaryl) (e.g., —CH$_2$-pyridinyl, —CH$_2$CH$_2$-pyridinyl, —CH$_2$-pyrimidinyl, or —CH$_2$CH$_2$-pyrimidinyl), —$(C_1-C_3)$alkylene-CONR$^{46}$R$^{47}$ (e.g., —CH$_2$C(O)NCH$_3$CH$_3$, —CH$_2$C(O)NHCH$_3$, —CH$_2$CH$_2$C(O)NCH$_3$CH$_3$, or —CH$_2$CH$_2$C(O)NHCH$_3$), —$(C_1-C_3)$alkylene-O—R$^{48}$ (e.g., —CH$_2$—O—CH$_3$, —CH$_2$—O—CH$_2$CH$_3$, —CH$_2$CH$_2$—O—CH$_3$, or —CH$_2$CH$_2$—O—CH$_2$CH$_3$), —$(C_1-C_3)$alkylene-NR$^{49}$R$^{50}$—$(C_1-C_3)$alkylene-(3- to 14-membered cycloheteroalkyl) (e.g., —CH$_2$-piperidinyl, —CH$_2$CH$_2$-piperidinyl, or —CH$_2$CH$_2$CH$_2$-piperidinyl), —$(C_1-C_3)$alkylene-S—$(C_6-C_{14})$aryl (e.g., —CH$_2$—S-phenyl, —CH$_2$CH$_2$—S-phenyl, or —CH$_2$CH$_2$CH$_2$—S-phenyl), $(C_1-C_3)$alkylene-C(O)R$^{51}$ (e.g., —CH$_2$C(O)CH$_3$, —CH$_2$C(O)CH$_2$CH$_3$, —CH$_2$CH$_2$C(O)CH$_3$, or —CH$_2$CH$_2$C(O)CH$_2$CH$_3$), —$(C_1-C_3)$alkylene-C(O)O—R$^{52}$ (e.g., —CH$_2$C(O)OCH$_3$, —CH$_2$C(O)OCH$_2$CH$_3$, —CH$_2$CH$_2$C(O)OCH$_3$, or —CH$_2$CH$_2$C(O)OCH$_2$CH$_3$), —$(C_1-C_3)$alkylene-O—C(O)—R$^{53}$ (e.g., —CH$_2$—O—C(O)CH$_3$, —CH$_2$—O—C(O)CH$_2$CH$_3$, —CH$_2$CH$_2$—O—C(O)CH$_3$, or —CH$_2$CH$_2$—O—C(O)CH$_2$CH$_3$), —$(C_1-C_3)$alkylene-S—R$^{54}$ (e.g., —CH$_2$—S—CH$_3$, —CH$_2$—S—CH$_2$CH$_3$, —CH$_2$CH$_2$—S—CH$_3$, or —CH$_2$CH$_2$—S—CH$_2$CH$_3$), —$(C_1-C_3)$alkylene-SOR$^{55}$ (e.g., —CH$_2$S(O)CH$_3$, —CH$_2$S(O)CH$_2$CH$_3$, —CH$_2$CH$_2$S(O)CH$_3$, or —CH$_2$CH$_2$S(O)CH$_2$CH$_3$), —$(C_1-C_3)$alkylene-SO$_2$R$^{56}$ (e.g., —CH$_2$S(O)OCH$_3$, —CH$_2$S(O)OCH$_2$CH$_3$, —CH$_2$CH$_2$S(O)OCH$_3$, or —CH$_2$CH$_2$S(O)OCH$_2$CH$_3$), —C(O)—$(C_1-C_6)$alkyl (e.g., —C(O)CH$_3$ or —C(O)CH$_2$CH$_3$), —C(O)—$(C_1-C_3)$alkylene-$(C_6-C_{14})$aryl (e.g., —C(O)CH$_2$-phenyl or —C(O)CH$_2$CH$_2$-phenyl), —C(O)—$(C_1-C_3)$alkylene-(5-to 14-membered heteroaryl) (e.g., —C(O)CH$_2$-pyridinyl, —C(O)CH$_2$CH$_2$-pyridinyl, —C(O)CH$_2$-pyrimidinyl, or —C(O)CH$_2$CH$_2$-pyrimidinyl), or —C(O)—$(C_1-C_3)$alkylene-(3- to 14-membered cycloheteroalkyl) (e.g., —C(O)CH$_2$-piperidinyl, —C(O)CH$_2$CH$_2$-piperidinyl, or —C(O)CH$_2$CH$_2$CH$_2$-piperidinyl).

In another embodiment, $L^2$ is —CH$_2$- or NR$^9$ where R$^9$ is H, methyl, or ethyl. In another embodiment, $L^2$ is —CH$_2$— or —NH—. In another embodiment, $L^2$ in —NH—.

In yet another embodiment, the present invention includes compounds of formula (I) where $L^1$ is —CH$_2$—, —CH$_2$CH$_2$—, or a bond; and $L^2$ is —CH$_2$— or NH.

In an embodiment, $R^2$ is a $(C_6-C_{14})$aryl (e.g., phenyl or naphthyl), 5- to 14-membered heteroaryl (e.g., pyridinyl, pyrimidinyl, or pyridazinyl), 3- to 8-membered cycloheteroalkyl (e.g., piperidinyl, piperazinyl, morpholinyl, or tetrahydrofuranyl) or $(C_3-C_{14})$cycloalkyl (e.g., cyclopropyl, cyclobutyl, cyclopentyl, cyclohexyl, or a partially saturated cyclohexyl (cyclohexenyl or cyclohexadienyl)) each of which is unsubstituted or substituted with one or more of halogen, OH, —$(C_1-C_6)$alkyl, halo-substituted —$(C_1-C_3)$alkyl (preferably, CF$_3$); or CN.

In another embodiment, the present invention includes compounds of formula (I) where $R^2$ is phenyl, naphthyl, pyridinyl, pyrimidinyl, or pyridazinyl; each of which is unsubstituted or substituted with one or more substituents each independently selected from methyl, dimethyl, ethyl, propyl, butyl, pentyl, hexyl, phenyl, cyclopropyl, cyclobutyl, cyclopentyl, CF$_3$, or CH$_2$Cl. In another embodiment, $R^2$ is phenyl, cyclohexyl, or a partially saturated cyclohexyl, where $R^2$ is unsubstituted or substituted with one or more substituents selected from methyl, dimethyl, OH, F, Cl, or Br. In another embodiment, $R^2$ is phenyl.

In another embodiment, $R^3$ and $R^4$ are each independently H, $(C_1-C_6)$alkyl, —$(C_1-C_6)$alkylene-$(C_6-C_{14})$aryl (e.g., —CH$_2$-phenyl, —CH$_2$CH$_2$-phenyl, —CH$_2$CH$_2$CH$_2$-phenyl, —CH$_2$CH$_2$CH$_2$CH$_2$-phenyl, or —CH$_2$CH$_2$CH$_2$CH$_2$CH$_2$-phenyl), —$(C_1-C_6)$alkylene-(5- to 14-membered heteroaryl) (e.g., —CH$_2$CH$_2$CH$_2$CH$_2$-pyridinyl or —CH$_2$CH$_2$CH$_2$CH$_2$-pyrimidinyl), —$(C_1-C_6)$alkylene-C(O)NR$^{16}$R$^{17}$ (e.g., —CH$_2$CH$_2$CH$_2$CH$_2$C(O)NCH$_3$CH$_3$, —CH$_2$CH$_2$CH$_2$CH$_2$C(O)NHCH$_3$, or —CH$_2$CH$_2$CH$_2$CH$_2$C(O)NH$_2$), —$(C_1-C_6)$alkylene-O—R$^{15}$ (e.g., -butyl-O—CH$_3$ or -butyl-O—CH$_2$CH$_3$), —$(C_1-C_6)$alkylene-NR$^{13}$R$^{14}$ (e.g., -butyl-N(CH$_3$)(CH$_3$), -butyl-NHCH$_3$, -butyl-NH$_2$, -butyl-NH-phenyl, or -butyl-N(CH$_3$)(CH$_3$)), —$(C_1-C_6)$alkylene-(3-to 14-membered cycloheteroalkyl) (e.g., -butyl-piperidinyl), —$(C_1-C_3)$alkylene-S—$(C_6-C_{14})$aryl group, —$(C_1-C_6)$alkylene-COR$^{18}$, —$(C_1-C_6)$alkylene-C(O)O—R$^{19}$, —$(C_1-C_6)$alkylene-O—C(O)—R$^{20}$, $(C_1-C_3)$alkylene-S—R$^{21}$, —$(C_1-C_3)$alkylene-SOR$^{22}$, or —$(C_1-C_3)$alkylene-SO$_2$R$^{23}$.

In a preferred embodiment, $R^3$ and $R^4$ are each independently H, $(C_1-C_6)$alkyl (preferably, methyl, ethyl, propyl, or butyl), —$(C_1-C_3)$alkylene-$(C_6-C_{14})$aryl (preferably, —CH$_2$-phenyl, —CH$_2$CH$_2$-phenyl, or —CH$_2$CH$_2$CH$_2$-phenyl), —$(C_1-C_3)$alkylene-(5- to 14-membered heteroaryl) (preferably, —CH$_2$-pyridinyl, —CH$_2$CH$_2$-pyridinyl, —CH$_2$-pyrimidinyl, or —CH$_2$CH$_2$-pyrimidinyl), —$(C_1-C_3)$alkylene-CONR$^{16}$R$^{17}$ (preferably, —CH$_2$C(O)NCH$_3$CH$_3$, —CH$_2$C(O)NHCH$_3$, —CH$_2$CH$_2$C(O)NCH$_3$CH$_3$, or —CH$_2$CH$_2$C(O)NHCH$_3$), —$(C_1-C_3)$—O—R$^{15}$ (preferably, —CH$_2$—O—CH$_3$, —CH$_2$—O—CH$_2$CH$_3$, —CH$_2$CH$_2$—O—CH$_3$, or —CH$_2$CH$_2$—O—CH$_2$CH$_3$), —$(C_1-C_3)$alkylene-NR$^{13}$R$^{14}$ (preferably, —CH$_2$—N(CH$_3$)(CH$_3$), —CH$_2$—NHCH$_3$, —CH$_2$—NH$_2$, —CH$_2$—NH-phenyl, —CH$_2$—CH$_2$—N(CH$_3$)(CH$_3$), —CH$_2$CH$_2$—NHCH$_3$, —CH$_2$CH$_2$—NH$_2$, or —CH$_2$CH$_2$—NH-phenyl), —$(C_1-C_3)$alkylene-(3- to 14-membered cycloheteroalkyl (preferably, —CH$_2$-piperidinyl, $CH_2CH_2$-piperidinyl, or —$CH_2CH_2CH_2$-piperidinyl), —$(C_1$-$C_3)$alkylene-S—$(C_6$-$C_{14})$aryl (preferably, —$CH_2$—S-phenyl, —$CH_2CH_2$—S-phenyl, or —$CH_2CH_2CH_2$—S-phenyl), —$(C_1$-$C_3)$alkylene-$COR^{18}$ (preferably, —$CH_2C(O)$$CH_3$, —$CH_2C(O)CH_2CH_3$, —$CH_2CH_2C(O)CH_3$, or —$CH_2CH_2C(O)CH_2CH_3$), —$(C_1$-$C_3)$alkylene-$C(O)O$—$R^{19}$ (preferably, —$CH_2C(O)OCH_3$, —$CH_2C(O)OCH_2CH_3$, —$CH_2CH_2C(O)OCH_3$, or —$CH_2CH_2C(O)OCH_2CH_3$), —$(C_1$-$C_3)$alkyl-O—C(O)—$R^{20}$ (preferably, —$CH_2$—O—C(O)$CH_3$, —$CH_2$—O—$C(O)CH_2CH_3$, —$CH_2CH_2$—O—C(O)$CH_3$, or —$CH_2CH_2$—O—$C(O)CH_2CH_3$), —$(C_1$-$C_3)$alkylene-S—$R^{21}$ (preferably, —$CH_2$—S—$CH_3$, —$CH_2$—S—$CH_2CH_3$, —$CH_2CH_2$—S—$CH_3$, or —$CH_2CH_2$—S—$CH_2CH_3$), —$(C_1$-$C_3)$alkylene-$S(O)R^{22}$ (preferably, —$CH_2S(O)CH_3$, —$CH_2S(O)CH_2CH_3$, —$CH_2CH_2S(O)CH_3$, or —$CH_2CH_2S(O)CH_2CH_3$), or —$(C_1$-$C_3)$alkylene-$SO_2R^{23}$ (preferably, —$CH_2S(O)OCH_3$, —$CH_2S(O)OCH_2CH_3$, —$CH_2CH_2S(O)OCH_3$, or —$CH_2CH_2S(O)OCH_2CH_3$).

In another embodiment, $R^3$ and $R^4$ are independently $(C_1$-$C_6)$alkyl, $(C_1$-$C_3)$alkyl-$(C_6$-$C_{14})$aryl, —$(C_1$-$C_3)$alkylene-(5- to 14-membered) heteroaryl, —$(C_1$-$C_3)$alkylene-$C(O)$$NR^{16}R^{17}$, —$(C_1$-$C_3)$alkylene-O—$R^{15}$, —$(C_1$-$C_3)$alkylene-$NR^{13}R^{14}$, —$(C_1$-$C_3)$alkyl-(3- to 14-membered cycloheteroalkyl, or —$(C_1$-$C_3)$alkyl-S—$(C_5$-$C_{14})$aryl.

In an embodiment, $R^3$ and $R^4$ are each independently —$CH_2$-phenyl, —$CH_2CH_2$-phenyl, —$CH_2CH_2CH_2$-phenyl, —$CH_2$-pyridinyl, —$CH_2CH_2$-pyridinyl, —$CH_2$-pyrimidinyl, —$CH_2CH_2$-pyrimidinyl, —$CH_2C(O)NCH_3CH_3$, —$CH_2C(O)NHCH_3$, —$CH_2CH_2C(O)NCH_3CH_3$, —$CH_2$—O—$CH_3$, —$CH_2$—O—$CH_2CH_3$, —$CH_2$—S-phenyl, —$CH_2CH_2$—S-phenyl, —$CH_2CH_2CH_2$—S-phenyl; —$CH_2C(O)CH_3$, —$CH_2C(O)CH_2CH_3$, —$CH_2CH_2C(O)$$CH_3$, —$CH_2$—S—$CH_3$, —$CH_2$—S—$CH_2CH_3$, —$CH_2$—N$(CH_3)(CH_3)$, —$CH_2$—$NHCH_3$, —$CH_2$—$NH_2$, $CH_2$—NH-phenyl, —$CH_2$—$CH_2$—$N(CH_3)(CH_3)$, —$CH_2CH_2$—$NHCH_3$, —$CH_2CH_2$—$NH_2$, or —$CH_2CH_2$—NH-phenyl.

In yet another embodiment $R^3$ is —$CH_2$-phenyl, —$CH_2CH_2$-phenyl, —$CH_2CH_2CH_2$-phenyl, —$CH_2$-pyridinyl, —$CH_2CH_2$-pyridinyl, —$CH_2$-pyrimidinyl, —$CH_2CH_2$-pyrimidinyl, —$CH_2C(O)NCH_3CH_3$, —$CH_2C(O)NHCH_3$, —$CH_2CH_2C(O)NCH_3CH_3$, —$CH_2$—O—$CH_3$, —$CH_2$—O—$CH_2CH_3$, —$CH_2$—S-phenyl, —$CH_2CH_2$—S-phenyl, —$CH_2CH_2CH_2$—S-phenyl; and $R^4$ is —$CH_2C(O)CH_3$, —$CH_2C(O)CH_2CH_3$, —$CH_2CH_2C(O)CH_3$, —$CH_2$—S—$CH_3$, —$CH_2$—S—$CH_2CH_3$, —$CH_2$—$N(CH_3)(CH_3)$, —$CH_2$—$NHCH_3$, —$CH_2$—$NH_2$, $CH_2$—NH-phenyl, —$CH_2$—$CH_2$—$N(CH_3)(CH_3)$, —$CH_2CH_2$—$NHCH_3$, —$CH_2CH_2$—$NH_2$, or —$CH_2CH_2$—NH-phenyl. In another embodiment $R^3$ is —$CH_2$—S-phenyl, or —$CH_2CH_2$—S-phenyl. In another embodiment $R^4$ is —$CH_2$—$N(CH_3)(CH_3)$, —$CH_2$—$NHCH_3$, —$CH_2$—$NH_2$, —$CH_2$—NH-phenyl, or —$CH_2$—$CH_2$—$N(CH_3)(CH_3)$.

In an embodiment $R^8$ is $(C_1$-$C_6)$alkyl (preferably, methyl, ethyl, propyl, butyl, pentyl, or hexyl), $(C_6$-$C_{14})$ aryl (preferably, naphthyl or phenyl), $(C_3$-$C_{14})$cycloalkyl (preferably, cyclopropyl, cyclobutyl, cyclopentyl, or cyclohexyl), halogen, or 3- to 14-membered cycloheteroalkyl (preferably, piperidinyl, piperazinyl, morpholinyl, or tetrahydrofuranyl) in which any the aforementioned hydrocarbon groups (e.g., $C_1$-$C_6)$alkyl, $(C_6$-$C_{14})$ aryl, and $(C_3$-$C_{14})$cycloalkyl) is optionally substituted with halogen, $(C_1$-$C_6)$alkyl (preferably, methyl, ethyl, propyl, or butyl), halo-substituted $(C_1$-$C_6)$alkyl (preferably, $CF_3$), OH, or $NR^{44}R^{45}$.

In another embodiment, $R^8$ is methyl, ethyl, propyl, butyl, naphthyl, phenyl, cyclopropyl, cyclobutyl, cyclopentyl, cyclohexyl, F, Br, piperidinyl, or piperazinyl, in which any the aforementioned hydrocarbon groups (e.g., methyl, ethyl, propyl, butyl, naphthyl, phenyl, cyclopropyl, cyclobutyl, cyclopentyl, and cyclohexyl) is substituted with F, Cl, Br, methyl, ethyl, propyl, or $CF_3$. In another embodiment, $R^8$ is phenyl which is unsubstituted or substituted with F, Cl, Br, methyl, ethyl, propyl, or $CF_3$.

In an embodiment, $R^6$ and $R^7$ are each independently H, $NO_2$, $SO_2CF_3$, $SO_2$—$(C_1$-$C_6)$alkyl (preferably, $SO_2CH_3$, or $SO_2CH_2CH_3$), halo-substituted $(C_1$-$C_6)$alkyl (preferably, $CF_3$), halogen, $(C_3$-$C_{14})$cycloalkyl (preferably, cyclopropyl, cyclobutyl, cyclopentyl, or cyclohexyl), or CN. In another embodiment, one of $R^6$ and $R^7$ is H, and the other is selected from $NO_2$, $SO_2CF_3$, $SO_2CH_3$, $SO_2CH_2CH_3$, $CF_3$, Cl, or F. In another embodiment, one of $R^6$ and $R^7$ is H, and the other is selected from $NO_2$, or $SO_2CF_3$. In another embodiment, both of $R^6$ and $R^7$ are H.

In an embodiment, $R^{10}$, $R^{11}$, $R^{13}$, $R^{14}$, $R^{16}$, $R^{17}R^{46}$, $R^{47}$, $R^{49}$, and $R^{50}$ are each independently H, $(C_1$-$C_6)$alkyl (preferably, methyl, ethyl, propyl or butyl), $(C_2$-$C_6)$alkenyl (preferably, ethenyl or propenyl), $(C_2$-$C_6)$alkynyl, OH, —C(O)—$(C_1$-$C_6)$alkyl (preferably, C(O)methyl, —C(O)ethyl, or —C(O)propyl), $(C_1$-$C_6)$alkoxy (preferably, methoxy, ethoxy, or propoxy), halogen, $(C_3$-$C_{14})$cycloalkyl (preferably, cyclopropyl, cyclobutyl, cyclopentyl, or cyclohexyl), $(C_6$-$C_{14})$ aryl (preferably, phenyl), 4- to 14-membered cycloheteroalkyl (preferably, piperidinyl, piperazinyl, morpholinyl, or tetrahydrofuranyl), or 5-to 14-membered heteroaryl (preferably, pyridinyl, pyrimidinyl, or pyridazinyl) wherein each of the aforementioned hydrocarbon groups (e.g., $C_1$-$C_6)$alkyl, $(C_2$-$C_6)$alkenyl, $(C_2$-$C_6)$alkynyl, $(C_3$-$C_{14})$cycloalkyl, and $(C_6$-$C_{14})$ aryl, and the $(C_1$-$C_6)$alkyl moiety of —C(O)—$(C_1$-$C_6)$ alkyl and $(C_1$-$C_6)$alkoxy) is optionally substituted by one or more substituents selected from halogen, hydroxyl, $(C_1$-$C_6)$ alkoxy, amino, $(C_1$-$C_6)$alkylamino, di($(C_1$-$C_6)$alkyl)amino or cyano;

In a further embodiment, $R^{13}$ and $R^{14}$ together with the N to which they are attached form a 4- to 8-membered cycloheteroalkyl group (preferably, piperidinyl or piperazinyl), or a 5- to 14-membered heteroaryl (preferably, pyridinyl or pyrimidinyl) each of which is substituted or unsubstituted.

or $R^{16}$ and $R^{17}$ together with the N to which they are attached form a 4- to 8-membered cycloheteroalkyl (preferably, piperidinyl or piperazinyl), or a 5- to 14-membered heteroaryl (preferably, pyridinyl or pyrimidinyl) each of which is substituted or unsubstituted.

In an embodiment, $R^{15}$, $R^{18}$, $R^{19}$, $R^{20}$, $R^{22}$, $R^{23}$, $R^{44}$, $R^{45}$, $R^{48}$, $R^{51}$, $R^{52}$, $R^{53}$, $R^{55}$, and $R^{56}$ are each independently —$(C_1$-$C_6)$alkylene-$(C_6$-$C_{14})$aryl (preferably, —$CH_2$-phenyl, —$CH_2CH_2$-phenyl, or —$CH_2CH_2CH_2$-phenyl), or —$(C_1$-$C_6)$alkylene-(5-to 14-membered heteroaryl), (preferably, —$CH_2$-pyridinyl, —$CH_2CH_2$-pyridinyl, —$CH_2$-pyrimidinyl, or —$CH_2CH_2$-pyrimidinyl) each of which is unsubstituted or substituted with one or more substituents each independently selected from halogen, OH, $(C_1$-$C_6)$alkyl (preferably, methyl, ethyl, propyl, or butyl), halo-substituted $(C_1$-$C_6)$alkyl (preferably, $CF_3$), or CN.

$R^{21}$ and $R^{54}$ are each independently $(C_6$-$C_{14})$aryl (preferably, phenyl or naphthyl), 5- to 14-membered heteroaryl, —$(C_1$-$C_6)$alkyl-$(C_6$-$C_{14})$aryl (preferably, —$CH_2$-phenyl, —$CH_2CH_2$-phenyl, or —$CH_2CH_2CH_2$-phenyl), or $(C_1$-$C_6)$alkylene-(5- to 14-membered heteroaryl) (preferably, —CH$_2$-pyridinyl, —CH$_2$CH$_2$-pyridinyl, —CH$_2$-pyrimidinyl, or —CH$_2$CH$_2$-pyrimidinyl) each of which is unsubstituted or substituted with one or more substituents each independently selected from halogen, OH, (C$_1$-C$_6$)alkyl (preferably, methyl, ethyl, or propyl), halo-substituted (C$_1$-C$_6$)alkyl (preferably, CF$_3$), or CN.

In another embodiment, the present invention includes compounds of formula (Ib):

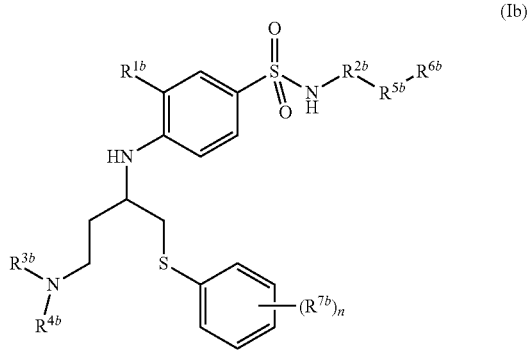

(Ib)

or a pharmaceutically acceptable salt thereof, wherein

R$^{1b}$ is H, NO$_2$, SO$_2$CF$_3$, SO$_2$(C$_1$-C$_6$)alkyl, halo-substituted (C$_1$-C$_6$)alkyl, halogen, a (C$_3$-C$_{14}$)cycloalkyl group, or CN;

R$^{2b}$ is a divalent bicyclic radical comprising a saturated cyclic structure and an unsaturated cyclic structure, wherein said unsaturated cyclic structure is attached to NH, and said saturated cyclic structure is attached to R$^{5b}$, wherein R$^{2b}$ is unsubstituted or substituted with one or more substituents each independently selected from halogen, OH, (C$_1$-C$_6$) alkyl, halo-substituted(C$_1$-C$_6$)alkyl, CN or NH$_2$;

R$^{3b}$ and R$^{4b}$ are each independently H, (C$_1$-C$_6$)alkyl, (C$_2$-C$_6$)alkenyl, (C$_2$-C$_6$)alkynyl, a (C$_6$-C$_{14}$)aryl group, a 5- to 14-membered heteroaryl group, a (C$_3$-C$_{14}$)cycloalkyl group, halogen, or a 3- to 14-membered cycloheteroalkyl group, each of which when not H may be unsubstituted or substituted with one or more of hydroxyl, cyano, nitro, (C$_1$-C$_8$)alkyl, (C$_2$-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, halogen, (C$_1$-C$_8$)alkylcarbonyl, carboxy, (C$_1$-C$_8$)alkoxycarbonyl, amino, (C$_1$-C$_8$)alkylamino, di((C$_1$-C$_8$)alkyl)amino, (C$_1$-C$_8$)alkylaminocarbonyl, di((C$_1$-C$_8$)alkyl)aminocarbonyl, (C$_1$-C$_8$)alkylcarbonylamino, (C$_1$-C$_8$)alkylcarbonyl((C$_1$-C$_8$)alkyl)amino, (C$_1$-C$_8$)alkylsulfonylamino, (C$_1$-C$_8$)alkylthio, (C$_1$-C$_8$)alkylsulfinyl, (C$_1$-C$_8$)alkylsulfonyl, aminosulfonyl, (C$_1$-C$_8$)alkylaminosulfonyl or di(C$_1$-C$_8$)alkylaminosulfonyl, where each of the afore-mentioned hydrocarbon groups (e.g., (C$_1$-C$_8$)alkyl, (C$_2$-C$_8$)alkenyl, (C$_2$-C$_8$)alkynyl, and the (C$_1$-C$_8$)alkyl, (C$_2$-C$_8$)alkenyl and (C$_2$-C$_8$)alkynyl moieties of (C$_2$-C$_8$)alkoxy, (C$_2$-C$_8$)alkenyloxy, (C$_2$-C$_8$)alkynyloxy, (C$_1$-C$_8$)alkylcarbonyl, (C$_1$-C$_8$)alkoxycarbonyl, (C$_1$-C$_8$)alkylamino, di(C$_1$-C$_8$)alkylamino, (C$_1$-C$_8$)alkylaminocarbonyl, di((C$_1$-C$_8$)alkyl) aminocarbonyl, (C$_1$-C$_8$)alkylcarbonylamino, (C$_1$-C$_8$) alkylcarbonyl((C$_1$-C$_8$)alkyl)amino, (C$_1$-C$_8$) alkylsulfonylamino, (C$_1$-C$_8$)alkylthio, (C$_1$-C$_8$)alkylsulfinyl, (C$_1$-C$_8$)alkylsulfonyl, (C$_1$-C$_8$)alkylaminosulfonyl and di((C$_1$-C$_8$)alkyl)aminosulfonyl) is optionally substituted by one or more substituents each independently selected from halogen, OH or (C$_1$-C$_8$)alkoxy;

R$^{5b}$ is a 3- to 8-membered cycloheteroalkyl, (C$_3$-C$_8$)cycloalkyl, or (C$_6$-C$_{14}$)aryl which is unsubstituted or substituted with (C$_1$-C$_6$)alkyl, halogen, OH, (C$_1$-C$_3$)alkoxy, NH$_2$, or deuterium;

R$^{6b}$ is L$_b$-R$^{8b}$;

R$^{7b}$ is hydroxyl, cyano, nitro, (C$_1$-C$_8$)alkyl, (C$_2$-C$_8$)alkenyl, (C$_2$-C$_8$)alkynyl, (C$_2$-C$_8$)alkoxy, (C$_2$-C$_8$)alkenyloxy, (C$_2$-C$_8$)alkynyloxy, halogen, (C$_1$-C$_8$)alkylcarbonyl, carboxy, (C$_1$-C$_8$)alkoxycarbonyl, amino, (C$_1$-C$_8$)alkylamino, di(C$_1$-C$_8$)alkylamino, (C$_1$-C$_8$)alkylaminocarbonyl, di((C$_1$-C$_8$) alkyl)aminocarbonyl, (C$_1$-C$_8$)alkylcarbonylamino, (C$_1$-C$_8$) alkylcarbonyl((C$_1$-C$_8$)alkyl)amino, (C$_1$-C$_8$) alkylsulfonylamino, (C$_1$-C$_8$)alkylthio, (C$_1$-C$_8$)alkylsulfinyl, (C$_1$-C$_8$)alkylsulfonyl, aminosulfonyl, (C$_1$-C$_8$)alkylaminosulfonyl or di((C$_1$-C$_8$)alkyl)aminosulfonyl, where each of the afore-mentioned hydrocarbon groups (e.g., (C$_1$-C$_8$)alkyl, (C$_2$-C$_8$)alkenyl, (C$_2$-C$_8$)alkynyl, and the (C$_1$-C$_8$)alkyl, (C$_2$-C$_8$)alkenyl and (C$_2$-C$_8$)alkynyl moieties of (C$_2$-C$_8$)alkoxy, (C$_2$-C$_8$)alkenyloxy, (C$_2$-C$_8$)alkynyloxy, (C$_1$-C$_8$)alkylcarbonyl, (C$_1$-C$_8$)alkoxycarbonyl, (C$_1$-C$_8$)alkylamino, di(C$_1$-C$_8$) alkylamino, (C$_1$-C$_8$)alkylaminocarbonyl, di((C$_1$-C$_8$)alkyl) aminocarbonyl, (C$_1$-C$_8$)alkylcarbonylamino, (C$_1$-C$_8$) alkylcarbonyl((C$_1$-C$_8$)alkyl)amino, (C$_1$-C$_8$) alkylsulfonylamino, (C$_1$-C$_8$)alkylthio, (C$_1$-C$_8$)alkylsulfinyl, (C$_1$-C$_8$)alkylsulfonyl, (C$_1$-C$_8$)alkylaminosulfonyl and di((C$_1$-C$_8$)alkyl)aminosulfonyl) is optionally substituted by one or more substituents each independently selected from halogen, OH or (C$_1$-C$_8$)alkoxy;

L$_b$ is —(C$_1$-C$_3$)alkylene-, —(C$_2$-C$_4$)alkenylene-, —C(O)—, —C(O)O—, —C(O)N(H)—, —(C$_1$-C$_3$)alkylC(O)—, —(C$_1$-C$_3$)alkyl-C(O)O—, or a bond, wherein L$_b$ is unsubstituted or substituted by one or more (C$_1$-C$_4$)alkyl, halo-substituted(C$_1$-C$_4$)alkyl, or (C$_3$-C$_8$)cycloalkyl;

R$^{8b}$ is (C$_6$-C$_{14}$)aryl, a 5- to 14-membered heteroaryl, a 3- to 8-membered cycloheteroalkyl, or a (C$_3$-C$_{14}$)cycloalkyl, each of which is unsubstituted or substituted with one or more substituents each independently selected form halogen, OH, (C$_1$-C$_6$)alkyl, halo-substituted(C$_1$-C$_6$)alkyl, or CN; and n is 0, 1, 2, 3, or 4.

In an embodiment, the present invention further includes compounds of formula (Ib) where R$^{2b}$ is defined as A in formula I. In another embodiment, the present invention includes compounds of formula (Ib) where n is 0, 1, or 2. In another embodiment, n is 0.

In another embodiment, the present invention includes compounds of formula (Ib) where R$^{3b}$ and R$^{4b}$ are each independently H, (C$_1$-C$_6$)alkyl (preferably, methyl, ethyl or propyl), (C$_2$-C$_6$)alkenyl, (C$_2$-C$_6$)alkynyl, (C$_6$-C$_{14}$)aryl (preferably, phenyl), a 5- to 14-membered heteroaryl group (preferably, pyridinyl or pyrimidinyl), (C$_3$-C$_{14}$)cycloalkyl (preferably, cyclopropyl, cyclobutyl, cyclopentyl, or cyclohexyl), or halogen (preferably, F, Cl, or Br).

Compounds of particular interest include:

(R)-N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

N-(7-((2S)-1-((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethyl-sulfonyl) benzenesulfonamide;

(R)-4-(4-(dimethylamino)-1-(phenylthio)butan-2-ylamino)-N-(7-(1-((4'-fluorobiphenyl-2-yl)methyl)piperidin-4-yl)-5,6,7,8-tetrahydropyrido[3,4-d]pyrimidin-4-yl)-3-(trifluoromethylsulfonyl)benzenesulfonamide;

(R)-N-(7-(1(4'-bromobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chloro-5-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chloro-4-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chloro-3-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4[(R)-3-(4-ethyl-piperazin-1-yl)-1-phenylsulfanylmethyl-propylamino]-3-trifluoromethanesulfonyl-benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanyl methyl)-3-dimethylamino-propylamino]-3-trifluoromethanesulfonyl-benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

(R)-N-(7-(1-((4'-chloro-4-methoxybiphenyl-2-yl)methyl)piperidin-4-yl)-5,6,7,8-tetrahydropyrido-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2,6-dichlorophenylthio)-4-(dimethylamino)butan-2-ylamino)-3-(trifluoromethylsulfonyl)benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3,4-dichloro-phenylsulfanylmethyl)-3-dimethylamino-propylamino]-3-trifluoromethanesulfonyl-benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(2-fluoro-phenylsulfanylmethyl)-propylamino]-3-trifluoromethanesulfonyl-benzenesulfonamide;

N-{(R)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide;

(R)-N-(2-chloro-7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-(7-(1-((4'-chlorobiphenyl-2-yl)methyl)-3-fluoropiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((4'-chlorobiphenyl-2-yl)methyl)-3-fluoropiperidin-4-yl)-2-(trifluoromethyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

(R)-N-(7-(1-((2-(4-chlorophenyl)-5,5-dimethylcyclohex-1-enyl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)-benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((S)-1-(4'-chlorobiphenyl-2-yl)ethyl)-4-deuteropiperidin-4-yl)-2-(trifluoromethyl)-5,6,7,8-tetrahydropyrido[3,4-d]pyrimidin-4-yl)-4-((R)-1-(2-fluorophenylthio)-4-(4-methylpiperazin-1-yl)butan-2-ylamino)-3-(trifluoromethylsulfonyl)benzenesulfonamide;

N-(7-{1-[2-(4-Chloro-phenyl)-4,4-dimethyl-cyclohex-1-enylmethyl]-4-deutero-piperidin-4-yl}-5,6,7,8-tetrahydro-pyrido[3,4-d]pyrimidin-4-yl)-4-[(R)-3-(isopropyl-methyl-amino)-1-phenylsulfanylmethyl-propylamino]-3-trifluoromethanesulfonyl-benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide;

N-(7-{1-[(R)-1-(4'-Chloro-biphenyl-2-O-ethyl]-4-deuteropiperidin-4-yl}-5,6,7,8-tetrahydro-pyrido[3,4-d]pyrimidin-4-yl)-4-(R)-3-morpholin-4-yl-1-phenylsulfanylmethyl-propylamino)-3-trifluoromethanesulfonyl-benzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)-benzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(4-ethylpiperazin-1-yl)-1-(phenylthio)butan-2-ylamino)-3-(trifluoromethyl sulfonyl)benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-dimethylamino-1-phenyl-sulfanylmethyl-propylamino)-3-trifluoromethanesulfonyl-benzenesulfonamide;

N-{7-[1-(3'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide;

N-(7-(1-((2'-chlorobiphenyl-2-yl)methyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide; and (R)-4-(4-(dimethylamino)-1-(phenylthio)butan-2-ylamino)-N-(7-(1-((4'-(trifluoromethyl)biphenyl-2-yl)methyl)piperidin-4-yl)-5,6,7,8-tetrahydropyrido[3,4-d]pyrimidin-4-yl)-3-(trifluoromethylsulfonyl)benzenesulfonamide;

or a pharmaceutically acceptable salt thereof.

More particularly, compounds such as:

N-(7-((2S)-1-((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phen ylthio)butan-2-ylamino)-3-(trifluoromethyl-sulfonyl)benzenesulfonamide;

(R)-4-(4-(dimethylamino)-1-(phenylthio)butan-2-ylamino)-N-(7-(1-((4'-fluorobiphenyl-2-yl)methyl)piperidin-4-yl)-5,6,7,8-tetrahydropyrido[3,4-d]pyrimidin-4-yl)-3-(trifluoromethylsulfonyl)benzenesulfonamide;

(R)-N-(7-(1((4'-bromobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chloro-4-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(2-fluoro-phenylsulfanylmethyl)-propylamino]-3-trifluoromethanesulfonyl-benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-(7-(1-1-(4'-chlorobiphenyl-2-yl)ethyl)piperidin-4-yl)-5,6,7,8-tetrahydropyrido[3,4-d]pyrimidin-4-yl)-44(R)-4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide;

and N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-dimethylamino-1-phenyl-sulfanylmethyl-propylamino)-3-trifluoromethanesulfonyl-benzenesulfonamide; or a pharmaceutically acceptable salt thereof.

In another aspect of the present invention a pharmaceutical composition is provided which comprises a compound of the present invention and a pharmaceutically acceptable carrier or excipient. The pharmaceutical composition optionally comprises at least one additional pharmaceutical agent (suitable pharmaceutical agents are described herein below).

In yet another aspect of the present invention, a method of inhibiting Bcl-2 activity is provided comprising the step of administering to a subject in need thereof (i) a therapeutically effective amount of a compound or the present invention, or (ii) a pharmaceutical composition comprising a compound of the present invention and at least one pharmaceutically acceptable excipient.

Still further, the present invention includes a method of treating a proliferative disease comprising the step of administering to a subject in need thereof (i) a therapeutically effective amount of a compound of the present invention, or (ii) a pharmaceutical composition comprising a compound of the present invention, and at least one pharmaceutically acceptable excipient.

Alternatively, the method for treating a proliferative disease or inhibiting Bcl-2 activity may include a combination therapy which comprises the step(s) of administering (i) a first composition comprising a compound of the present invention and a pharmaceutically acceptable carrier or excipient; and (ii) a second composition comprising at least one additional pharmaceutical agent and a pharmaceutically acceptable carrier or excipient;

wherein said at least one additional pharmaceutical agent is an anticancer agent, chemotherapy agent, or antiproliferative compound.

The first composition and the second composition may be administered simultaneously or sequentially in any order.

Also included herein is administering a compound of the present invention or a pharmaceutical composition including a compound of the present invention for use in therapy.

Preferably, the disease, disorder, or syndrome is hyperproliferative in a subject, wherein said subject is an animal including humans, and is selected from the group consisting of cancer and inflammation.

The present invention further includes a pharmaceutical composition comprising (i) a compound of the present invention, and (ii) a pharmaceutically acceptable carrier or excipient. Still further, the present invention includes a pharmaceutical composition comprising a compound of the present invention in combination with a second active agent, and a pharmaceutically acceptable carrier or excipient.

Definitions

As used herein, "alkyl" refers to a straight chain or branched hydrocarbon ($C_nH_{2n+1}$). Alkyl moieties having from 1 to 5 carbons are referred to as "lower alkyl" and examples include, but are not limited to, methyl, ethyl, n-propyl, isopropyl, n-butyl, sec-butyl, t-butyl, isobutyl, n-pentyl, iso-pentyl, and neopentyl). The term "alkylene" refers to an alkyl moiety where the moiety contains two binding sites. The alkylene group may be straight (e.g., —$CH_2$—, —$(CH_2)_2$—, —$(CH_2)_3$—, —$(CH_2)_4$—, etc.) or branched (e.g., —$CH(CH_3)$—, —$C(CH_3)_2$—, —$CH_2CH(CH_3)$—, —$CH(CH_3)$—$CH_2$—, —$C(CH_3)_2$—$CH_2$-, etc.). Suitable alkylene moieties are the same as those described above for alkyl except with two binding sites instead of just one.

"Halo-substituted alkyl" refers to an alkyl group substituted with halogen groups, e.g. fluoro groups. For example, where the substituent is fluoro, common haloalkyl groups are trifluoroalkyl, 2,2,2-trifluoroethyl or 2,2,2,1,1-pentafluoroethyl groups. Generally, a halo-substituted ($C_1$-$C_6$) alkyl is substituted with up to seven halogen atoms, which may be the same or different. A perhalo alkyl refers to an alkyl group where each of the hydrogen atoms is replaced with a halogen (e.g., trifluoromethyl).

The term "alkenyl" refers to a monovalent group derived from a hydrocarbon having at least one carbon-carbon double bond. For example, vinyl, prop-1-enyl, prop-2-enyl, 2-methylprop-2-enyl, 3-methylbut-2-enyl, and the like. The term "alkenylene" refers to an alkenyl moiety containing two binding sites. For example, —$CH_2$—CH=CH—$CH_2$—. Suitable alkenylene moieties are the same as those described above for alkenyl except with two binding sites instead of just one.

The term "alkynyl" refers to a monovalent group derived from a hydrocarbon having at least one carbon-carbon triple bond. The term "$C_2$-$C_6$-alkynyl" refers to a monovalent group derived from a hydrocarbon having two to six carbon atoms and comprising at least one carbon-carbon triple bond.

The term "alkoxy" refers to a group in which an alkyl group is attached to oxygen, wherein alkyl is as previously defined.

The term "cycloalkyl" refers to a monocyclic, bicyclic, or spiral, fully or partially saturated carbocyclic ring. The cycloalkyl may be attached using any of the ring members. Suitable cycloalkyl groups include cyclopropyl, cyclobutyl, cyclopentyl, cyclohexyl, cycloheptyl or cyclooctyl. A partially monocyclic saturated ring includes moieties such as cyclohexenyl, cyclopropenyl, cyclobutenyl, cyclopentenyl, cyclohexadienyl, etc. The term "cycloalkylene" refers to a fully saturated carbocyclic ring(s) having two points of attachment. The carbocyclic ring may be a single ring, a bicyclic ring, or a spiral ring where the two binding sites on the bicyclic ring and spiral ring may be on the same ring or different rings. See, e.g., the illustration below.

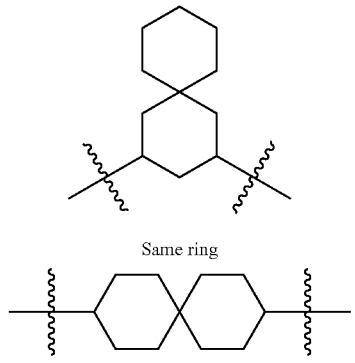

Same ring

Different ring

The term "aryl" refers to aromatic moieties having a single (e.g., phenyl) or a fused ring system (e.g., naphthalene, anthracene, phenanthrene, etc.). A typical aryl group is a 6- to 14-membered aromatic carbocyclic ring(s). A fused aromatic ring system may also include a phenyl fused to a partially or fully saturated cycloalkyl. For example, 2,3-dihydroindenyl, 1,2,3,4-tetrahydronaphthalenyl, 1,2-dihydronaphthalenyl, 2,3-dihydronaphthalenyl, 9,10-dihydroanthracenyl, fluorenyl, and the like.

The term "arylene" refers to a carbocyclic aromatic moiety having two binding sites. Suitable arylenes include those groups described above for an aryl moiety except with two binding sites rather than one. For example, 1,2-phenylene, 1,3-phenylene, 1,4-phenylene, 1,3-naphthylene, 1,4-naphthylene, 1,5-naphthylene, 1,6-naphthylene, 1,7-naphthylene, 2,3-naphthylene, 2,4-napthylene, 2,5-naphthylene, 2,6-naphthylene, 2,7-naphthylene, 3,4-naphthylene, 3,5-naphthylene, 3,6-naphthylene, 3,7-naphthylene, etc. The two binding sites on the fused arylene system may be on the same ring or different rings.

The term "heteroaryl" refers to a monocyclic or fused ring system, wherein the monocyclic and at least one of the bicyclic fused rings is an aromatic ring comprising either (a) 1 to 4 nitrogen atoms, (b) one oxygen or one sulphur atom or (c) 1 oxygen atom or 1 sulphur atom and 1 or 2 nitrogen atoms, and the fused ring may be an aryl group, another heteroaryl, a saturated or partially unsaturated cycloalkyl, or a saturated or partially unsaturated heterocycle. The heteroaryl may optionally include one to three ring members selected from the group consisting of O, S or N. The heteroaryl may be attached using any of the ring members. Suitable monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. Suitable fused heteroaryl groups include indolyl, benzofuranyl, quinolyl, isoquinolyl indazolyl, indolinyl, isoindolyl, indolizinyl, benzamidazolyl, and quinolinyl. The term "heteroarylene" refers to a biradical heteroaryl monocyclic or fused ring system wherein the ring(s) have two points of attachment which may be on the same ring or different rings in the case of a fused ring system.

The term "Cycloheteroalkyl" or "heterocycle" refers to a nonaromatic ring(s) that are either partially or fully saturated and may exist as a single ring, bicyclic ring or a spiral ring comprising one or two ring members selected from the group consisting of $N(R^{27})$, O or $S(O)_r$. The cycloheteroalkyl may optionally include one to three ring members each independently selected from $C(=O)$, $N(R^{28})q$, O or $S(O)r$ where $R^{27}$ or $R^{28}$ is H or $(C_1-C_6)$alkyl, q is 0-1 and r is 0-2. The cycloheteroalkyl may be attached using any of the ring members. Suitable heterocycloalkyl groups include [1,3] dioxolane, [1,4] dioxane, oxiranyl, aziridinyl, oxetanyl, azetidinyl, tetrahydrofuranyl, pyrrolidinyl, tetrahydropyranyl, piperidinyl, morpholino, thiomorpholinyl, piperazinyl, azepinyl, oxapinyl, oxazepinyl and diazepinyl. The term "cycloheteroalkylene" refers to a biradical heterocyle having two points of attachment. The heterocyclene ring may be a single ring, a bicyclic ring, or a spiral ring where the two binding sites on the bicyclic ring and spiral ring may be on the same ring or different rings. See, e.g., the illustration below.

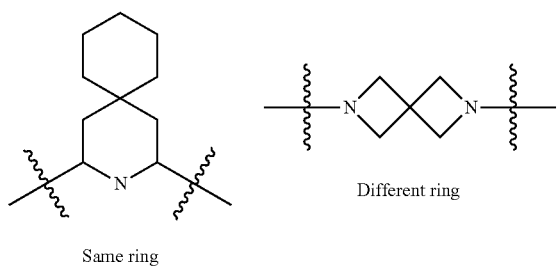 [SMILES: *C1CC2(CCCCC2)CC(*)N1 ; *N1CC2(C1)CN(*)C2]

Same ring    Different ring

"Halogen" or "halo" may be fluorine, chlorine, bromine or iodine.

It is to be understood that the terminology C(O) refers to a —C=O group, whether it be ketone, aldehyde or acid or acid derivative. Similarly, S(O) refers to a —S=O group.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry. A preferred animal is human.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "compounds of the present invention" (unless specifically identified otherwise) refer to compounds of Formula (I) and (Ib), and salts thereof, as well as all stereoisomers (including diastereoisomers and enantiomers), tautomers and isotopically labeled compounds (including deuterium substitutions), as well as inherently formed moieties (e.g., polymorphs, solvates and/or hydrates). For purposes of this invention, hydrates and solvates are considered compositions comprising a compound of the present invention and an excipient (e.g., water or a solvent).

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Scheme 1 below illustrates how one could make compounds of Formula (I) or (Ib). Those of skill in the art will know how to modify the conditions and/or starting materials to make other useful derivatives.

Scheme 1

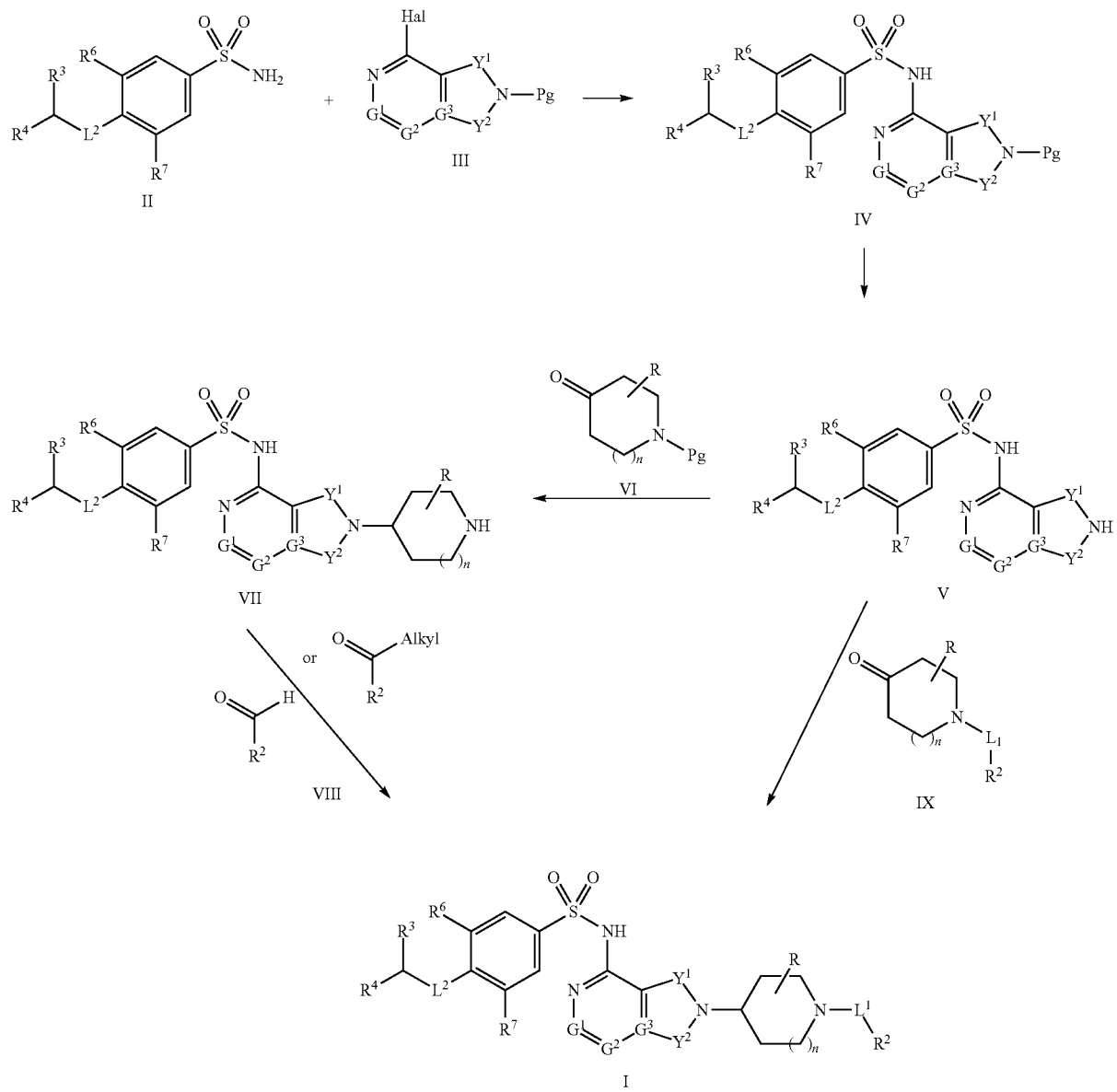

Compounds of Formula I can be prepared by first performing a metal-catalyzed cross-coupling of sulfonamides of Type II with heteroaryl halides of Type III (Hal is typically Cl or Br and Pg is a protecting group) to afford heteroaryl sulfonamides of Type IV. For example, the cross-coupling can be accomplished using tris(dibenzylideneacetone)dipalladium (0)(also referred to as $Pd_2(dba)_3$), 2-(2-dicyclohexyl-phosphanylphenyl)-N,N-dimethylaniline (also know as DavePhos), cesium carbonate in dioxane at elevated temperatures (e.g., about 180° C.). Alternatively, the cross-coupling can be accomplished using copper iodide, cesium carbonate, and N,N-dimethylcyclohexane-1,2-diamine in toluene at about 90° C.

The nitrogen protection group may then be removed using conditions appropriate for the particular protecting group used to produce intermediates of Type V.

Intermediates of Type V can then be subjected to reductive amination, either with ketones of Type VI, to afford, following removal of the protecting group, intermediates of Type VII, or with ketones of Type IX, to afford compounds of Formula I. A second reductive amination of amines of Type VII with carbonyl compounds of Type VIII also affords compounds of Formula I. For example, the reductive amination may be accomplished using sodium cyanoborohydride or sodium triacetoxyborohydride using conditions well-known to those of skill in the art.

It is recognized that in order to illustrate the general scheme, variable A as described in the claims is shown as:

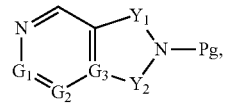

and variable R¹ as described in the claims is shown as

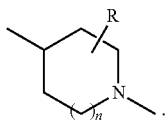

The compounds may be isolated and used as the compound per se or as its salt. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention includes all pharmaceutically acceptable isotopically-labeled compounds of the invention, i.e. compounds of formula (I) and (Ib), wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I) and (Ib), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) and (Ib) can generally be prepared by conventional techniques known to those skilled in the art or by processes analogous to those described in the accompanying Examples and Preparations using an appropriate isotopically-labeled reagents in place of the non-labeled reagent previously employed.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

A compound of the formula (I) or (Ib) may also be used to advantage in combination with other antiproliferative compounds. Such antiproliferative compounds include, but are not limited to aromatase inhibitors; antiestrogens; topoisomerase 1 inhibitors; topoisomerase I1 inhibitors; microtubule active compounds; alkylating compounds; histone deacetylase inhibitors, compounds which induce cell differentiation processes; cyclooxygenase inhibitors; MMP inhibitors; mTOR inhibitors, antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3, Hsp90 inhibitors, kinesin spindle protein inhibitors, PI3K inhibitors, RAF inhibitors, EDG binders, antileukemia compounds, ribonucleotide reductase inhibitors, 5-adenosylmethionine decarboxylase inhibitors, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors. More particularly, some therapeutic agents with which a compound of the formula (I) or (Ib) may be used include doxorubicin, docetaxel, 5FU, Camptothecin, Erlotinib, Paclitaxel, Carboplatin, Etoposide, and Gemcitabine.

The compounds of the present invention are useful as both prophylactic and therapeutic treatments for diseases or conditions related to the hyperactivity of Bcl-2. Thus, as a further aspect, the invention relates to a method for treating a disease or condition related to the hyperactivity of Bcl-2, or a disease or condition modulated by the Bcl-2, comprising administration of an effective therapeutic amount of a compound of formula (I) or (Ib) or a pharmaceutically acceptable salt thereof. As a further aspect, the invention relates to a method for treating proliferative diseases, such as cancer, comprising administration of an effective amount of a compound of formula (I), (Ib), or a pharmaceutically acceptable salt thereof. Examples of cancers include but are not limited to: breast cancer, colorectal cancer, ovarian cancer, pancreatic cancer, or prostate cancer, chronic lymphocytic leukemia, diffuse large B-cell lymphomas, follicular lymphomas, chronic or acute leukemia, chronic myeloid leukemia, lymphoid malignancies of T-cell or B-cell origin, lung cancers, such as small cell lung cancer and non-small cell lung cancer, melanoma or other skin cancers, multiple myeloma, ovarian cancer, gastrointestinal cancer (gastric, colorectal, and duodenal), bladder cancer, uterine cancer, cervical cancer, sarcoma of soft tissue origin, kidney cancer, brain tumors, hepatocellular cancer, head and neck cancer, cervical cancer, fibrosarcoma, and other cancers.

The present invention is further exemplified, but not limited, by the following representative examples, which are intended to illustrate the invention and are not to be construed as being limitations thereof.

EXAMPLES

The structure of final products described herein can be confirmed by standard analytical methods, e.g., spectrometric and spectroscopic methods (e.g., MS, NMR, HPLC). Retention times provided in the Examples below were observed on an Agilent 1100 HPLC system; Inertsil ODS3 100×3mm C18 column; flow rate of 1.0 mL/minute; gradient of 5-95% acetonitrile/water with 0.1% formic acid. Compounds are purified by standard methods, e.g., crystallization, flash chromatography, or reversed phase HPLC.

The following abbreviations have the corresponding meaning in the Examples below.

aq. Aqueous

DCE 1,2-Dichloroethane

DIPEA Diisopropylethylamine

DMA Dimethylacetamide

DME 1,2-Dimethoxyethane

DMF Dimethylformamide eq. equivalents

HPLC High-performance liquid chromatography

HR-MS High-resolution mass spectrometry

MS Mass spectrometry

NMR Nuclear magnetic resonance sat. saturated

SPE Solid-phase extraction

TOF Time-of-Flight mass spectrometry

Preparation of Key Intermediates

Synthesis of Type II Intermediates:

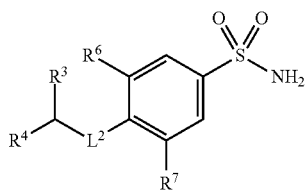

II

Intermediate 1

(R)-N1,N1-Dimethyl-4-phenylsulfanyl-butane-1,3-diamine

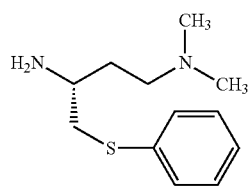

Intermediate 1 was prepared as described by Wendt, M. D., et al., in *J. Med. Chem.* 2006, 49, 1165-1181.

Intermediate 2

(R)-3-Morpholin-4-yl-1-phenylsulfanylmethyl-propylamine

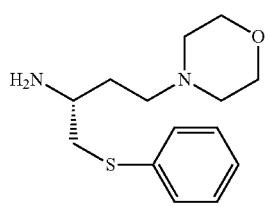 [SMILES: N[C@H](CCN1CCOCC1)CSc1ccccc1]

Intermediate 2 was prepared as described by Wendt, M. D., et al., in *J. Med. Chem.* 2006, 49, 1165-1181.

Intermediate 3

4-Fluoro-3-(trifluoromethylsulfonyl)benzenesulfonamide

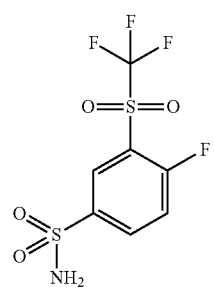 [SMILES: NS(=O)(=O)c1ccc(F)c(S(=O)(=O)C(F)(F)F)c1]

Intermediate 3 was prepared as described by Park, C., et al., in *J. Med. Chem.* 2008, 51, 6902-6915.

Intermediate 4

4-((R)-3-Dimethylamino-1-phenylsulfanylmethyl-propylamino)-3-trifluoromethanesulfonyl-benzenesulfonamide

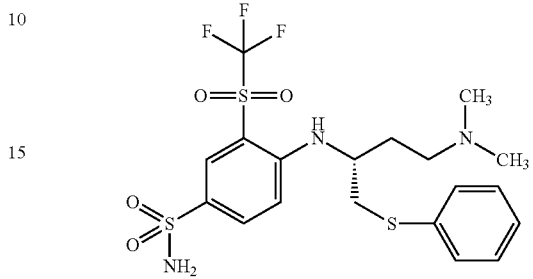

A solution of 4-fluoro-3-(trifluoromethylsulfonyl)benzenesulfonamide (685 mg, 2.3 mmol), (R)—N1,N1-dimethyl-4-phenylsulfanyl-butane-1,3-diamine (500 mg, 2.3 mmol), and DIPEA (0.78 mL, 4.5 mmol) in DMA (18.8 mL) was heated to 100° C. for 6 hours. The reaction was cooled to room temperature and diluted with EtOAc/heptanes (1:1, 50 mL). This solution was washed with water, the layers were separated, and the aqueous layer was extracted with EtOAc/heptanes (1:1) (50 mL×3). The combined organic layers were washed with water and brine, dried over $MgSO_4$, and concentrated to afford the title compound as a yellow solid (965 mg, 82% yield). MS (ESI) m/e (M+H$^+$): 512.2

Intermediate 5

4-((R)-3-Morpholin-4-yl-1-phenylsulfanylmethyl-propylamino)-3-trifluoromethanesulfonyl-benzenesulfonamide

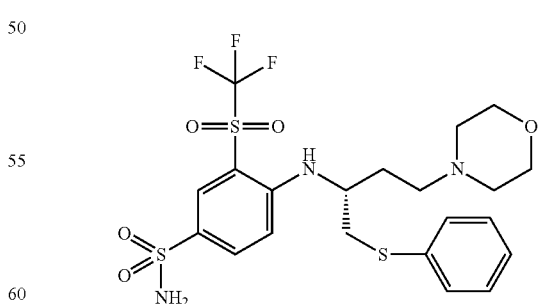

The title compound was prepared from 4-fluoro-3-(trifluoromethylsulfonyl)-benzenesulfonamide and (R)-3-morpholin-4-yl-1-phenylsulfanylmethyl-propylamine using the procedure described for Intermediate 4. MS (ESI) m/e (M+H$^+$): 553.6.

Intermediate 6

(R)-4-(4-(dimethylamino)-1-(phenylthio)butan-2-ylamino)-3-(trifluoromethyl)benzenesulfonamide

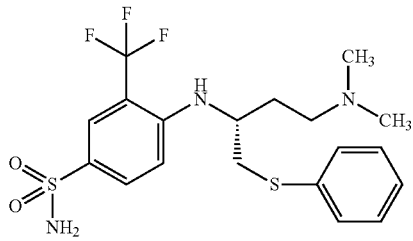 [SMILES: CN(C)CC[C@H](CSc1ccccc1)Nc1ccc(S(N)(=O)=O)cc1C(F)(F)F]

The title compound was prepared from 4-fluoro-3-(trifluoromethyl)-benzenesulfonamide and (R)—N1,N1-dimethyl-4-phenylsulfanyl-butane-1,3-diamine using the procedure described for Intermediate 4.

Intermediate 7

(R)-3-cyano-4-(4-(dimethylamino)-1-(phenylthio)butan-2-ylamino)benzenesulfonamide

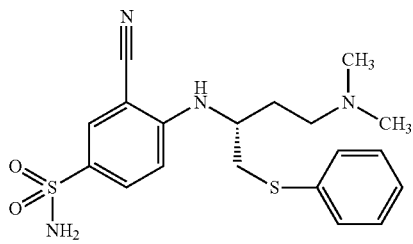 [SMILES: CN(C)CC[C@H](CSc1ccccc1)Nc1ccc(S(N)(=O)=O)cc1C#N]

The title compound was prepared from 4-fluoro-3-(cyano)benzenesulfonamide and (R)—N1,N1-dimethyl-4-phenylsulfanyl-butane-1,3-diamine using the procedure described for Intermediate 4.

Intermediate 8

(R)-4-(4-(dimethylamino)-1-(phenylthio)butan-2-ylamino)-3,5-difluorobenzenesulfonamide

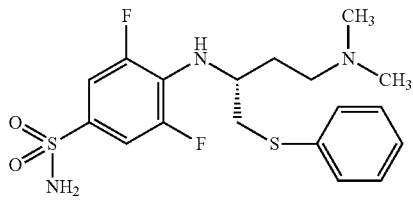 [SMILES: CN(C)CC[C@H](CSc1ccccc1)Nc1c(F)cc(S(N)(=O)=O)cc1F]

The title compound was prepared from 3,4,5-trifluorobenzenesulfonamide and (R)—N1,N1-dimethyl-4-phenylsulfanyl-butane-1,3-diamine using the procedure described for Intermediate 4.

Intermediate 9

4-((R)-3-Dimethylamino-1-phenylsulfanylmethyl-propylamino)-3-nitro-benzenesulfonamide

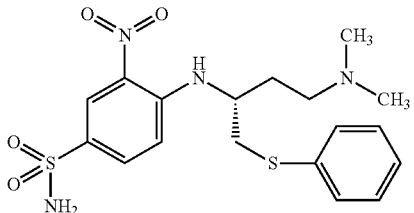

Intermediate 9 was prepared as described by Wendt, M. D., et al., in *J. Med. Chem.* 2006, 49, 1165-1181.

Synthesis of Type III Intermediates

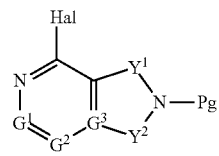

III

Intermediate 10

4-Chloro-5,8-dihydro-6H-pyrido[3,4-d]pyrimidine-7-carboxylic acid tert-butyl ester STEP A: 1-Benzyl-3-oxo-piperidine-4-carboxylic acid ethyl ester (5.0 g, 16.8 mmol) was stirred in dry ethanol (55 mL). The flask was evacuated and filled with nitrogen prior to the addition of 10% Pd/C (1.0 g). The resulting suspension was stirred for 16 hours under an atmosphere of hydrogen. The reaction mixture was filtered through Celite and concentrated to afford a yellow solid (2.9 g). This was immediately dissolved in $CH_2Cl_2$ (100 mL), treated with Bac-anhydride (4.4 g, 20.2 mmol) and DIPEA (4.3 g, 33.6 mmol), and stirred for 16 hours at room temperature. The organics were washed sequentially with HCl (IN), water and brine, dried over magnesium sulfate, filtered, and concentrated to afford 3-oxo-piperidine-1,4-dicarboxylic acid 1-tert-butyl ester 4-ethyl ester as a clear oil (4.8 g, 100% yield). MS (ESI) m/e (M+H$^+$): 271.36

STEP B: 3-Oxo-piperidine-1,4-dicarboxylic acid 1-tert-butyl ester 4-ethyl ester (4.6 g, 16.8 mmol) was dissolved in EtOH (90 mL), and sodium ethoxide (2.3 g, 33.6 mmol) and formamidine hydrochloride (2.0 g, 25.2 mmol) were sequentially added. The resulting suspension was heated to 70° C. and stirred for 5 hours, and then the reaction mixture was cooled to room temperature and concentrated. The residue was dissolved in saturated ammonium chloride and extracted with ethyl acetate. The aqueous phase was adjusted to pH ~5.5 using concentrated AcOH, and extracted several more times with ethyl acetate. The combined organic layers were sequentially washed with water and brine, dried, and concentrated to afford 4-hydroxy-5,8-dihydro-6H-pyrido[3,4-d]pyrimidine-7-carboxylic acid tert-butyl ester as a brown solid (1.8 g, 42% yield). MS (ESI) m/e (M+H$^+$)=251.28

STEP C: A mixture of 4-hydroxy-5,8-dihydro-6H-pyrido[3,4-d]pyrimidine-7-carboxylic acid tert-butyl ester (1.4 g, 5.6 mmol) and triphenylphosphine (2.9 g, 11.1 mmol) was stirred in DCE (41 mL) until the solution became clear, and then carbon tetrachloride (1.6 mL, 16.7 mmol) was added. The reaction mixture was heated to 70° C. and stirred for 2.5 hours. The volatiles were removed in vacuo and the crude material was directly purified by flash chromatography on silica gel (0-50% EtOAc/heptanes) to afford the title compound as an off-white solid (1.31 g, 87% yield). MS (ESI) m/e (M+H$^+$): 269.73

Intermediate 11 tert-Butyl 4-chloro-2-(trifluoromethyl)-5,6-dihydro-pyrido[3,4-d]pyrimidine-7(8H)-carboxylate

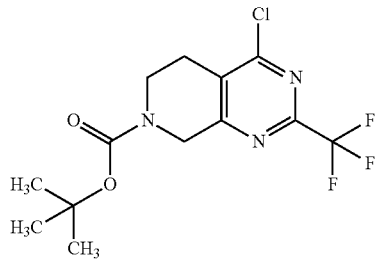 [SMILES: CC(C)(C)OC(=O)N1CCc2c(Cl)nc(C(F)(F)F)nc2C1]

STEP A: Sodium ethoxide was prepared by combining sodium metal (0.5 g, 21.8 mmol) and ethanol (33 mL). At ambient temperature, trifluoroacetamidine (1.35 g, 12.0 mmol) was added, followed immediately by addition of ethyl 1-benzyl-3-oxo-4-piperidinecarboxylate hydrochloride (2.92 g, 9.81 mmol) in portions over 15 minutes. The reaction was stirred at ambient temperature for 1 hour and then heated to 80° C. for 16 hours. The reaction was then cooled to ambient temperature, and the solvent was removed in vacuo. The resulting dark red foamy solid was taken up in diethyl ether (40 mL) and 1N aqueous NaOH (40 mL). The layers were separated, and the aqueous layer was washed with Et$_2$O (40 mL). The combined organic layers were extracted with 1N NaOH (10 mL). The combined aqueous layers were cooled to 0° C. and acidified to pH 7 with concentrated HCl. A tan solid precipitated which was isolated by slow filtration. Drying overnight over the filter afforded 7-benzyl-2-(trifluoromethyl)-5,6,7,8-tetrahydropyrido[3,4-d]pyrimidin-4-ol (2.35 g, 78% yield). MS (ESI) m/e (M+H$^+$)=310.4.

STEP B: To 7-benzyl-2-(trifluoromethyl)-5,6,7,8-tetrahydropyrido[3,4-d]pyrimidin-4-ol (0.47 g, 1.52 mmol) partially dissolved in methanol (20 mL) was added palladium hydroxide on carbon (70 mg, wet, 20% by weight dry basis). The reaction was stirred for 20 hours in a Parr shaker under a pressure of 50 psi hydrogen. The reaction was then filtered through a Celite plug, eluting with methanol (400 mL). The filtrate was concentrated in vacuo to yield 2-(trifluoromethyl)-5,6,7,8-tetrahydropyrido[3,4-d]pyrimidin-4-ol as a light beige solid (255 mg, 77% yield). $^1$H NMR (400 MHz, MeOD) δ ppm 4.09 (s, 2H), 3.48 (t, J=6.32 Hz, 2H), 2.78 (t, J=6.32 Hz, 2H).

STEP C: To a stirring mixture of 2-(trifluoromethyl)-5,6,7,8-tetrahydropyrido[3,4-d]pyrimidin-4-ol (0.246 g, 1.122 mmol) in tetrahydrofuran (11 mL) was added a solution of di-tert-butyl dicarbonate (0.269 g, 1.235 mmol) in tetrahydrofuran (11 mL). The mixture was stirred at ambient temperature for 16 h and was then concentrated in vacuo. The crude residue was purified by flash chromatography on silica gel (eluent: 0 to 7% methanol/dichloromethane) to afford tert-butyl 4-hydroxy-2-(trifluoromethyl)-5,6-dihydropyrido[3,4-d]pyrimidine-7(8H)-carboxylate as a light yellow foamy solid (0.306 g, 85% yield). MS (ESI) m/e (M−H)$^−$=318.3.

STEP D: tert-Butyl 4-hydroxy-2-(trifluoromethyl)-5,6-dihydropyrido[3,4-d]pyrimidine-7(8H)-carboxylate (5.12 g, 16.05 mmol) was combined with triphenylphosphine (8.42 g, 32.1 mmol) and stirred in dichloroethane (160 mL) at ambient temperature for 15 minutes, and then carbon tetrachloride (7.41 g, 48.1 mmol) was added. The reaction was stirred at 70° C. for 3 hours, cooled to room temperature, and concentrated in vacuo. The crude residue was purified by flash chromatography on silica gel (elution gradient from 0% to 3% methanol/DCM) to afford the title compound as a clear oil (5.22 g, 86% yield). MS (ESI) m/e (M−H)$^−$=336.3.

Intermediate 12

3-Bromo-4,5,7,8-tetrahydro-1,2,3a,6-tetraaza-azulene-6-carboxylic acid tert-butyl ester

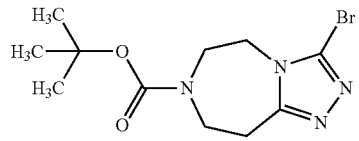 [SMILES: CC(C)(C)OC(=O)N1CCc2nnc(Br)n2CC1]

STEP A: To a stirred solution of tert-butyl 5-oxo-1,4-diazepane-1-carboxylate (1000 mg, 4.67 mmol) in dichloromethane (10 mL) was added trimethyloxonium tetrafluoroborate (690 mg, 4.67 mmol) under nitrogen and the reaction mixture was stirred for 16 hours. At this point, formic hydrazine (280 mg, 4.67 mmol) in dichloromethane (8 mL) was added, and the reaction was stirred for an additional 16 hours. The reaction mixture was then concentrated under reduced pressure, resuspended in methanol (10 mL), and heated to reflux for 16 hours. The reaction mixture was concentrated and purified via flash chromatography on silica gel (0-50% 2N NH$_3$ in methanol in CH$_2$Cl$_2$) to afford 4,5,7,8-tetrahydro-1,2,3a,6-tetraaza-azulene-6-carboxylic acid tert-butyl ester (680 mg, 61% yield). MS [m/z; (M+1)$^{3O}$]: 319.3

STEP B: To a suspension of 4,5,7,8-tetrahydro-1,2,3a,6-tetraaza-azulene-6-carboxylic acid tert-butyl ester (200 mg, 0.839 mmol) in water was added 10N NaOH until a clear solution was formed. Br$_2$ (0.432 mL, 8.39 mmol) was then added slowly while maintaining a pH of 12 by addition of conc. NaOH. The reaction was stirred at ambient temperature for 16 hours. The reaction mixture was then acidified to pH ~4 with 6 M HCl. The organics were extracted three times with CH$_2$Cl$_2$. The combined organic layers were washed with brine, dried over Na$_2$SO$_4$, filtered and concentrated under reduced pressure to afford the title compound as a white solid (185 mg, 70% yield).

$^1$H NMR (400 MHz, DMSO-d$_6$) δ ppm 1.43 (s, 9H), 3.05 (br. s., 2H), 3.54 (br. s., 2H), 3.63-3.71 (m, 2H), 4.10 (br. s., 2H).

General Procedure for the Pd-catalyzed Cross-coupling of Sulfonamides H with Heteroaryl Chlorides III

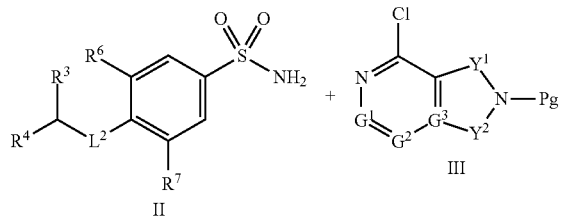

A 20 mL oven-dried vial equipped with a teflon cap was charged with Pd$_2$(dba)$_3$ (0.01 eq), cesium carbonate (1.4 eq), and 2'-(dicyclohexylphosphino)-N,N-dimethylbiphenyl-2-amine (DavePhos) (0.03 eq). The vial was then capped and purged with nitrogen. Dioxane (1.5 mL) was added, and the resulting suspension was stirred for 15 minutes under an atmosphere of nitrogen. A solution of sulfonamide (1 eq) and heteroaryl chloride (1 eq) in dioxane (1.0 mL/mmol II) was added. After 5 minutes, the mixture was placed in a microwave and heated at 180° C. for 30 minutes. The solvent was then filtered through a pad of magnesium sulfate, rinsing with CH$_2$Cl$_2$. The filtrate was concentrated to provide an orange solid. The solid was redissolved in CH$_2$Cl$_2$ and the resulting solution was washed with saturated aqueous NaHCO$_3$ followed by brine. The combined aqueous layers were extracted twice with CH$_2$Cl$_2$ and once with EtOAc. The combined organic layers were dried over MgSO$_4$, concentrated, and the crude residue was purified by flash chromatography on silica gel (gradient: 0 to 40% methanol/CH$_2$Cl$_2$).

Intermediate 13

4-{4-[4-((R)-3-Morpholin-4-yl-1-phenylsulfanylmethyl-propylamino)-3-trifluoromethanesulfonyl-benzenesulfonylamino]-5,8-dihydro-6H-pyrido[3,4d]pyrimidin-7-yl}-piperidine-1-carboxylic acid tert-butyl ester

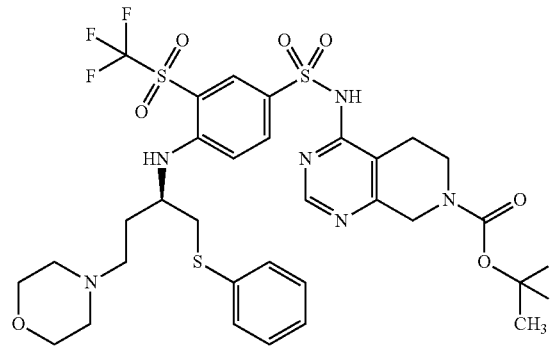

Following the general procedure, 4-((R)-3-morpholin-4-yl-1-phenylsulfanylmethyl-propylamino)-3-trifluoromethanesulfonyl-benzenesulfonamide (616 mg, 1.1 mmol) and 4-chloro-5,8-dihydro-6H-pyrido[3,4-d]pyrimidine-7-carboxylic acid tert-butyl ester (300 mg, 1.1 mmol) afforded the title compound (600 mg, 68% yield). MS (ESI) m/e (M+H$^+$): 787.4

Intermediates 14-18 listed below were prepared by cross-coupling of sulfonamides II with heteroaryl chlorides III following the general procedure described above.

Intermediate 14

(R)-tert-butyl 4-(4-(4-(dimethylamino)-1-(phenylthio)butan-2-ylamino)-3-(trifluoromethylsulfonyl) phenylsulfonamido)-5,6-dihydropyrido[3,4-d]pyrimidine-7(8H)-carboxylate

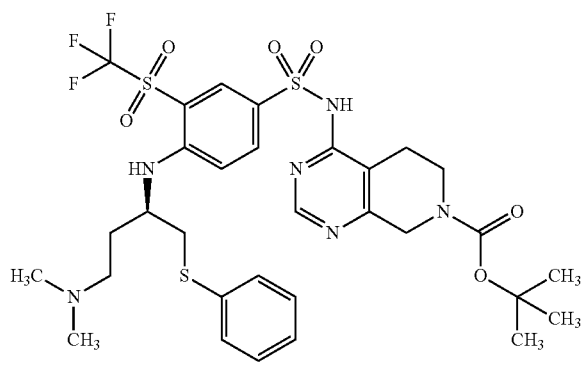 [SMILES: CN(C)CC[C@H](CSc1ccccc1)Nc1ccc(S(=O)(=O)Nc2ncnc3c2CCN(C(=O)OC(C)(C)C)C3)cc1S(=O)(=O)C(F)(F)F]

MS [m/z; M+1]=745

Intermediate 15

(R)-tert-butyl 4-(4-(4-(dimethylamino)-1-(phenylthio)butan-2-ylamino)-3-nitrophenylsulfonamido)-5,6-dihydropyrido[3,4-d]pyrimidine-7(8H)-carboxylate

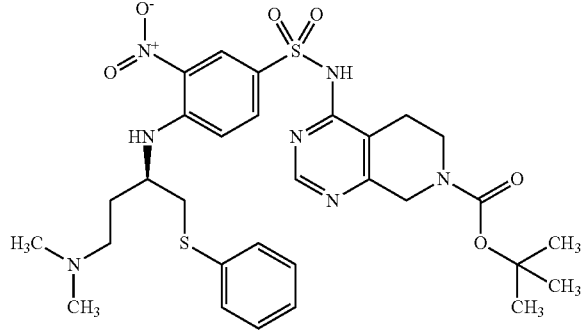 [SMILES: CN(C)CC[C@H](CSc1ccccc1)Nc1ccc(S(=O)(=O)Nc2ncnc3c2CCN(C(=O)OC(C)(C)C)C3)cc1[N+](=O)[O-]]

MS [m/z; M+1]=658

Intermediate 16

(R)-tert-butyl 4-(4-(4-(dimethylamino)-1-(phenylthio)butan-2-ylamino)-3-(trifluoromethylsulfonyl)phenylsulfonamido)-2-(trifluoromethyl)-5,6-dihydropyrido[3,4-d]pyrimidine-7(8H)-carboxylate

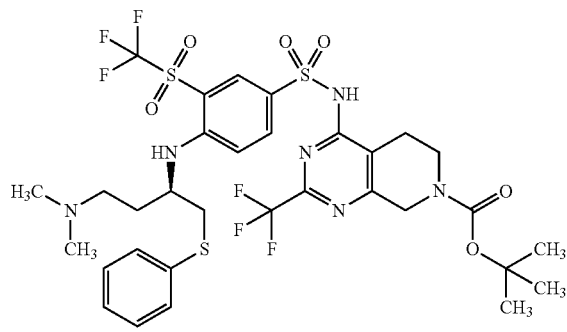 [SMILES: CN(C)CC[C@H](CSc1ccccc1)Nc1ccc(S(=O)(=O)Nc2nc(C(F)(F)F)nc3c2CCN(C(=O)OC(C)(C)C)C3)cc1S(=O)(=O)C(F)(F)F]

MS [m/z; M+1]=813

Intermediate 17

(R)-tert-butyl 4-(4-(4-morpholino-1-(phenylthio)butan-2-ylamino)-3-(trifluoromethylsulfonyl)phenyl sulfonamido)-2-(trifluoromethyl)-5,6-dihydropyrido[3,4-d]pyrimidine-7(8H)-carboxylate

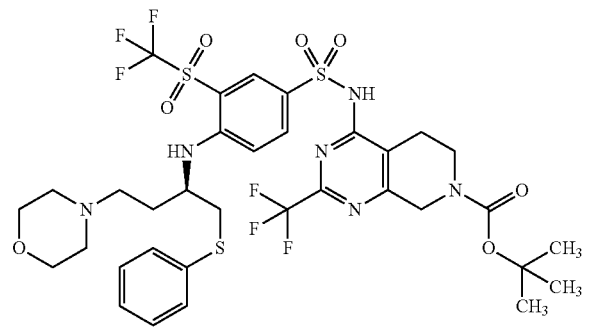 [SMILES: CC(C)(C)OC(=O)N1CCc2c(nc(C(F)(F)F)nc2NS(=O)(=O)c2ccc(N[C@H](CCN3CCOCC3)CSc3ccccc3)c(S(=O)(=O)C(F)(F)F)c2)C1]

MS [m/z; M+1]=855.

Intermediate 18

(R)-tert-butyl 4-(4-(4-(dimethylamino)-1-(phenylthio)butan-2-ylamino)-3-nitrophenylsulfonamido)-2-(trifluoromethyl)-5,6-dihydropyrido[3,4-d]pyrimidine-7(8H)-carboxylate

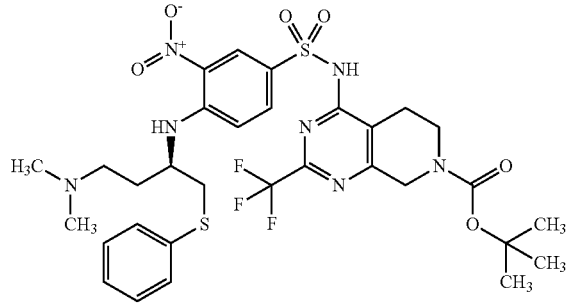 [SMILES: CN(C)CC[C@H](CSc1ccccc1)Nc1ccc(S(=O)(=O)Nc2nc(C(F)(F)F)nc3c2CCN(C(=O)OC(C)(C)C)C3)cc1[N+](=O)[O-]]

MS [m/z; M+1]=727.

Intermediate 19

3-[4-((R)-3-Morpholin-4-yl-1-phenylsulfanylmethyl-propylamino)-3-trifluoromethanesulfonyl-benzenesulfonylamino]-5,6-dihydro-8H-[1,2,4]triazolo[4,3-a]pyrazine-7-carboxylic acid tert-butyl ester

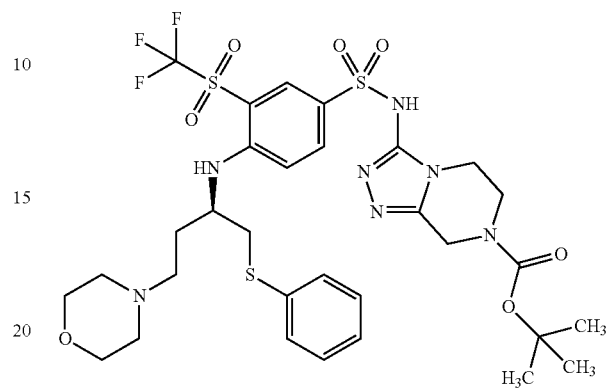

3-Bromo-5,6-dihydro-8H-[1,2,4]triazolo[4,3-a]pyrazine-7-carboxylic acid tert-butyl ester (54.8 mg, 0.181 mmol), 44(R)-3-morpholin-4-yl-1-phenylsulfanyl-methyl-propylamino)-3-trifluoromethanesulfonyl-benzenesulfonamide (100 mg, 0.181 mmol), (1S,2S)—N,N'-dimethyl-cyclohexane-1,2-diamine (07.71 mg, 0.054 mmol), cesium carbonate (100 mg, 0.307 mmol), and copper (I) iodide (5.16 mg, 0.027 mmol) were added to a microwave vial followed by toluene (2 mL). The reaction mixture was degassed for 15 minutes under nitrogen and then heated to 90° C. for 14 hours. The crude material was directly purified via flash chromatography on silica gel (0-25% 7 N ammonia in methanol in CH$_2$Cl$_2$) to afford the title compound (130 mg, 92% yield). MS [m/z; (M+1)$^+$]: 776.5

Intermediate 20

3-[4-((R)-3-Morpholin-4-yl-1-phenylsulfanylmethyl-propylamino)-3-trifluoromethanesulfonyl-benzenesulfonylamino]-4,5,7,8-tetrahydro-1,2,3a,6-tetraaza-azulene-6-carboxylic acid tert-butyl ester

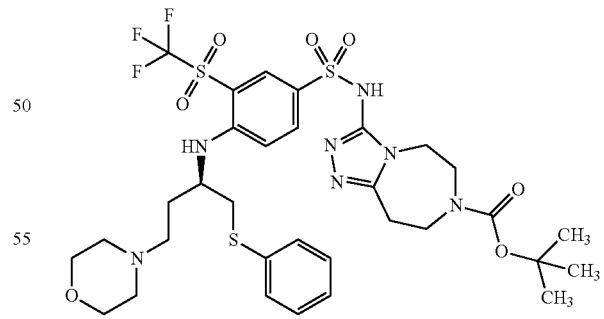

3-Bromo-4,5,7,8-tetrahydro-1,2,3a,6-tetraaza-azulene-6-carboxylic acid tert-butyl ester (154 mg, 0.486 mmol), 4-((R)-3-morpholin-4-yl-1-phenylsulfanylmethyl-propylamino)-3-trifluoromethane sulfonyl-benzenesulfonamide (269 mg, 0.486 mmol), (1S,2S)—N,N'-dimethyl-cyclohexane-1,2-diamine (0.011 mL, 0.146 mmol), cesium carbonate (269 mg, 0.825 mmol), and copper (I) iodide (13.87 mg, 0.073 mmol) were added to a microwave vial followed by toluene (8 mL). The reaction mixture was degassed for 15 minutes under nitrogen, sealed, and then heated conventionally to 90° C. for 14 hours. The crude material was directly purified via flash chromatography on silica gel (0-15% 2N $NH_3$ in methanol in $CH_2Cl_2$) to afford the title compound (170 mg, 44% yield). MS [m/z; (M+1)$^+$]: 790.5

Intermediate 21

(R)-tert-Butyl 4-(4-(4-morpholino-1-(phenylthio) butan-2-ylamino)-3-(trifluoromethylsulfonyl)phenylsulfonamido)-5H-pyrrolo[3,4-d]pyrimidine-6(7H)-carboxylate

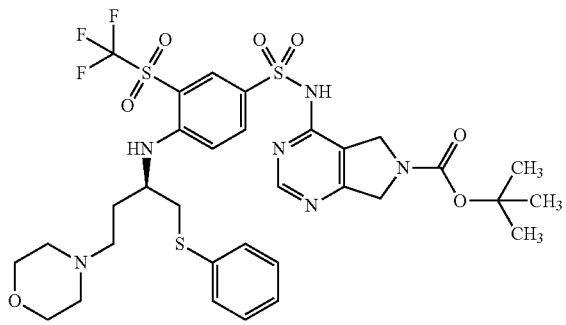 [SMILES: CC(C)(C)OC(=O)N1Cc2ncnc(NS(=O)(=O)c3ccc(N[C@H](CCN4CCOCC4)CSc4ccccc4)c(S(=O)(=O)C(F)(F)F)c3)c2C1]

STEP A: tert-Butyl 4-hydroxy-5H-pyrrolo[3,4-d]pyrimidine-6(7H)-carboxylate (300 mg, 1.264 mmol) and (1H-benzo[d][1,2,3]triazol-1-yloxy)tris(dimethylamino)0phosphonium hexafluorophosphate(V) (671 mg, 1.517 mmol) were stirred in acetonitrile (10 mL). To the slurry was added 2,3,4,6,7,8,9,10-octahydropyrimido-[1,2-a]azepine (289 mg, 1.897 mmol). The reaction mixture was stirred 1.5 hours. The solvents were removed in vacuo to afford tert-butyl 4-(1H-benzo[d][1,2,3]triazol-1-yloxy)-5H-pyrrolo[3,4-d]pyrimidine-6(7H)-carboxylate which was carried on to the next step without further purification.

STEP B: tert-Butyl 4-(1H-benzo[d][1,2,3]triazol-1-yloxy)-5H-pyrrolo[3,4-d]pyrimidine-6(7H)-carboxylate (448 mg, 1.264 mmol), (R)-4-(4-morpholino-1-(phenylthio)butan-2-ylamino)-3(trifluoromethylsulfonyl)benzenesulfonamide (910 mg, 1.643 mmol), and potassium carbonate (524 mg, 3.79 mmol) were combined in N,N-dimethylformamide (6.3 mL) and stirred for 1.5 hours at 85° C. and then for 2.5 hours at 95° C. The reaction was then cooled to room temperature and stirred for 16 hours. The reaction was treated with water (~30 mL) and sonicated. A dark brown solid stuck to the flask. The solid was washed several times with water and then several times with diethyl ether. This residue was then treated with methanol (~15 mL), and the off-white precipitate formed was removed by filtration. The dark brown filtrate was concentrated in vacuo to afford a brown solid. The water and ether washes were combined and diluted with more water and ether. The layers were separated, and the organic layer was dried over sodium sulfate, filtered and concentrated down. This residue was combined with the brown solid and purified by flash chromatography on silica gel (0 to 10% methanol/ethyl acetate followed by 0 to 30% methanol/dichloromethane) to afford the title compound (199 mg, 13% yield). MS (ESI) m/e (M+H)$^+$=773.5.

General Procedure for Removal of the Boc Protecting Group from Amines IV

IV

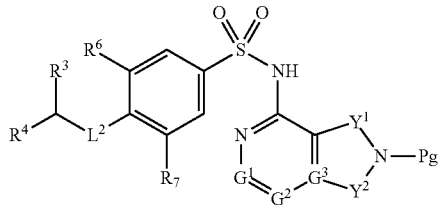

Amine (1 eq) was dissolved in $CH_2Cl_2$ (5 mL/mmol) and the flask was cooled to 0° C. Hydrochloric acid (2N in diethyl ether, 4 eq) was added slowly, and the reaction mixture was then stirred for 3 hours at room temperature. The solvent was removed in vacuo, and $CH_2Cl_2$ (20 mL) was added to the residue. The resulting solution was washed with saturated aqueous $NaHCO_3$ and brine. The combined aqueous layers were extracted twice with $CH_2Cl_2$ and once with EtOAc. The organic layers were combined, dried over $MgSO_4$, and concentrated. No additional purification was performed.

Intermediate 22

(R)-4-(4-Morpholino-1-(phenylthio)butan-2-ylamino)-N-(5,6,7,8-tetrahydropyrido[3,4-d]pyrimidin-4-yl)-3-(trifluoromethylsulfonyl)-benzenesulfonamide

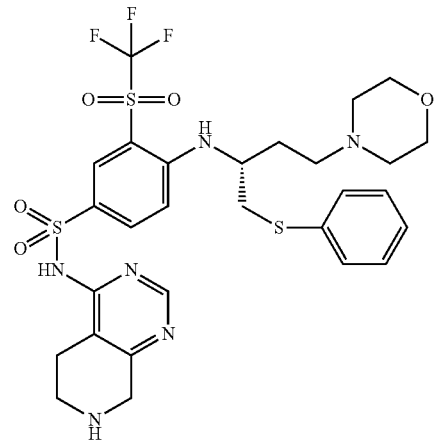 [SMILES: O=S(=O)(Nc1ncnc2c1CCNC2)c1ccc(N[C@H](CCN2CCOCC2)CSc2ccccc2)c(S(=O)(=O)C(F)(F)F)c1]

Following the general procedure, 4-{4-[4-((R)-3-Morpholin-4-yl-1-phenylsulfanylmethyl-propylamino)-3-trifluoromethanesulfonyl-benzene-sulfonylamino]-5,8-dihydro-6H-pyrido[3,4-d]pyrimidin-7-yl}-piperidine-1-carboxylic acid tert-butyl ester (300 mg, 0.38 mmol) afforded the title compound (170 mg, 50%). MS (ESI) in/e (M+H$^+$): 687.3

Intermediates 23-28 were prepared by deprotection of amines IV following the general procedure described above.

Intermediate 23

(R)-4-(4-(dimethylamino)-1-(phenylthio)butan-2-ylamino)-N-(5,6,7,8-tetrahydropyrido[3,4-d]pyrimidin-4-yl)-3-(trifluoromethyl sulfonyl)-benzenesulfonamide

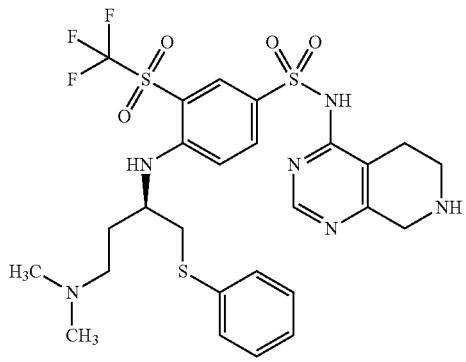 [SMILES: CN(C)CC[C@H](CSc1ccccc1)Nc1ccc(S(=O)(=O)Nc2ncnc3c2CCNC3)cc1S(=O)(=O)C(F)(F)F]

MS [m/z; M+1]=645.

Intermediate 24

(R)-4-(4-(dimethylamino)-1-(phenylthio)butan-2-ylamino)-3-nitro-N-(5,6,7,8-tetrahydropyrido[3,4-d]pyrimidin-4-yl)benzenesulfonamide

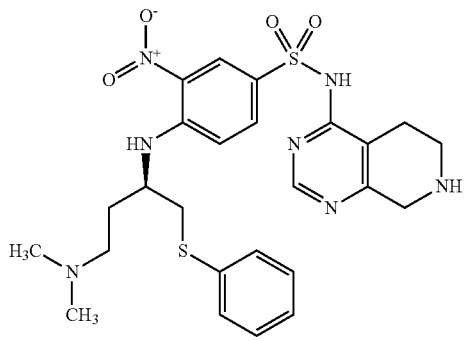 [SMILES: CN(C)CC[C@H](CSc1ccccc1)Nc1ccc(S(=O)(=O)Nc2ncnc3c2CCNC3)cc1[N+](=O)[O-]]

MS [m/z; M+1]=558.

Intermediate 25

(R)-4-(4-(dimethylamino)-1-(phenylthio)butan-2-ylamino)-N-(2-(trifluoromethyl)-5,6,7,8-tetrahydropyrido[3,4-d]pyrimidin-4-yl)-3-(trifluoromethylsulfonyl)benzenesulfonamide

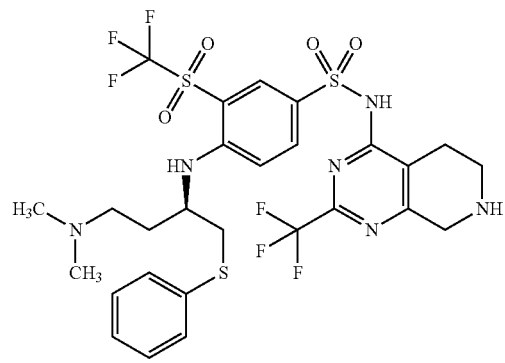 [SMILES: CN(C)CC[C@H](CSc1ccccc1)Nc1ccc(S(=O)(=O)Nc2nc(C(F)(F)F)nc3c2CCNC3)cc1S(=O)(=O)C(F)(F)F]

MS [m/z; M+1]=713.

Intermediate 26

(R)-4-(4-morpholino-1-(phenylthio)butan-2-ylamino)-N-(2-(trifluoromethyl)-5,6,7,8-tetrahydropyrido[3,4-d]pyrimidin-4-yl)-3-(trifluoromethylsulfonyl)benzenesulfonamide

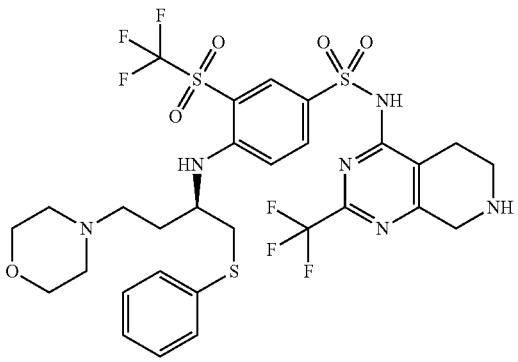 [SMILES: O=S(=O)(Nc1nc(C(F)(F)F)nc2c1CCNC2)c1ccc(N[C@H](CCN2CCOCC2)CSc2ccccc2)c(S(=O)(=O)C(F)(F)F)c1]

MS [m/z; M+1]=755.

Intermediate 27

(R)-4-(4-(dimethylamino)-1-(phenylthio)butan-2-ylamino)-3-nitro-N-(2-(trifluoromethyl)-5,6,7,8-tetrahydropyrido[3,4-d]pyrimidin-4-yl)-benzenesulfonamide

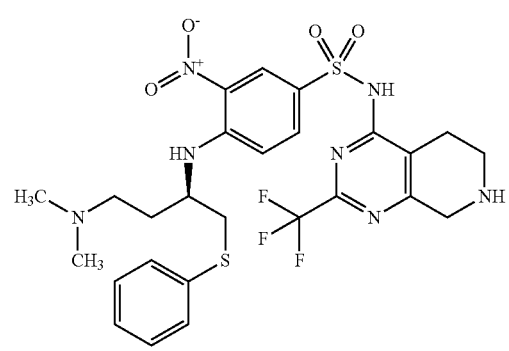 [SMILES: CN(C)CC[C@H](CSc1ccccc1)Nc1ccc(S(=O)(=O)Nc2nc(C(F)(F)F)nc3c2CCNC3)cc1[N+](=O)[O-]]

MS [m/z; M+1]=627.

Intermediate 28

(R)-N-(6,7-dihydro-5H-pyrrolo[3,4-d]pyrimidin-4-yl)-4-(4-morpholino-1-(phenylthio)butan-2-ylamino)-3-(trifluoromethylsulfonyl)-benzenesulfonamide

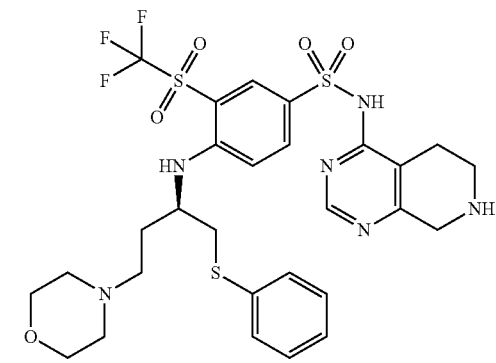 [SMILES: O=S(=O)(Nc1ncnc2c1CCNC2)c1ccc(N[C@H](CCN2CCOCC2)CSc2ccccc2)c(S(=O)(=O)C(F)(F)F)c1]

MS [m/z; M+1]=673.

Intermediate 29

4-((R)-3-Morpholin-4-yl-1-phenylsulfanylmethyl-propylamino)-N-(5,6,1,8-tetrahydro[1,2,4]triazolo[4,3-a]pyrazin-3-yl)-3-trifluoromethanesulfonyl-benzenesulfonamide

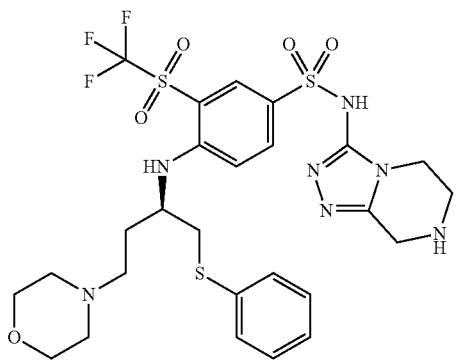 [SMILES: O=S(=O)(Nc1nnc2n1CCNC2)c1ccc(N[C@H](CCN2CCOCC2)CSc2ccccc2)c(S(=O)(=O)C(F)(F)F)c1]

To a solution of 3-[4-((R)-3-morpholin-4-yl-1-phenylsulfanylmethyl-propylamino)-3-trifluoromethanesulfonyl-benzenesulfonylamino]-5,6-dihydro-8H-[1,2,4]triazolo[4,3-a]pyrazine-7-carboxylic acid tert-butyl ester (130 mg, 0.168 mmol) in dichloromethane (3 mL) under nitrogen was added trifluoroacetic acid (0.323 mL, 4.19 mmol), and the reaction was stirred for 2.5 hours. The reaction mixture was then concentrated and diluted with water and CH$_2$Cl$_2$. It was then basified to pH approximately 8 with saturated Na$_2$CO$_3$. The organics were extracted three times with CH$_2$Cl$_2$. The combined organic layers were washed with brine, dried over Na$_2$SO$_4$, filtered and concentrated under reduced pressure to afford the title compound (112 mg, 99% yield). MS [m/z; (M+1)$^+$]: 676.5

Intermediate 30

4-((R)-3-Morpholin-4-yl-1-phenylsulfanylmethyl-propylamino)-N-(5,6,7,8-tetrahydro-4H-1,2,3a,6-tetraaza-azulen-3-yl)-3-trifluoromethanesulfonyl-benzensulfonamide

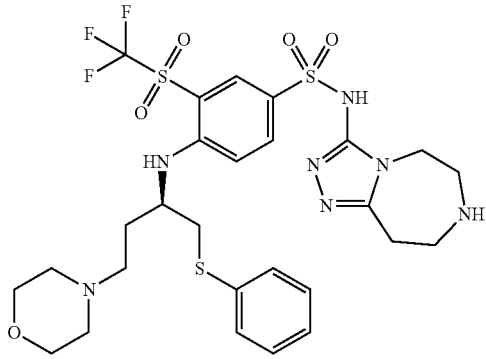 [SMILES: O=S(=O)(Nc1nnc2n1CCNCC2)c1ccc(N[C@H](CCN2CCOCC2)CSc2ccccc2)c(S(=O)(=O)C(F)(F)F)c1]

To a solution of 3-[4(R)-3-morpholin-4-yl-1-phenylsulfanylmethyl-propylamino)-3 trifluoromethanesulfonyl-benzenesulfonylamino]-4,5,7,8-tetrahydro-1,2,3a,6-tetraaza-azulene-6-carboxylic acid tert-butyl ester (170 mg, 0.215 mmol) in dichloromethane (4 mL) under nitrogen was added trifluoroacetic acid (0.415 mL, 5.38 mmol), and the reaction was stirred for 2 hours. The reaction mixture was concentrated and diluted with water and dichloromethane. It was then basified to pH approximately 8 with saturated Na$_2$CO$_3$. The aqueous layer was extracted three times with dichloromethane. The combined organic layers were washed with brine, dried over Na$_2$SO$_4$, filtered and concentrated under reduced pressure to afford the title compound (155 mg, 100% yield). MS [m/z; (M+1)$^+$]: 690.4

Synthesis of Types XIII and IX Intermediates

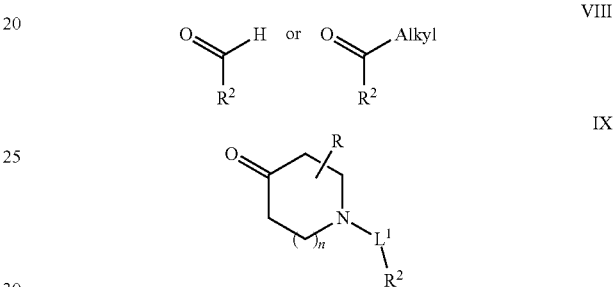

Intermediate 31

4'-Chloro-biphenyl-2-carbaldehyde

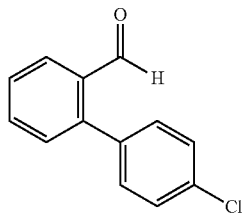 [SMILES: O=Cc1ccccc1-c1ccc(Cl)cc1]

To a solution of 2-bromobenzaldehyde (18.0 g, 97.0 mmol) and 4-chloro-phenylboronic acid (19.0 g, 122 mmol) in a 1:1 mixture of ethanol/DME (400 mL) is added a solution of potassium carbonate (26.9 g, 195 mmol) in water (100 mL), and the reaction mixture is purged with nitrogen for 30 minutes. Tetrakis(triphenyl-phosphine)palladium (5.62 g, 4.86 mmol) is then added, and the reaction is purged again with nitrogen for 20 minutes. The pale yellow-green solution is heated to 75° C. and stirred for 20 hours. The reaction is then cooled to room temperature, diluted with ethyl acetate (200 mL), and filtered through a ZAPCAP filter. The filtrate is washed with brine (400 mL) and the aqueous layer is back-extracted with ethyl acetate (2×200 mL). The combined organic layers are dried over MgSO$_4$ and concentrated to afford an orange oily solid. This crude material is purified via flash chromatography on silica gel (0-20% EtOAd heptanes) to afford the title compound (14.9 g, 71% yield). $^1$H NMR (400 MHz, CDCl$_3$) δ 10.0 (s, 1H), 8.05 (d, J=7.5 Hz, 1H), 7.68 (t, J=6.2 Hz, 1H), 7.54 (t, J=7.4 Hz, 1H), 7.49 (d, J=9.4 Hz, 2H), 7.45 (d, J=9.1 Hz, 1H), 7.34 (d, J=8.5 Hz, 2H).

Intermediate 32

4'-Chloro-2-(iodomethyl)biphenyl

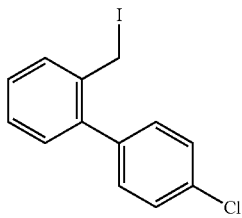 [SMILES: Clc1ccc(-c2ccccc2CI)cc1]

STEP A: 4'-Chloro-biphenyl-2-carbaldehyde (6.50 g, 30.0 mmol) was dissolved in CH$_2$Cl$_2$ (75 mL) and methanol (75 mL). The solution was cooled to 0° C. in an ice bath, and then sodium borohydride (1.36 g, 36.0 mmol) was added slowly portionwise. The reaction was allowed to warm gradually to room temperature and stir for 16 hours. The reaction was quenched by addition of 2M NaOH, and the organics were extracted with CH$_2$Cl$_2$ (3×75 mL). The combined organic layers were dried over MgSO$_4$ and concentrated to afford (4'-chloro-biphenyl-2-yl)-methanol (6.42 g, 98% yield), which was carried on to the next step without further purification. MS (ES1) m/e (M−H)$^-$: 217.4

STEP B: Triphenylphosphine (8.47 g, 32.3 mmol), iodine (8.94 g, 35.2 mmol), imidazole (2.40 g, 352 mmol), and CH$_2$Cl$_2$ (110 mL) were combined in a round-bottom flask, and the mixture was stirred for 15 minutes. A solution of (4'-chloro-biphenyl-2-yl)-methanol in CH$_2$Cl$_2$ (40 mL) was then added, and the reaction was stirred at room temperature for 16 hours (flask was wrapped in aluminum foil to shield it from the light). A saturated aqueous Na$_2$S$_2$O$_2$ was added. The layers were separated, and the aqueous layer was extracted with CH$_2$Cl$_2$ (2×100 mL). The organic layers were combined, dried over MgSO$_4$, and concentrated. The crude residue was purified by flash chromatography on silica gel (0-10% EtOAc/heptanes) to afford the title compound as an off-white solid (5.33 g, 55% yield). $^1$H NMR (400 MHz, CDCl$_3$) δ ppm 7.51-7.53 (m, 1H), 7.38-7.46 (m, 4H), 7.28-7.37 (m, 2H); 7.15-7.17 (m, 1H).

Intermediate 33

1-(4'-Chloro-biphenyl-2-ylmethyl)-piperidin-4-one.

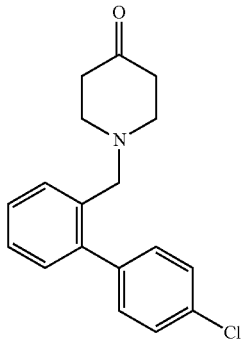 [SMILES: O=C1CCN(Cc2ccccc2-c2ccc(Cl)cc2)CC1]

STEP A: 4'-Chloro-biphenyl-2-carbaldehyde (5.00 g, 23.08 mmol) and 1,4-dioxa-8-azaspiro[4.5]decane (4.30 g, 30.0 mmol) were combined in DCE (90 mL) and methanol (68 mL). MgSO$_4$ (~5 g) was added, and the resulting mixture was stirred for 1 hour at room temperature. Sodium triacetoxyborohydride (14.67 g, 69.2 mmol) was then added, and the reaction was stirred for 16 hours at room temperature. The solvent was removed in vacuo, and the residue was resuspended in CH$_2$Cl$_2$/H$_2$O. The layers were separated, and the aqueous layer was extracted with CH$_2$Cl$_2$ (2×100 mL). The organic layers were combined, dried over MgSO$_4$, and concentrated. Flash chromatography on silica gel (0-10% NH$_3$ in methanol (~2M)/CH$_2$Cl$_2$) afforded 8-((4'-chlorobiphenyl-2-yl)methyl)-1,4-dioxa-8-azaspiro[4.5]decane as a brown oil (4.73 g, 60% yield). MS (ESI) m/e (M+H)$^+$: 344.5

STEP B: 8-((4'-Chlorobiphenyl-2-yl)methyl)-1,4-dioxa-8-azaspiro[4.5]decane (4.73 g, 13.76 mmol) was dissolved in dioxane (50 mL) and water (30 mL). Hydrochloric acid (37%, 14.3 mL, 174 mmol) was added, and the reaction was heated to 85° C. for 26 hours. After cooling to room temperature, the volatiles are removed in vacuo. The remaining aqueous phase is basified to pH ~9 with 2M NaOH, and then extracted with CH$_2$Cl$_2$. The organic layers are dried over MgSO$_4$ and concentrated to afford the title compound (4.13 g, 100% yield). MS (ESI) m/e (M+H)$^+$: 300.4

Intermediate 34

(S)-1-(4'-Chloro-biphenyl-2-ylmethyl)-2-methyl-piperidin-4-one

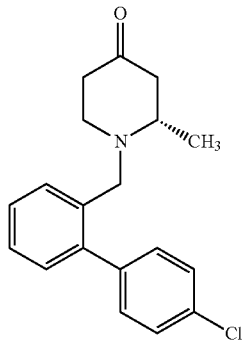 [SMILES: C[C@H]1CC(=O)CCN1Cc1ccccc1-c1ccc(Cl)cc1]

(S)-2-Methyl-piperidin-4-one hydrochloride (100 mg, 0.67 mmol) was combined with K$_2$CO$_3$ (554 mg, 4.0 mmol) in acetonitrile (5.0 mL) and stirred for 15 minutes. 4'-Chloro-2-(iodomethyl)biphenyl (220 mg, 0.668 mmol) was added, and the resulting mixture was heated to 70° C. and stirred for 16 hours. The reaction was cooled to room temperature, filtered, and concentrated. The crude residue was purified by flash chromatography on silica gel (heptanes/EtOAc gradient) to afford the title compound as an off-white solid (178 mg, 85% yield). MS (ESI) m/e (M+H$^+$): 313.8

Intermediate 35

1-(2-Bromo-benzyl)-piperidin-4-one

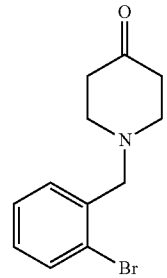 [SMILES: O=C1CCN(Cc2ccccc2Br)CC1]

According to the procedure described for Intermediate 31, alkylation of 4-piperidone hydrochloride (1.0 g, 4.0 mmol) with 1-bromo-2-bromomethylbenzene (543 mg, 4.0 mmol) afforded the title compound (882 mg, 82% yield). HR-MS (m/z, MH+): measured 268.15

Intermediate 36

1-(4'-Fluoro-biphenyl-2-ylmethyl)-piperidin-4-one

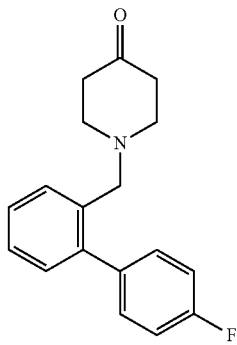 [SMILES: O=C1CCN(Cc2ccccc2-c2ccc(F)cc2)CC1]

To a 5 mL microwave vial equipped with a stir bar was added sodium carbonate (79 mg, 0.75 mmol). The vial was dried in an oven for 16 hours, then cooled to room temperature under nitrogen. 1-(2-Bromo-benzyl)-piperidin-4-one (100 mg, 0.37 mmol), 4-fluorophenyl boronic acid (52.2 mg, 0.37 mmol) and Pd(PPh$_3$)$_4$ (43 mg, 0.037 mmol) were added, followed by dioxane (5 mL) water (1 mL). The resulting mixture was degassed thoroughly with nitrogen and then heated in a microwave to 100° C. for 10 minutes. The reaction was filtered and the filtrate was concentrated. The crude residue was purified via flash chromatography (heptanes/EtOAc gradient) to afford the desired product as a yellow solid (58 mg, 40% yield). MS (ESI) ink (M+H$^+$): 283.3.

Intermediate 37

1-[2-(4-Chloro-phenyl)-5,5-dimethyl-cyclohex-1-enylmethyl]-piperidin-4-one

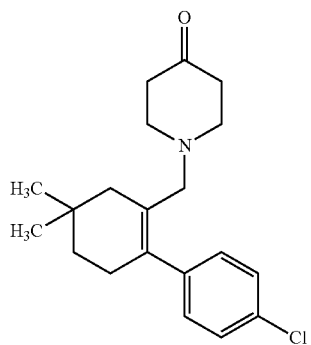 [SMILES: CC1(C)CCC(c2ccc(Cl)cc2)=C(CN2CCC(=O)CC2)C1]

STEP A: A suspension of 2-bromo-5,5-dimethylcyclohex-1-enecarbaldehyde (250 mg, 1.15 mmol), 4-chlorophenyl boronic acid (270 mg, 1.727 mmol) and Pd(Ph$_3$P)$_4$ (66.5 mg, 0.058 mmol) in dioxane (2.5 mL) was stirred at room temperature in a 5 mL microwave vial under an atmosphere of nitrogen. A solution of potassium carbonate (318 mg, 2.3 mmol) in water (0.3 mL) was added and the solution became clear. The vial was capped and heated to 100° C. for 12 minutes in a microwave. The reaction was cooled to room temperature, diluted with CH$_2$Cl$_2$, filtered through a plug of Celite, and concentrated. The crude residue was purified by flash chromatography on silica gel (0-25% EtOAc/heptanes) to afford 2-(4-chlorophenyl)-5,5-dimethylcyclohex-1-enecarbaldehyde as a clear colorless oil (220 mg, 77% yield).

STEP B: A suspension of the hydrochloride salt of 4-oxopiperidine (273 mg, 2.01 mmol) and DIPEA (351 μL, 2.01 mmol) was stirred in DCE (9.0 mL) at room temperature for 10 minutes. 2-(4-Chlorophenyl)-5,5-dimethylcyclohex-1-enecarbaldehyde (500 mg, 2.01 mmol) was then added, followed by NaBH(OAc)$_3$ (426 mg, 2.01 mmol) and activated molecular sieves (~1 g). The resulting suspension was stirred at room temperature for 16 hours. The reaction mixture was then filtered through a plug of Celite, rinsing with EtOAc. The filtrate was washed sequentially with saturated aqueous NaHCO$_3$, water, and brine. The organic layer was dried over MgSO$_4$ and concentrated. The crude residue was purified by flash chromatography on silica gel to afford the title compound (262 mg, 40% yield). MS (ESI) m/e (M+H$^+$): 331.88

Intermediate 38

1-((4'-Chlorobiphenyl-2-yl)methyl)-3-fluoropiperidin-4-one

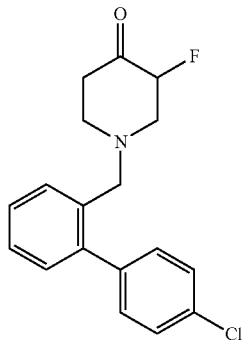 [SMILES: O=C1CCN(Cc2ccccc2-c2ccc(Cl)cc2)CC1F]

STEP A: 4-Oxo-piperidine-1-carboxylic acid tert-butyl ester (10.0 g, 501 mmol) was dissolved in DMF (20 mL). Chlorotrimethylsilane (6.6 g, 60.6 mmol) was added, followed by Et$_3$N (12.3 g, 122 mmol). The mixture was stirred at 80° C. for 16 hours, cooled to ambient temperature, diluted with Et$_2$O, and then washed with water, followed by brine. The organic layer was separated, dried over Na$_2$SO$_4$, filtered and concentrated. Purification by flash chromatography on silica gel (EtOAc/heptanes 0-50%) afforded 4-trimethylsilanyloxy-3,6-dihydro-2H-pyridine-1-carboxylic acid tert-butyl ester (4.3 g, 32% yield). $^1$H NMR (400 MHz, CHLOROFORM-d) δ ppm 4.80 (br. s., 1H), 3.88 (br. s., 2H), 3.53 (t, J=5.81 Hz, 2H), 2.11 (br. s., 2H), 1.49 (s, 9H), 0.20 (s, 9H).

STEP B: 4-Trimethylsilanyloxy-3,6-dihydro-2H-pyridine-1-carboxylic acid tert-butyl ester (0.60 g, 2.2 mmol) was dissolved in MeCN and Selectfluor (0.86 g, 2.4 mmol) is added. The reaction was stirred at ambient temperature for 75 minutes, and then poured into EtOAc (100 mL). The organics were washed with dilute brine and saturated brine, then dried (Na$_2$SO$_4$), filtered and concentrated. Purification by flash chromatography on silica gel (0-50% EtOAc/Hept) afforded 3-fluoro-4-oxo-piperidine-1-carboxylic acid tert-butyl ester (0.40 g, 83% yield). $^1$H NMR (400 MHz, CHLOROFORM-d) δ ppm 4.64-4.91 (m, 1H), 4.39 (d, 1H), 4.11 (td, J=6.57, 3.03 Hz, 1H), 3.10-3.24 (m, 2H), 2.40-2.61 (m, 2H), 1.43 (s, 9H).

STEP C: 3-Fluoro-4-oxo-piperidine-1-carboxylic acid tert-butyl ester (2.7 g, 12.4 mmol) was dissolved in dioxane/HCl (100 mL, 0.12 M) and stirred at ambient temperature for 2 hours. Volatiles were then removed in vacuo to afford 3-fluoro-piperidin-4-one as an HCl salt, which was carried on without further purification (1.7 g, 92% yield). $^1$H NMR (400 MHz, DMSO-d6) δ ppm 9.77 (br. s., 1H), 8.77 (br. s., 1H), 6.36 (br. s., 2H), 4.41-4.53 (d, J=48 Hz, 1H), 3.37 (t, J=9.85 Hz, 1H), 3.21 (m, 1H), 3.08 (m, 1H), 2.93 (m, 1H), 1.94 (m, 1H), 1.77 (m, 1H).

STEP D: 3-Fluoro-piperidin-4-one (0.32 g, 2.7 mmol) was dissolved in DMF (13 mL) and 4'-chloro-2-(iodomethyl)biphenyl (1.03 g, 3.13 mmol) was added followed by DIPEA (1.06 g, 8.2 mmol). The reaction was stirred at ambient temperature for 16 hours, and then poured into EtOAc (100 mL). The organics were washed with water followed by brine, dried (Na$_2$SO$_4$), filtered and concentrated. Purification by flash chromatography on silica gel afforded the title compound (0.75 g, 86% yield). $^1$H NMR (400 MHz, CDCl$_3$) δ ppm 7.47-7.59 (m, 1H), 7.21-7.47 (m, 7H), 4.72-5.00 (m, 1H), 3.62-3.65 (d, J=12 Hz, 1H), 3.56-3.59 (d, J=12 Hz, 1H), 3.25-3.42 (m, 1H), 2.88-3.06 (m, 1H), 2.28-2.63 (m, 4H).

Intermediate 39

1-[1-(4'-Chloro-biphenyl-2-yl)-ethyl]-piperidin-4-one

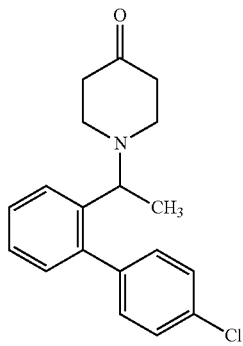 [SMILES: CC(c1ccccc1-c1ccc(Cl)cc1)N1CCC(=O)CC1]

Step A: Same experimentals as intermediate 31 substituting 1-(2-Bromo-phenyl)-ethanone to afford 1-(4'-Chloro-biphenyl-2-yl)-ethanone (1.31 g, 74%). $^1$H NMR (400 MHz, CDCl$_3$) δ 7.57 (dd, 1H, J=7.6, 1.0 Hz), 7.54 (m, 1H), 7.46 (m, 1H), 7.43 (2H, d, J=8.6 Hz), 739 (1H, dd, J=7.6, 1.0 Hz), 7.30 (2H, d, J=8.6 Hz), 2.11 (3H, s).

Step B: To a mixture of 1-(4'-Chloro-biphenyl-2-yl)-ethanone (2.42 g, 10.5 mmol) and 4-piperidone ethylene ketal (1.50 g, 10.5 mmol) and titanium (IV) isopropoxide (5.96 g, 21.0 mmol) is heated up to 75° C. for 3 hours. The reaction is then cooled to room temperature and is added 50 mL of ethanol followed by sodium borohydride (1.19 g, 31.5 mmol) the reaction is then stirred for 18 hours at room temperature and then quench with 50 mL of methanol. The crude reaction is then dissolved in ethyl acetate and then washed with a saturated solution of sodium bicarbonate. The aqueous layer is then extracted 2 times with ethyl acetate. The combined organic layer are then dried on MgSO$_4$ and the solvent is removed under vacuum. The residue is chromatographed on silica gel gel (gradient: heptane/EtOAc; 0 to 60% EtOAc over 15 minutes) to afford 8-[1-(4'-Chloro-biphenyl-2-yl)-ethyl]-1,4-dioxa-8-aza-spiro[4.5]decane (3.6 g, 96%). Found m/z ES+=358.5 (M+H); $^1$H NMR (400 MHz, CD$_2$Cl$_2$) δ 7.64 (1H, d, J=8.1 Hz), 7.41 (2H, d, J=8.6 Hz), 7.40 (1H, t), 7.30 (2H, J=8.6 Hz), 7.29 (1H, t), 7.18 (1H, d, J=7.6 Hz), 3.90 (4H, s), 3.51 (1H, m), 2.48 (2H, m), 2.36 (2H, m), 1.62 (4H, m), 1.27 (3H, d, J=6.6 Hz).

Step C: To a solution of 8-[1-(4'-Chloro-biphenyl-2-yl)-ethyl]-1,4-dioxa-8-aza-spiro[4.5]decane (3.1 g, 8.66 mmol) in dioxane-water (1:1 60 mL) is added HCl 37% (10.5 mL, 346 mmol). The reaction is then heated up to 85° C. for 26 hours. The solvent is then removed under vacuum and the aqueous phase is basified to pH=9 using sodium hydroxide 4N and then extracted with DCM. The organic layer is then washed with brine. The combined organic phase is then dried on MgSO$_4$ and concentrated to afford 1-[1-(4'-Chloro-biphenyl-2-yl)-ethyl]-piperidin-4-one. The crude material is used without further purification. Found m/z ES+=314.2 (M+H); $^1$H NMR (400 MHz, CDCl$_3$) δ 7.57 (1H, d, J=7.1 Hz), 7.32 (1H, t), 7.30 (2H, d, J=8.6 Hz), 7.22 (1H, t), 7.15 (2H, d, J=8.6 Hz), 7.09 (1H, d, J=6.1 Hz), 3.58 (1H, m), 2.63 (2H, m), 2.52 (2H, m), 2.25 (4H, t, J=6.1 Hz), 1.24 (3H, d, J=6.6 Hz).

Intermediate 40

4-Benzylidenecyclohexanone

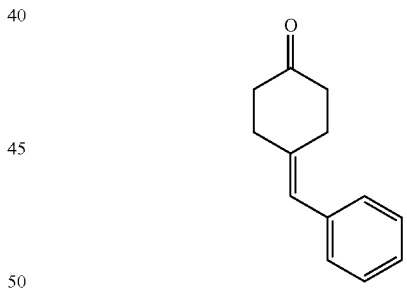

To a solution of 8-benzylidene-1,4-dioxaspiro[4.5]decane (5.79 g, 25.1 mmol) in THF (126 mL) a solution of H$_2$SO$_4$ (10% in water, 67 mL) was added and the result mixture was stirred at room temperature for 3 days. THF was removed under reduce pressure and water was added. The aqueous phase was extracted with DCM and the organic layers were combined, washed with brine, dried with Na$_2$SO$_4$, filtered and concentrated to give 4-Benzylidenecyclohexanone (4.35 g 84%) as a yellowish oil: $^1$H NMR (400 MHz, CHLOROFORM-d) δ ppm 7.23-7.33 (m, 2 H), 7.13-7.20 (m, 3 H), 6.42 (s, 1 H), 2.67-2.77 (m, 2 H), 2.62 (t, J=7.0 Hz, 2 H), 2.46 (t, J=7.0 Hz, 2 H), 2.37 (t, J=7.0 Hz, 2 H).

Intermediate 41

4-((4'-Chlorobiphenyl-2-yl)methylene)cyclohexanone

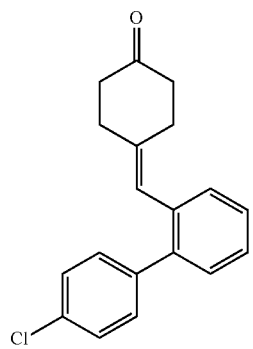 [SMILES: O=C1CCC(=Cc2ccccc2-c2ccc(Cl)cc2)CC1]

Step A: To a solution of 4'-chloro-2-(iodomethyl)biphenyl in toluene (11 mL), triphenylphosphine (1.20 g, 4.57 mmol) was added. The result mixture was refluxed overnight, allowed to cool to room temperature and filtered. The solid was washed with ether and dried under vacuum to afford ((4'-Chlorobiphenyl-2-yl)methyl)triphenylphosphonium iodide (2.50 g, 93%): $^1$H NMR (400 MHz, chloroform-d) δ ppm 6.35-8.06 (m, 23 H), 5.12-5.63 (m, 2 H).

Step B: A suspension of sodium hydride (60% in mineral oil, 77 mg, 1.92 mmol) in DMSO (5.8 mL) was heated for 1 hour at 80° C. and then cooled to rt. ((4'-Chlorobiphenyl-2-yl)methyl)triphenylphosphonium iodide (1.04 g, 1.76 mmol) was added to the suspension and then, after stirring 10 minutes at room temperature, 1,4-cyclohexanedione monoethylene acetal (0.25 g, 1.60 mmol) was added. The reaction mixture was heated at 80° C. for 3 hours. After standing at rt overnight, the reaction mixture was poured into a saturated solution of NaHSO$_4$ and extracted with EtOAc. The organic layers were combined, washed with brine, dried with Na$_2$SO$_4$, filtered and concentrated. The crude was purified by flash chromatography (silica gel, 0% to 30% EtOAc in heptane) to give ((4'-Chlorobiphenyl-2-yl)methylene)-1,4dioxaspiro[4.5]decane (0.28 g, 52%) as a white solid: $^1$H NMR (400 MHz, CHLOROFORM-d) δ ppm 7.12-7.33 (m, 8 H), 5.98 (s, 1 H), 3.92 (s, 4 H), 2.30-2.36 (m, 2 H), 2.22-2.29 (m, 2 H), 1.62-1.71 (m, 2 H), 1.52-1.58 (m, 2 H).

Step C: To a solution of the ketal ((4"-Chlorobiphenyl-2-yl)methylene)-1,4dioxaspiro[4.5]decane (180 mg, 0.53 mmol) in a mixture of dioxane (3 mL) and water (2.3 mL) a solution of aqueous HCl (12 M, 0.80 ml, 9.6 mmol) was added. The result mixture was heated to 80° C. and stirred overnight. THF was removed under reduce pressure and water was added. The aqueous phase was extracted with EtOAc and the organic layers were combined, washed with brine, dried with Na$_2$SO$_4$, filtered and concentrated to afford 4((4'-Chlorobiphenyl-2-yl)methylene)cyclohexanone (157 mg, 100%) of the pure ketone as a colorless oil: $^1$H NMR (400 MHz, CHLOROFORM-d) δ ppm 7.16-7.32 (m, 8 H), 6.21 (s, 1 H), 2.43-2.51 (m, 4 H), 2.35 (t, J=7.0 Hz, 2 H), 2.17 (t, J=7.0 Hz, 2 H).

Examples 1-99

Synthesis of Examples 1-19 by Reductive Amination of Ketones IX with Amines V

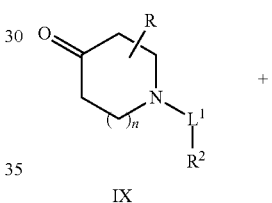

IX

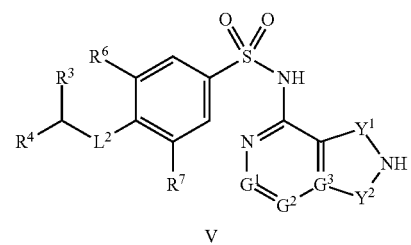

V

General Reductive Amination Procedure 1

A solution of amine V (1 eq), ketone IX (1 eq), acetic acid (0.2 eq), and powdered molecular sieves (approximately 330 mg/mmol V) in 1:1 CH$_2$Cl$_2$:methanol (6 mL) was stirred at 0° C. for 1 hour. Sodium cyanoborohydride (2 eq) was added, and the reaction was allowed to warm to room temperature and stir for 16 hours. The reaction was filtered, and the filtrate was concentrated in vacuo. The crude residue was purified by flash chromatography on silica gel (0-100% methanol in CH$_2$Cl$_2$).

Example 1

Preparation of N-{7-[1-(4'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-nitro-benzenesulfonamide

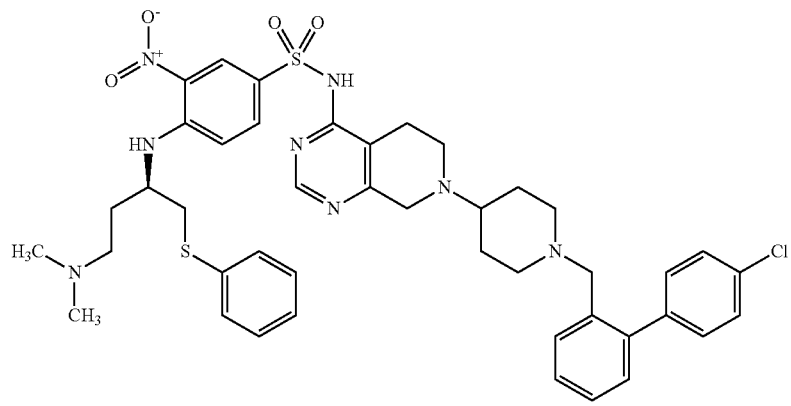 [SMILES: CN(C)CC[C@H](CSc1ccccc1)Nc1ccc(S(=O)(=O)Nc2ncnc3c2CCN(C2CCN(Cc4ccccc4-c4ccc(Cl)cc4)CC2)C3)cc1[N+](=O)[O-]]

Following General Reductive Amination Procedure 1,4-((R)-3-dimethylamino-1-phenylsulfanylmethyl-propylamino)-3-nitro-N-(5,6,7,8-tetrahydro-pyrido[3,4-d]pyrimidin-4-yl)-benzenesulfonamide (85 mg, 0.15 mmol) and 1-(4'-chloro-biphenyl-2-ylmethyl)-piperidin-4-one (453 mg, 0.15 mmol) afforded the title compound as a yellow solid (40 mg, 31% yield).

$^1$H NMR (400 MHz, MeOD) δ (ppm): 8.66 (d, J=2.01 Hz, 1H), 8.14 (s, 1H), 7.86 (dd, J=9.03, 2.01 Hz, 1H), 7.48 (d, J=7.03 Hz, 1H), 7.17-7.41 (m, 9H), 7.06-7.10 (m, 3H), 6.80 (d, J=9.03 Hz, 1H), 3.96-4.06 (m, 1H), 3.51 (s, 2H), 3.38 (s, 2H), 3.25-3.30 (m, 1H), 3.11-3.17 (dd, J=4.0, 16.0 Hz, 1H), 2.76-2.85 (m, 4H), 2.62-2.68 (m, 2H), 2.30-2.45 (m, 3H), 2.20 (s, 6H), 1.98-2.10 (m, 1H), 1.78-1.91 (m, 5H), 1.45-1.55 (m, 2H).

HR-MS (m/z, MH$^+$): 841.50

HPLC retention time=3.13 minutes (Agilent 1100 HPLC system; Inertsil ODS3 100×3 mm C18 column; flow rate of 1.0 mL/minute; gradient: 5-95% acetonitrile/water with 0.1% FA over 7.75 minutes).

Examples 2-7 were prepared by reductive amination of ketones IX with amines V following General Procedure 1 above.

Example 2

(R)-N-(7-(1-((2-(4-chlorophenyl)-5,5-dimethylcyclohex-1-enylmethyl)piperidin-4-yl)-5,6,7,8-tetrahydro-pyrido[3,4-d]pyrimidin-4-yl)-4-(4-(dimethylamino)-1-(Phenylthio)butan-2-ylamino)-3-nitrobenzenesulfonamide

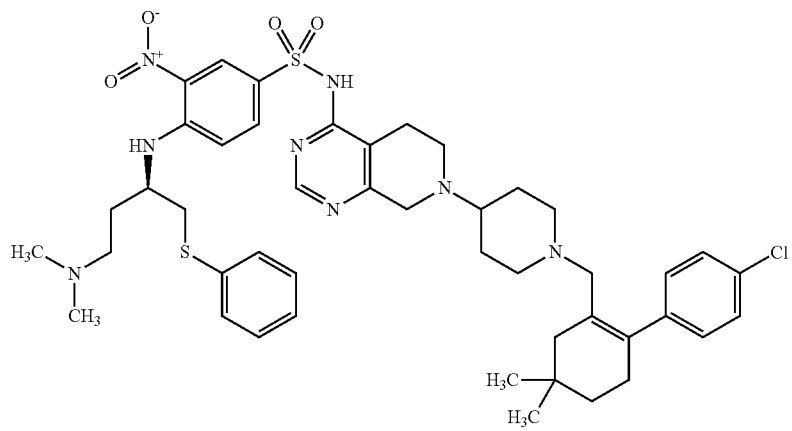 [SMILES: CN(C)CC[C@H](CSc1ccccc1)Nc1ccc(S(=O)(=O)Nc2ncnc3c2CCN(C2CCN(CC4=C(c5ccc(Cl)cc5)CCC(C)(C)C4)CC2)C3)cc1[N+](=O)[O-]]

$^1$H NMR (400 MHz, MeOD) δ (ppm): 8.55 (d, J=2.01 Hz, 1H), 8.04 (s, 1H), 7.77 (dd, J=2.29, 9.29 Hz, 1H), 7.24 (d, J=8.53 Hz, 2H), 7.12-7.16 (m, 2H), 6.96-7.00 (m, 5 H), 6.72 (d, J=9.54 Hz, 1H), 3.91-4.00 (m, 1H), 3.44 (s, 2H), 3.23-3.26 (m, 1H), 3.09 (dd, J=5.5, 14.5 Hz, 1H), 2.93-3.05 (m, 4H), 2.66-2.77 (m, 4H), 2.53-2.58 (m, 2H), 2.37-2.47 (m, 7H), 2.17-2.26 (m, 2H), 1.77-2.11 (m, 8H), 1.47-1.62 (m, 2H), 1.41 (t, J=6.27 Hz, 2H), 0.92 (s, 6H); HR-MS (m/z, MH+): 873.57.

Example 3

N-(7-((2S)-[((4'-chlorobiphenyl-2-yl)methyl)-2-methylpiperidin-4-yl)-5,6,7,8-tetrahydropyrido[3,4-d]pyrimidin-4-yl]-4-((R)-4-(dimethylamino)-1-(phenylthio)butan-2-ylamino)-3-nitrobenzenesulfonamide

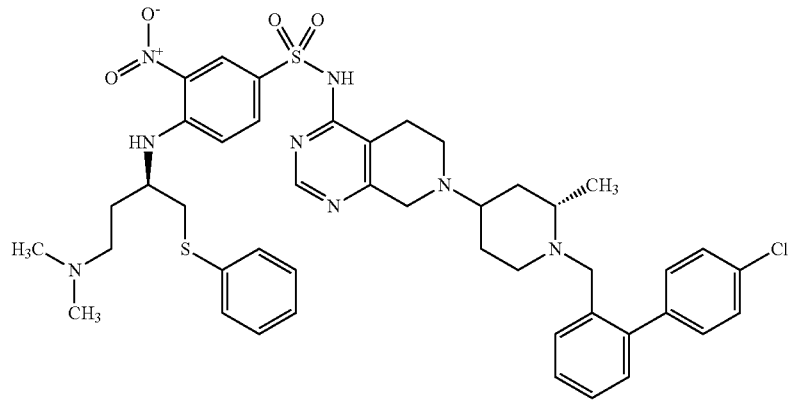 [SMILES: C[C@H]1CC(N2CCc3c(ncnc3NS(=O)(=O)c3ccc(N[C@H](CCN(C)C)CSc4ccccc4)c([N+](=O)[O-])c3)C2)CCN1Cc1ccccc1-c1ccc(Cl)cc1]

Isolated as a 2:1 mixture of diastereomers. ¹H NMR of major diastereomer (400 MHz, MeOD) δ (ppm): 8.64 (d, J=2.01 Hz, 1H), 8.12 (s, 1 H), 7.83-7.87 (m, 1H), 7.52 (d, J=7.53 Hz, 1H), 7.22-7.42 (m, 9H), 7.07-7.11 (m, 3H), 6.79 (d, J=9.03 Hz, 1H), 4.08 (d, J=13.05 Hz, 1H), 3.98-4.08 (m, 1H), 3.50 (s, 2H), 3.28 (m, 1H), 3.13-3.18 (dd, J=5.5, 16.0 Hz, 1H), 2.96 (d, J=13.05 Hz, 1H), 2.74-2.81 (m, 3H), 2.63-2.68 (m, 2H), 2.33-2.50 (m, 3 H), 2.21 (s, 6H), 2.00-2.15 (m, 2H), 1.81-1.92 (m, 2H), 1.68-1.77 (m, 2H), 1.25-1.43 (m, 2H), 1.01 (d, J=6.02 Hz, 3H); HR-MS (m/z, MH+): measured 855.51.

Example 4

N-(7-((2S)-1-((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide

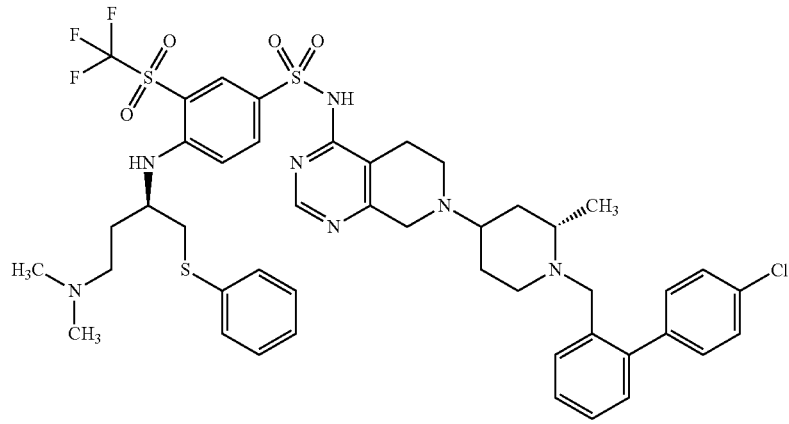 [SMILES: C[C@H]1CC(N2CCc3c(ncnc3NS(=O)(=O)c3ccc(N[C@H](CCN(C)C)CSc4ccccc4)c(S(=O)(=O)C(F)(F)F)c3)C2)CCN1Cc1ccccc1-c1ccc(Cl)cc1]

Isolated as a 2.5:1 mixture of diastereomers. $^1$H NMR of the major diastereomer (400 MHz, MeOD) δ (ppm): 8.34 (d, J=2.01 Hz, 1H), 8.11-8.25 (s, 1H), 8.0 (d, J=9.54 Hz, 1H), 7.66-7.70 (m, 1H), 7.30-7.58 (m, 9H), 7.12-7.25 (m, 3H), 6.88 (d, J=9.54 Hz, 1H), 4.60-4.79 (m, 1H), 3.90-4.12 (m, 2H), 3.58-3.70 (m, 2H), 3.42-3.57 (m, 1H), 3.04-3.27 (m, 4H), 2.68-2.99 (m, 10H), 2.44-2.64 (m, 3H), 2.01-2.32 (m, 3H), 1.55-2.00 (m, 3H), 1.38 (d, J=6.02 Hz, 3H); HR-MS (m/z, MH+): 942.57.

Example 5

(R)-4-(4-(dimethylamino)-1-(phenylthio)butan-2-ylamino)-N-(7-(1-((4'-fluorobiphenyl-2-yl)methyl)piperidin-4-yl)-5,6,7,8-tetrahydropyrido[3,4-d]pyrimidin-4-yl)-3-(trifluoromethylsulfonyl)benzenesulfonamide

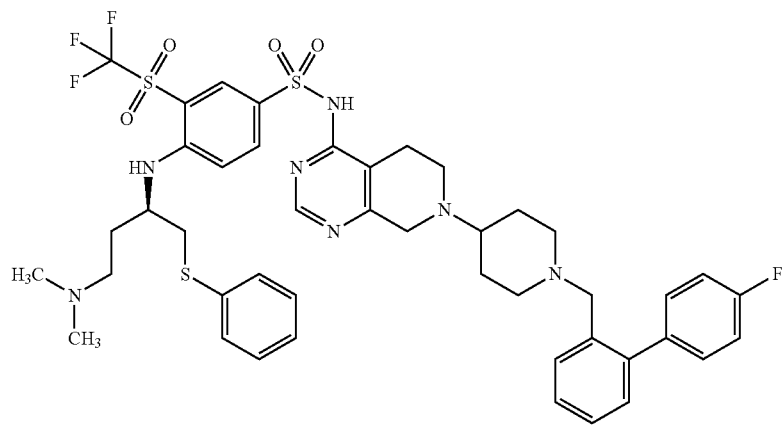 [SMILES: CN(C)CC[C@H](CSc1ccccc1)Nc1ccc(S(=O)(=O)Nc2ncnc3c2CCN(C2CCN(Cc4ccccc4-c4ccc(F)cc4)CC2)C3)cc1S(=O)(=O)C(F)(F)F]

$^1$H NMR (400 MHz, MeOD) δ ppm: 8.32 (d, J=12.05 Hz, 2H), 8.01 (d, J=8.53 Hz, 1H), 7.76 (s, 1H), 7.49-7.59 (m, 2H), 7.11-7.45 (m, 9H), 6.93 (t, J=8.03 Hz, 2H), 4.36 (s, 2H), 4.04-4.10 (m, 1H), 3.66-3.86 (m, 2H), 3.29-3.42 (m, 2H), 3.08-3.24 (m, 4H), 2.69-3.04 (m, 5H), 2.85 (s, 6H), 2.54-2.66 (m, 2H), 2.19-2.31 (m, 1H), 1.99-2.16 (m, 3H), 1.73-1.87 (m, 2H); HR-MS (m/z, MH+): 912.09.

Example 6

(R)-N-(7-(1-(((4'-bromobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

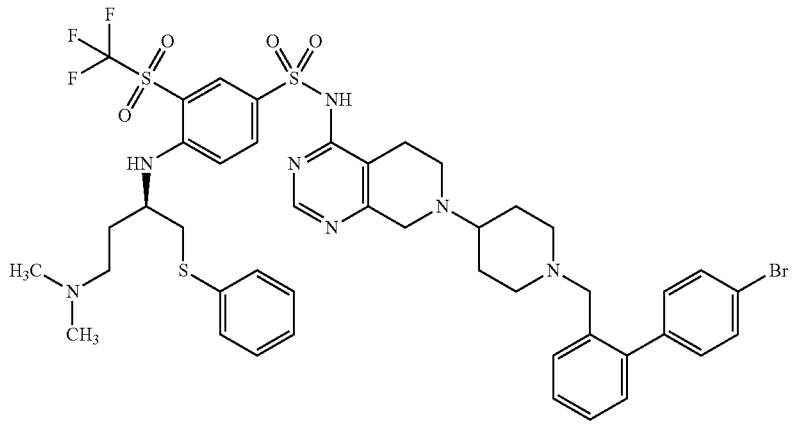 [SMILES: CN(C)CC[C@H](CSc1ccccc1)Nc1ccc(S(=O)(=O)Nc2ncnc3c2CCN(C2CCN(Cc4ccccc4-c4ccc(Br)cc4)CC2)C3)cc1S(=O)(=O)C(F)(F)F]

$^1$H NMR (600 MHz, Acetone-d6) δ ppm: 8.37 (s, 1H), 8.30 (s, 1H), 7.94-7.99 (m, 1H), 7.61 (d, J=8.31 Hz, 2H), 7.51 (d, J=7.18 Hz, 1H), 7.41-7.44 (m, 4H), 7.32-7.38 (m, 2H), 7.30 (t, J=7.55 Hz, 2H), 7.21-7.26 (m, 2H), 6.87-6.90 (m, 1H), 4.10-4.16 (m, 1H), 3.59 (s, 2H), 3.36 (s, 2H), 3.26-3.35 (m, 2H), 3.04-3.08 (m, 1H), 2.84 (d, J=11.71 Hz, 2H), 2.78 (t, J=5.67 Hz, 2H), 2.55-2.61 (m, 1H), 2.53 (t, J=5.29 Hz, 2H), 2.40-2.46 (m, 1H), 2.31-2.37 (m, 1H), 2.18-2.25 (s, 6H), 1.86-1.97 (m, 3H), 1.78 (d, J=11.33 Hz, 2H), 1.49-1.58 (m, 2H); HR-MS (m/z, MH+): 973.01.

Example 7

(R)-N-(7-(1-(2-bromobenzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

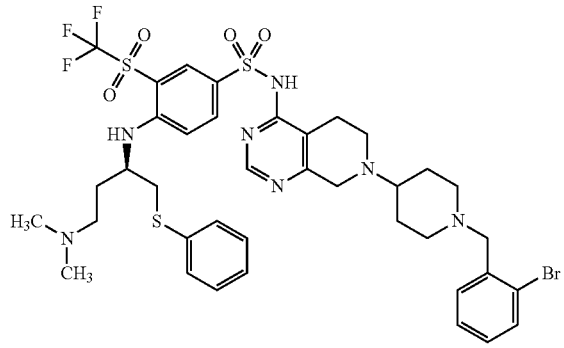 [SMILES: CN(C)CC[C@H](CSc1ccccc1)Nc1ccc(S(=O)(=O)Nc2ncnc3c2CCN(C2CCN(Cc4ccccc4Br)CC2)C3)cc1S(=O)(=O)C(F)(F)F]

$^1$H NMR (400 MHz, MeOD) MeOD) δ (ppm): 8.34 (d, J=1.51 Hz, 1H), 8.12 (s, 1H), 7.95 (dd, J=2.01, 9.03 Hz, 1H), 7.57 (d, J=7.53 Hz, 1H), 7.50 (d, J=7.53 Hz, 1H), 7.31-7.36 (m, 3H), 7.15-7.24 (m, 4H), 6.70 (d, J=9.03 Hz, 1H), 3.87-3.96 (m, 1H), 3.68 (s, 2H), 3.62 (s, 2H), 3.11-3.26 (m, 3H), 3.05 (m, 2H), 2.91 (t, J=5.77 Hz, 2H), 2.54-2.79 (m, 5H), 2.46 (s, 6H), 1.82-2.32 (m, 5H), 1.62-1.74 (m, 2H); HR-MS (m/z, MH+): 896.90.

General Reductive Amination Procedure 2

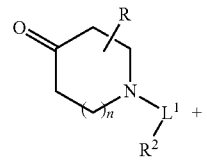

IX

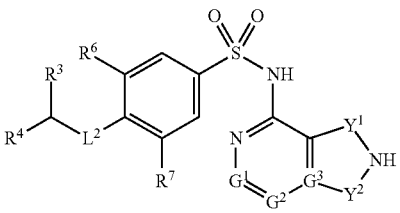

V

A solution of amine V (1 eq), ketone IX (1 eq), acetic acid (1 eq), sodium triacetoxyborohydride (1.5 eq) and molecular sieves (~400 mg/mmol V) in DCE (12.4 mL/mmol V) was stirred at 45° C. for 12 hours. The mixture was cooled to room temperature, filtered through Celite, and concentrated. The crude residue was purified by flash chromatography on silica gel (0-100% methanol in $CH_2Cl_2$).

Example 8

N-{7-[2-(4-Chloro-phenyl)-5,5-dimethyl-cyclohex-1-enylmethyl]-5,6,7,8-tetrahydro-pyrido[3,4-d]pyrimidin-4-yl}-4-((R)-3-morpholin-4-yl-1-phenylsulfanylmethyl-propylamino)-3-trifluoromethanesulfonylbenzenesulfonamide

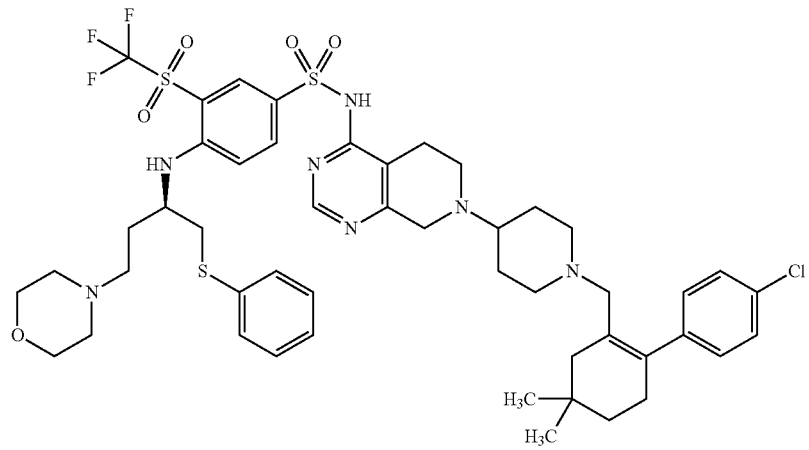 [SMILES: CC1(C)CCC(c2ccc(Cl)cc2)=C(CN2CCC(N3CCc4c(ncnc4NS(=O)(=O)c4ccc(N[C@H](CCN5CCOCC5)CSc5ccccc5)c(S(=O)(=O)C(F)(F)F)c4)C3)CC2)C1]

Following General Reductive Amination Procedure 2 above, (R)-4-(4-morpholino-1-(phenylthio)butan-2-ylamino)-N-(5,6,7,8-tetrahydropyrido[3,4-d]pyrimidin-4-yl)-3-(trifluoromethylsulfonyl)benzenesulfonamide (83 mg, 0.121 mmol) and 1-[2-(4-chloro-phenyl)-5,5-dimethyl-cyclohex-1-enylmethyl]piperidin-4-one (40 mg, 0.121 mmol), afford the title compound (11.4 mg, 9% yield).

¹H NMR (400 MHz, MeOD) δ ppm: 8.34 (bs, 1H), 8.25 (bs, 1H), 7.97 (d, J=8.4 Hz, 1H), 7.37 (m, 4H), 7.09-7.27 (m, 5H), 6.79-6.89 (d, J=8.4 Hz, 1H), 3.96-4.19 (m, 1H), 3.11-3.84 (m, 9H), 2.49-2.96 (m, 10H), 2.38 (bs, 2H), 1.62-2.22 (m, 8H), 1.55 (bs, 2H.), 1.29 (bs, 4H), 1.05 (bs, 6H), 0.9 (s, 2H)

TOF MS ES+ (M+H⁺):1002.47

HPLC retention time: 1.84 minutes (Agilent 1100 HPLC system; Inertsii ODS3 100×3 mm C18 column; flow rate of 1.0 mL/minute; gradient of 5-95% acetonitrile/water with 0.1% FA).

Examples 9-64 were prepared by reductive amination of ketones IX with amines V following General Procedure 2 above.

Example 9

(R)-N-(7-(1((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide

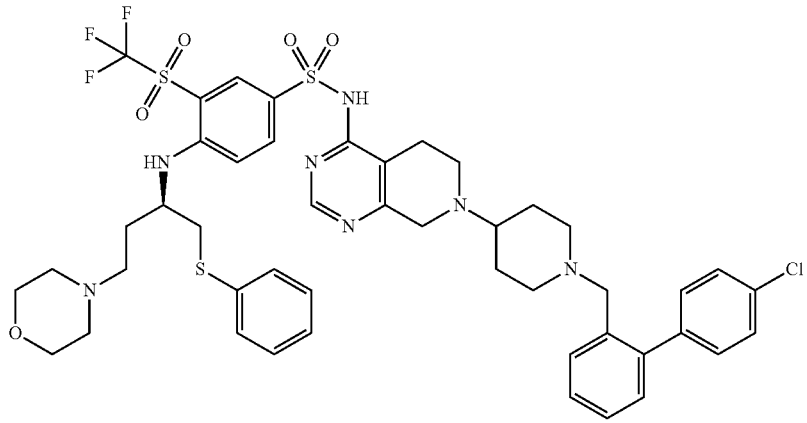 [SMILES: O=S(=O)(Nc1ncnc2c1CCN(C1CCN(Cc3ccccc3-c3ccc(Cl)cc3)CC1)C2)c1ccc(N[C@H](CCN2CCOCC2)CSc2ccccc2)c(S(=O)(=O)C(F)(F)F)c1]

¹H NMR (400 MHz, MeOD) δ ppm: 8.47 (d, J=2.1 Hz, 1H), 8.31 (s, 1 H), 7.95 (d, J=8.46 Hz, 1H), 7.10-7.50 (m, 13H), 6.90 (d, J=9.35 Hz, 1H), 4.30-4.15 (m, 1H), 3.86-3.92 (m, 2H), 3.83-3.86 (m, 2H), 3.69-3.80 (m, 4H), 3.23-3.42 (m, 2 H), 3.11-3.21 (m, 4H) 2.80-2.87 (m, 2H), 2.04-2.63 (m, 13H), 1.67-1.96 (m, 2 H); TOF MS ES+(M+H⁺): 970.29.

Example 10

(R)-N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

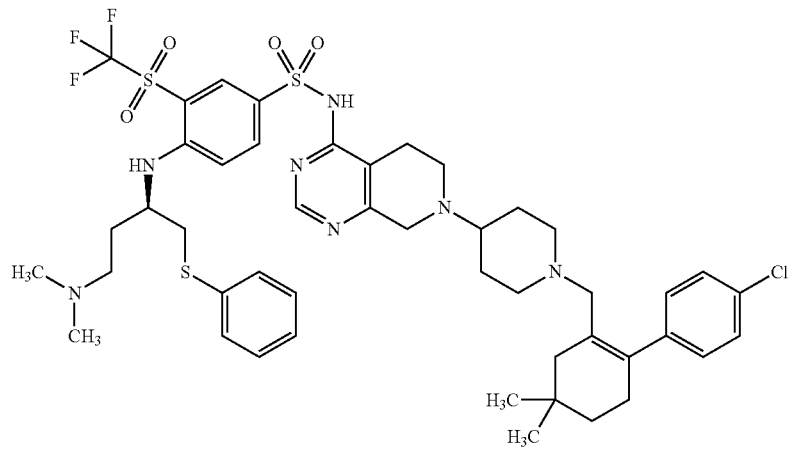 [SMILES: CN(C)CC[C@H](CSc1ccccc1)Nc1ccc(S(=O)(=O)Nc2ncnc3c2CCN(C2CCN(CC4=C(c5ccc(Cl)cc5)CCC(C)(C)C4)CC2)C3)cc1S(=O)(=O)C(F)(F)F]

$^1$H NMR (400 MHz, MeOD) δ ppm: 8.30 (d, J=2.1 Hz, 1H), 8.11 (s, 1H), 7.97 (dd, J=2.1, 8.1 Hz, 1 H), 7.39-7.30 (m, 4H), 7.25-7.13 (m, 3H), 7.09 (d, J=8.2 Hz, 2H), 6.70 (d, J=8.0 Hz, 1H), 3.87-3.98 (m, 1H), 3.54 (s, 2 H), 3.23 (dd, J=4.8, 14.2 Hz, 1H), 3.06-3.18 (m, 5H) 2.78-2.88 (m, 2H), 2.50-2.75 (m, 5H) 2.45 (s, 6H), 2.26-2.37 (m, 2H), 2.05-2.24 (m, 3H), 2.01 (bs, 2H), 1.82-1.98 (m, 3H), 1.59-1.75 (m, 2H), 1.50 (t, J=7.6 Hz, 2H), 1.02 (s, 6H); TOF MS ES+(M+H$^+$): 960.34.

Example 11

(R)-N-(7-(1((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

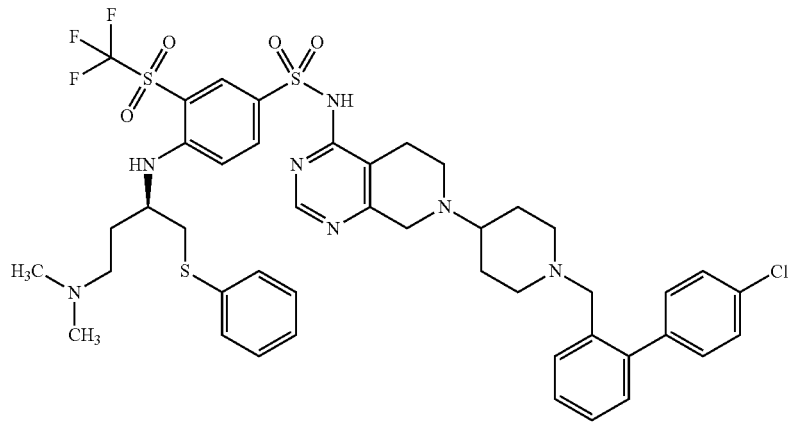 [SMILES: CN(C)CC[C@H](CSc1ccccc1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

¹H NMR (400 MHz, MeOD) δ ppm: 8.31 (d, J=2.05 Hz, 1H), 8.10 (s, 1H), 7.90-7.95 (m, 1H), 7.10-7.52 (m, 13H), 6.65 (d, f=8.2 Hz, 1H), 3.81-3.96 (m, 1H), 3.52 (s, 2H), 3.40 (s, 2H), 3.20 (dd, J=5.1, 16.0 Hz, 1H), 3.11 (dd, J=5.1, 16.0 Hz, 1H), 2.75-2.89 (m, 4H), 2.68-2.79 (m, 2H), 2.26-2.45 (m, 3H), 2.19 (s, 6H,), 1.96-2.08 (m, 1H), 1.79-1.88 (m, 4H), 1.68-1.79 (m, 1H), 1.44-1.59 (m, 2H); TOF MS ES+ (M+H⁺): 928.28.

Example 12

(R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3,5-difluorobenzenesulfonamide

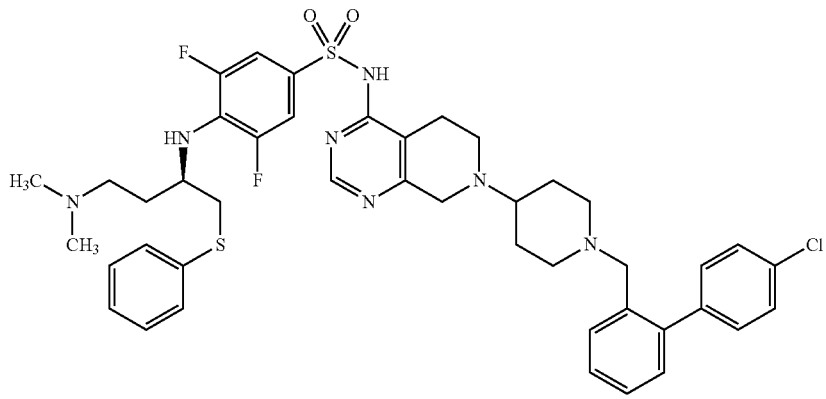 [SMILES: CN(C)CC[C@H](CSc1ccccc1)Nc1c(F)cc(S(=O)(=O)Nc2ncnc3c2CCN(C2CCN(Cc4ccccc4-c4ccc(Cl)cc4)CC2)C3)cc1F]

¹H NMR (400 MHz, chloroform-d) δ ppm 1.38-1.55 (m, 2 H) 1.62-2.00 (m, 7 H) 2.20 (s, 6 H) 2.25-2.56 (m, 5 H) 2.67 (t, J=5.56 Hz, 2 H) 2.77 (d, J=11.12 Hz, 2 H) 2.98 (dd, J=13.39, 7.33 Hz, 1 H) 3.13 (dd, J=13.14, 4.55 Hz, 1 H) 3.26 (s, 2 H) 3.46-3.61 (m, 2 H) 4.01 (br. s., 1 H) 5.47 (br. s., 1 H) 7.01-7.50 (m, 15 H) 8.05 (s, 1 H) TOF MS ES+ (M+H⁺): 832.31 Retention time=3.09 minutes.

Example 13

N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide

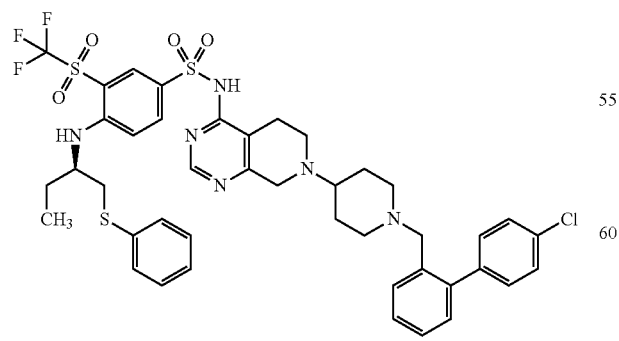

TOF MS ES+ (M+H⁺): 885.24; Retention time=4.86 minutes.

Example 14

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide

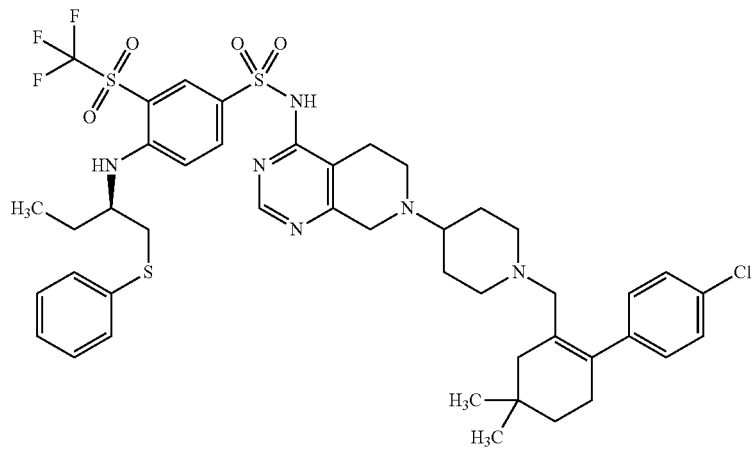 [SMILES: CC[C@H](CSc1ccccc1)Nc1ccc(S(=O)(=O)Nc2ncnc3c2CCN(C2CCN(CC4=C(c5ccc(Cl)cc5)CCC(C)(C)C4)CC2)C3)cc1S(=O)(=O)C(F)(F)F]

TOF MS ES+ (M+H$^+$): 917.29; Retention time=5.19 minutes

Example 15

N-(4-(N-(7-(1-(14'-chloro-4-fluorobiphenyl-2-yl)methyl)piperidin-4-yl)-5,6,7,8-tetrahydropyrido[3,4-d]pyrimidin-4-yl)sulfamoyl)-2-(trifluoromethylsulfonyl)phenyl)-N-(2-(phenylthio)ethyl)acetamide

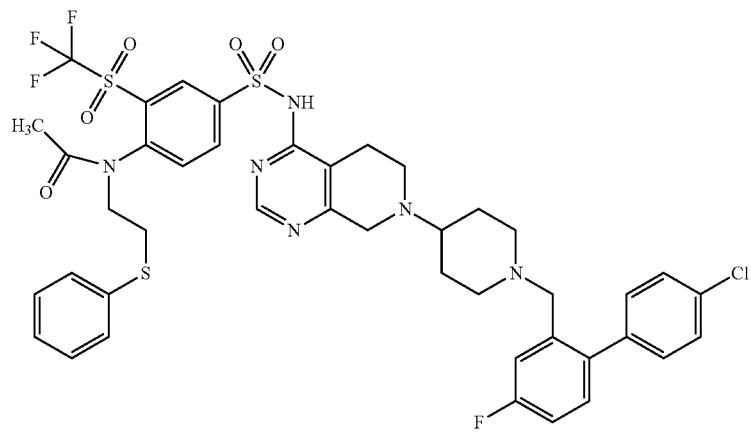 [SMILES: CC(=O)N(CCSc1ccccc1)c1ccc(S(=O)(=O)Nc2ncnc3c2CCN(C2CCN(Cc4cc(F)ccc4-c4ccc(Cl)cc4)CC2)C3)cc1S(=O)(=O)C(F)(F)F]

TOF MS ES+ (M+H$^+$): 917.20; HPLC Retention time=4.55 minutes.

Example 16

(R)-N-(7-(1-((2-(4-chlorophenol)-4,4-dimethylcyclohex-1-enyl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide

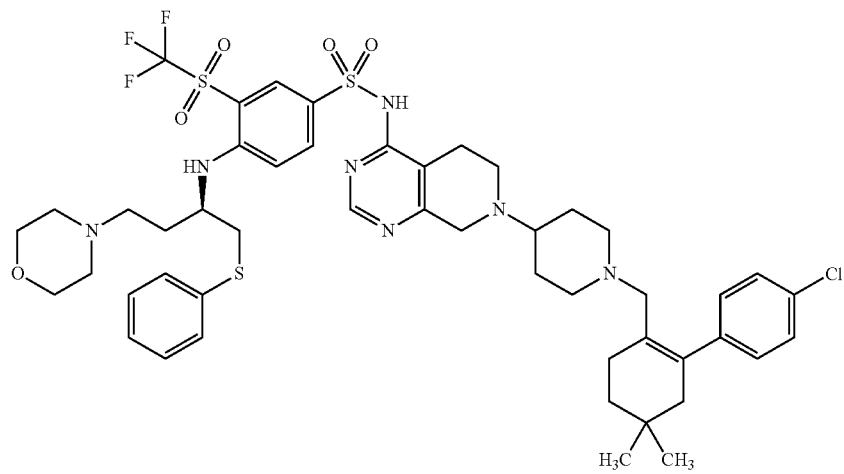 [SMILES: CC1(C)CCC(CN2CCC(N3CCc4c(ncnc4NS(=O)(=O)c4ccc(N[C@H](CCN5CCOCC5)CSc5ccccc5)c(S(=O)(=O)C(F)(F)F)c4)C3)CC2)=C(c2ccc(Cl)cc2)C1]

TOF MS ES+ (M+H$^+$): 1002.35; HPLC Retention time=3.75 minutes.

Example 17

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

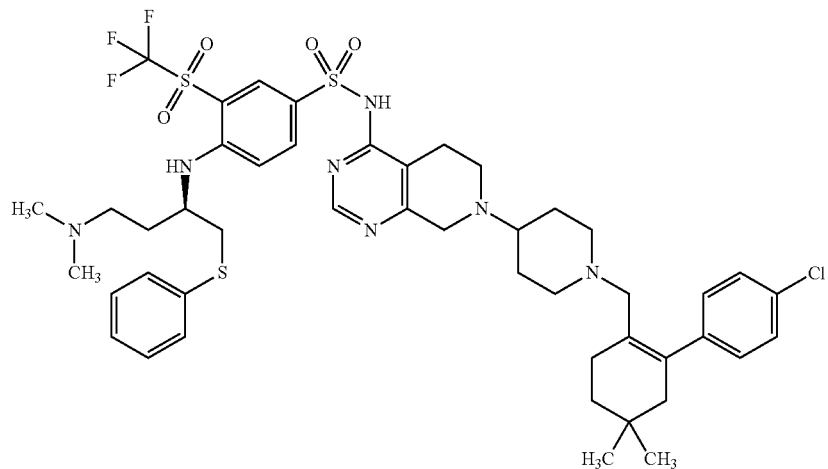 [SMILES: CN(C)CC[C@H](CSc1ccccc1)Nc1ccc(S(=O)(=O)Nc2ncnc3c2CCN(C2CCN(CC4=C(c5ccc(Cl)cc5)CC(C)(C)CC4)CC2)C3)cc1S(=O)(=O)C(F)(F)F]

TOF MS ES+ (M+H$^+$): 960.35; HPLC retention time=3.68 minutes.

Example 18

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-O-4-(1-(phenylthio)pentan-2-ylamino)-3-(trifluoromethylsulfonyl)benzenesulfonamide

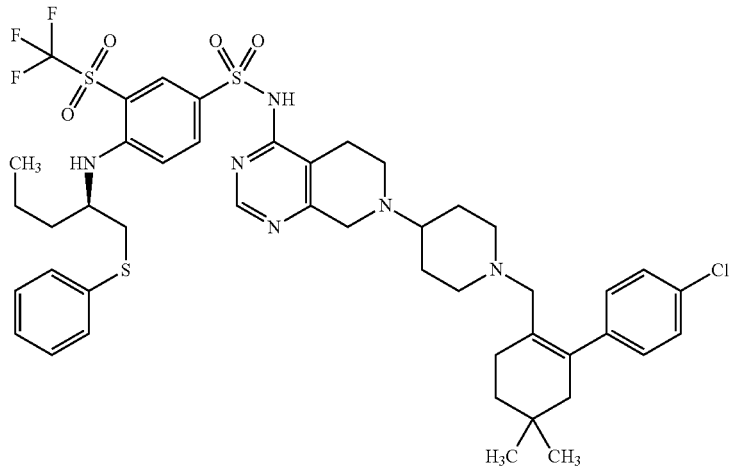 [SMILES: CCC[C@H](CSc1ccccc1)Nc1ccc(S(=O)(=O)Nc2ncnc3c2CCN(C2CCN(CC4=C(c5ccc(Cl)cc5)CC(C)(C)CC4)CC2)C3)cc1S(=O)(=O)C(F)(F)F]

TOF MS ES+ (M+H$^+$): 931.31; HPLC Retention time=5.33 minutes.

Example 19

(R)-N-(7-(1-((4'-chloro-5-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

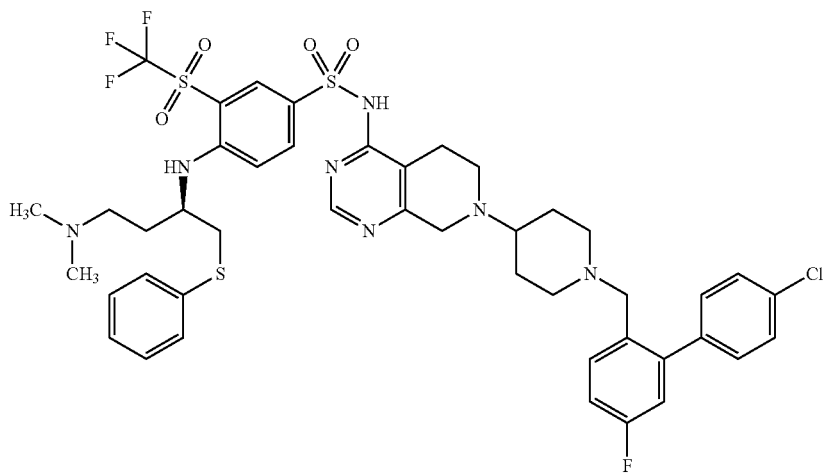 [SMILES: CN(C)CC[C@H](CSc1ccccc1)Nc1ccc(S(=O)(=O)Nc2ncnc3c2CCN(C2CCN(Cc4ccc(F)cc4-c4ccc(Cl)cc4)CC2)C3)cc1S(=O)(=O)C(F)(F)F]

TOF MS ES+ (M+H$^+$): 946.27; HPLC Retention time=3.56 minutes.

Example 20

(R)-N-(7-(1-((4'-chloro-4-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonAbenzenesulfonamide

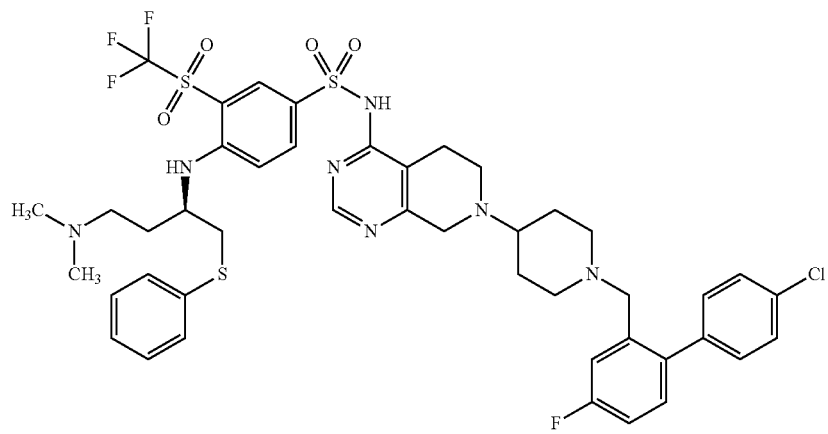 [SMILES: CN(C)CC[C@H](CSc1ccccc1)Nc1ccc(S(=O)(=O)Nc2ncnc3c2CCN(C2CCN(Cc4cc(F)ccc4-c4ccc(Cl)cc4)CC2)C3)cc1S(=O)(=O)C(F)(F)F]

TOF MS ES+ (M+H$^+$): 946.26; HPLC Retention time=3.46 minutes.

Example 21

(R)-N—-(7-(1-((4'-chloro-3-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

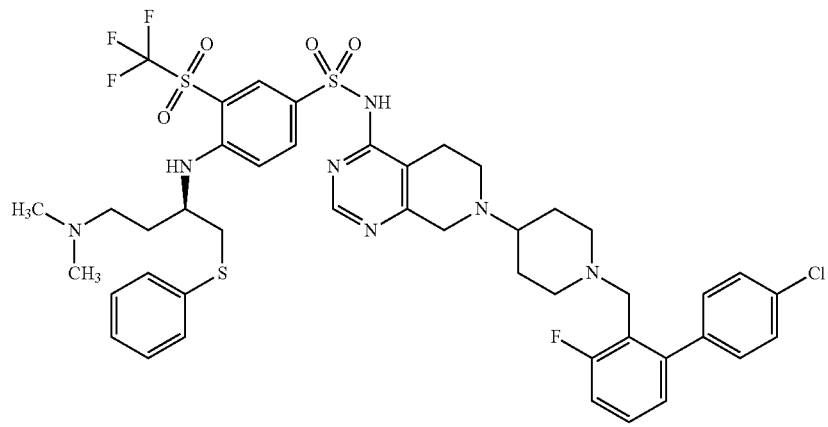 [SMILES: CN(C)CC[C@H](CSc1ccccc1)Nc1ccc(S(=O)(=O)Nc2ncnc3c2CCN(C2CCN(Cc4c(F)cccc4-c4ccc(Cl)cc4)CC2)C3)cc1S(=O)(=O)C(F)(F)F]

TOF MS ES+ (M+H$^+$): 946.26; HPLC Retention time=3.37 minutes.

Example 22

(R)-3-(4-(N-(7-(1-((4'-chlorobiphenyl-2-yl)methyl)piperidin-4-yl)-5,6,7,8-tetrahydropyrido[3,4-d]pyrimidin-4-yl)sulfamoyl)-2-nitrophenylamino)-N,N-dimethyl-4-(phenylthio)butanamide

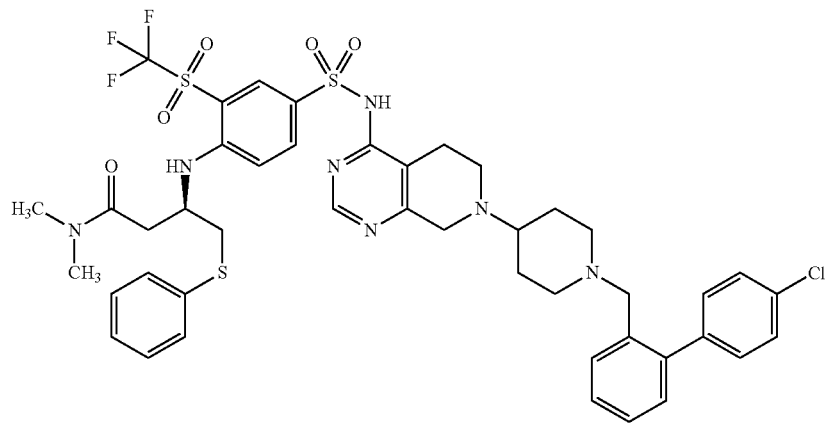 [SMILES: CN(C)C(=O)C[C@H](CSc1ccccc1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 855.29; HPLC Retention time=4.03 minutes.

Example 23

N-{7-[1-(4'-Chloro-biphenyl-2-ylmethyl)-piperidin-4-yl]-5,6,7,8-tetrahydro-pyrido[3,4-d]pyrimidin-4-yl}-4[(R)-3-(4-ethyl-piperazin-1-yl)-1-phenylsulfanylmethyl-propylamino]-3-trifluoromethanesulfonyl-benzenesulfonamide

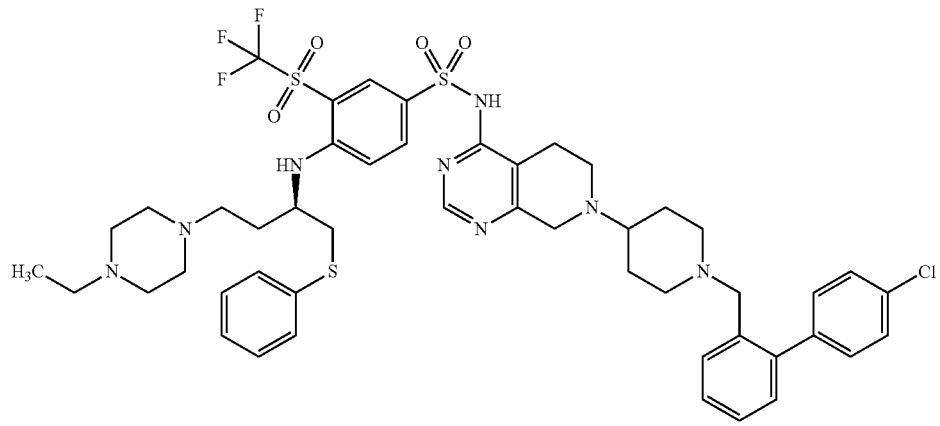 [SMILES: CCN1CCN(CC[C@H](CSc2ccccc2)Nc2ccc(S(=O)(=O)Nc3ncnc4c3CCN(C3CCN(Cc5ccccc5-c5ccc(Cl)cc5)CC3)C4)cc2S(=O)(=O)C(F)(F)F)CC1]

TOF MS ES+ (M+H$^+$): 997.33; HPLC Retention time=3.46 minutes.

Example 24

N-(7-(1-(1-(4'-chlorobiphenyl-2-yl)ethyl)piperidin-4-yl)-5,6,7,8-tetrahydropyrido[3,4-c]pyrimidin-4-yl)-4-((R)-4-morpholino-1-(phenylthio)butan-2-ylamino)-3-(trifluoromethylsulfonyl)benzenesulfonamide

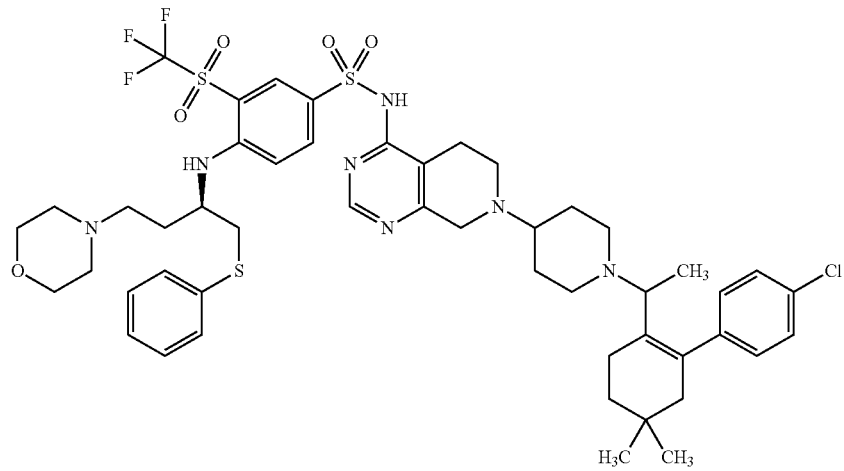 [SMILES: CC(C1=C(c2ccc(Cl)cc2)CC(C)(C)CC1)N1CCC(N2CCc3c(ncnc3NS(=O)(=O)c3ccc(N[C@H](CCN4CCOCC4)CSc4ccccc4)c(S(=O)(=O)C(F)(F)F)c3)C2)CC1]

TOF MS ES+ (M+H$^+$): 1016.36; HPLC retention time=3.69 minutes.

Example 25

4-((R)-1-Benzyloxymethyl-3-dimethylamino-propylamino)-N-{7-[1-(4'-chloro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide

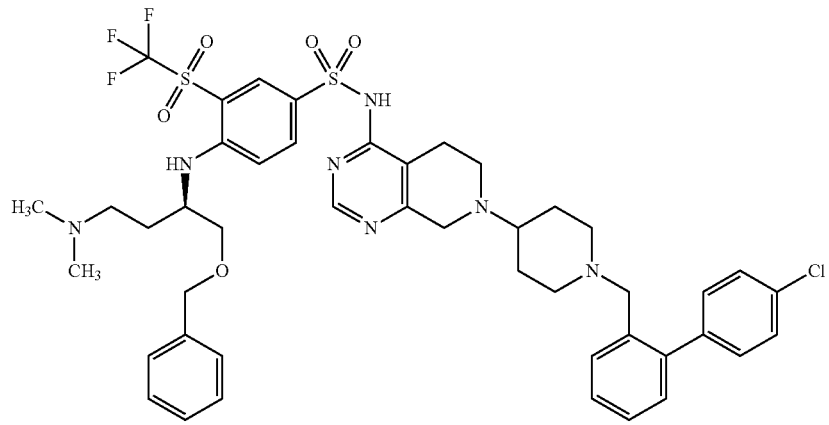 [SMILES: CN(C)CC[C@H](COCc1ccccc1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 926.31; HPLC Retention time=3.42 minutes.

Example 26

N-{7-[1-(4'-Chloro-biphenyl-2-ylmethyl)-piperidin-4-yl]-5,6,7,8-tetrahydro-pyrido[3,4-c]pyrimidin-4-yl}-4-[(R)-1-(3-chloro-phenylsulfanylmethyl)-3-dimethylamino-propylamino]-3-trifluoromethanesulfonyl-benzenesulfonamide

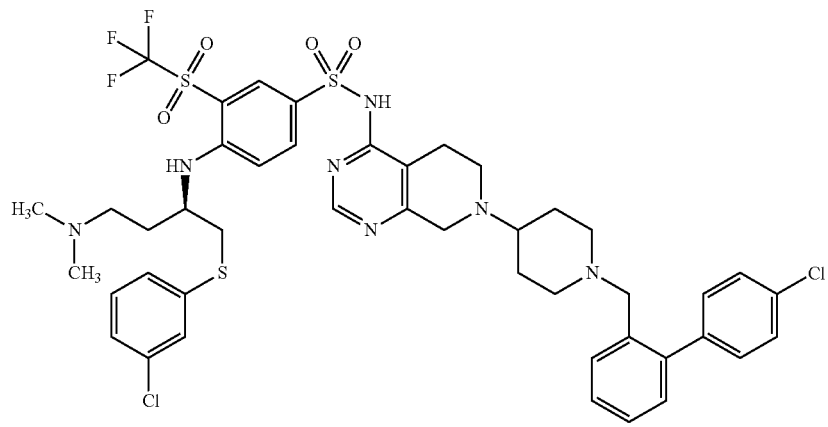 [SMILES: CN(C)CC[C@H](CSc1cccc(Cl)c1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H⁺): 962.24; HPLC Retention time=3.47 minutes.

Example 27

N-(7-(1-((2-(4-chlorophenyl)-4,4-dimethylcyclohex-1-enyl)methyl)-2-methylpiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide

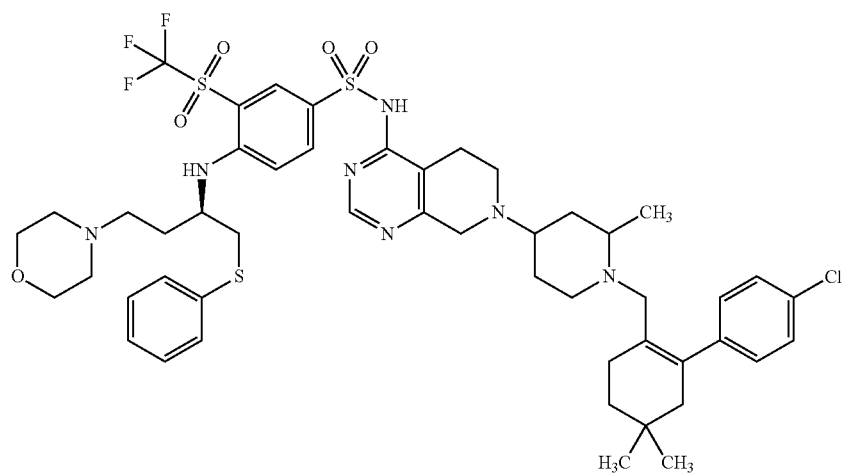 [SMILES: CC1CC(N2CCc3c(ncnc3NS(=O)(=O)c3ccc(N[C@H](CCN4CCOCC4)CSc4ccccc4)c(S(=O)(=O)C(F)(F)F)c3)C2)CCN1CC1=C(c2ccc(Cl)cc2)CC(C)(C)CC1]

TOF MS ES+ (M+H⁺): 1016.36; HPLC Retention time=3.76 minutes.

Example 28

(R)-N-(7-(1((2-(4-chlorophenyl)-4,4-dimethylcyclo-hex-1-enyl)methyl)piperidin-4-yl)-5,6,7,8-tetrahy-dropyrido[3,4-d]pyrimidin-4-yl)-4-(1-(2-chlorophe-nylthio)-4-(dimethylamino)butan-2-ylamino)-3-(trifluoromethylsulfonyl)benzenesulfonamide

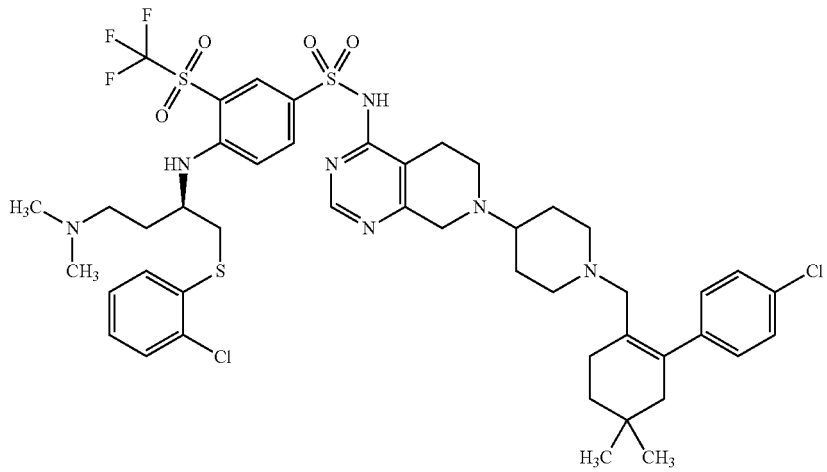 [SMILES: CN(C)CC[C@H](CSc1ccccc1Cl)Nc1ccc(S(=O)(=O)Nc2ncnc3c2CCN(C2CCN(CC4=C(c5ccc(Cl)cc5)CC(C)(C)CC4)CC2)C3)cc1S(=O)(=O)C(F)(F)F]

$^1$H NMR (400 MHz, MeOD) δ ppm 1.00 (s, 6 H) 1.44-1.58 (m, 2 H) 1.58-1.75 (m, 2 H) 1.82-1.98 (m, 3 H) 2.01-2.20 (m, 5 H) 2.26 (br. s., 2 H) 2.43 (s, 6 H) 2.52 (t, J=11.12 Hz, 1 H) 2.57-2.74 (m, 4 H) 2.74-2.86 (m, 2 H) 3.02-3.25 (m, 5 H) 3.25-3.37 (m, 1 H) 3.54 (s, 2 H) 3.99 (dd, J=8.34, 4.80 Hz, 1 H) 6.78 (d, J=9.60 Hz, 1 H) 7.06 (d, J=8.59 Hz, 2 H) 7.09-7.18 (m, 2 H) 7.27-7.37 (m, 3 H) 7.37-7.49 (m, 1 H) 7.99 (dd, J=9.09, 2.02 Hz, 1 H) 8.13 (s, 1 H) 8.36 (d, J=2.02 Hz, 1 H) TOF MS ES+ (M+H$^+$): 994.29; HPLC Retention time=3.69 minutes.

Example 29

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-1-(2-chlorophenylthio)-4-(dimethylamino)butan-2-ylamino)-3-(trifluoromethylsulfonyl)benzenesulfonamide

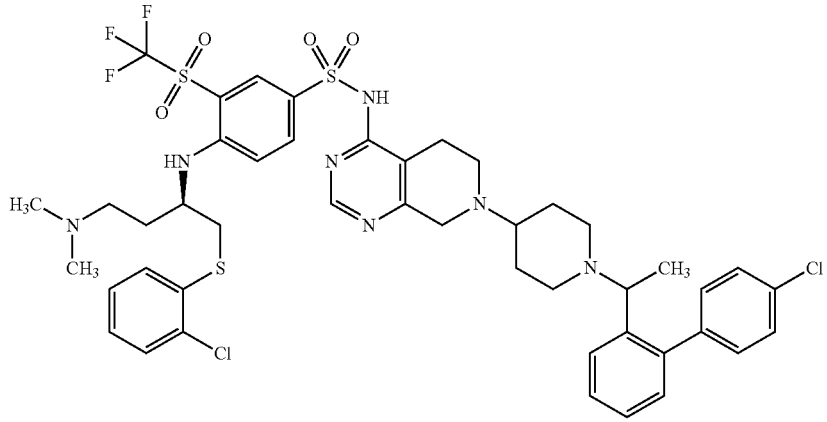 [SMILES: CC(c1ccccc1-c1ccc(Cl)cc1)N1CCC(N2CCc3c(ncnc3NS(=O)(=O)c3ccc(N[C@H](CCN(C)C)CSc4ccccc4Cl)c(S(=O)(=O)C(F)(F)F)c3)C2)CC1]

$^1$H NMR (400 MHz, MeOD) δ ppm 1.44 (d, J=6.57 Hz, 3 H) 1.47-1.57 (m, 1 H) 1.57-1.71 (m, 1 H) 1.77-2.21 (m, 6 H) 2.42-2.56 (m, 7 H) 2.58-2.86 (m, 6 H) 2.90 (d, J=10.11 Hz, 1 H) 3.13-3.27 (m, 2 H) 3.27-3.37 (m, 1 H) 3.56 (s, 2 H) 3.73 (q, J=6.57 Hz, 1 H) 3.94-4.06 (m, 1 H) 6.78 (d, J=9.60 Hz, 1 H) 7.07-7.17 (m, 2 H) 7.17-7.38 (m, 5 H) 7.38-7.50 (m, 4 H) 7.63 (d, J=6.57 Hz, 1 H) 7.99 (dd, J=9.09, 2.53 Hz, 1 H) 8.12 (s, 1 H) 8.36 (d, J=2.53 Hz, 1 H) TOF MS ES+ (M+H$^+$): 976.25; HPLC retention time=3.49 minutes.

Example 30

(R)-N-(7(1-((4'-chlorobiphenyl-2-yl)methyl)piperidin-4-yl)-5,6,7,8-tetrahydropyrido[3,4-d]pyrimidin-4-yl)-4-(l-(phenylthio)-4-(piperidin-1-yl)butan-2-ylamino)-3-(trifluoromethylsulfonyl)benzenesulfonamide

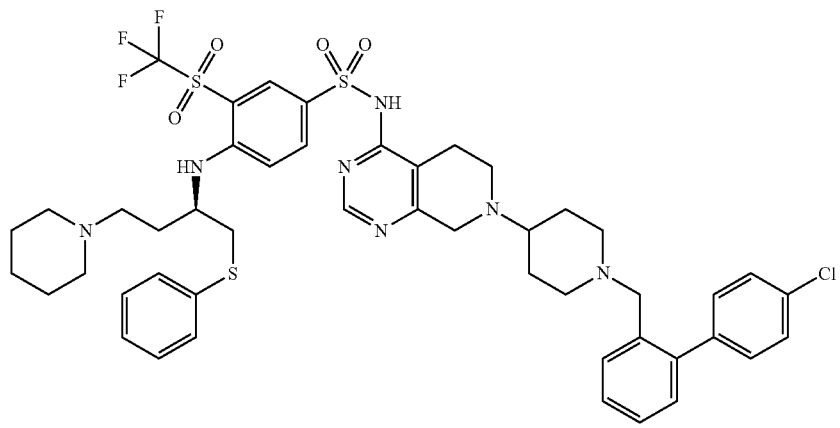 [SMILES: O=S(=O)(Nc1ncnc2c1CCN(C1CCN(Cc3ccccc3-c3ccc(Cl)cc3)CC1)C2)c1ccc(N[C@H](CCN2CCCCC2)CSc2ccccc2)c(S(=O)(=O)C(F)(F)F)c1]

TOF MS ES+ (M+H$^+$): 968.31; HPLC Retention time=3.48 minutes.

Example 31

N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide

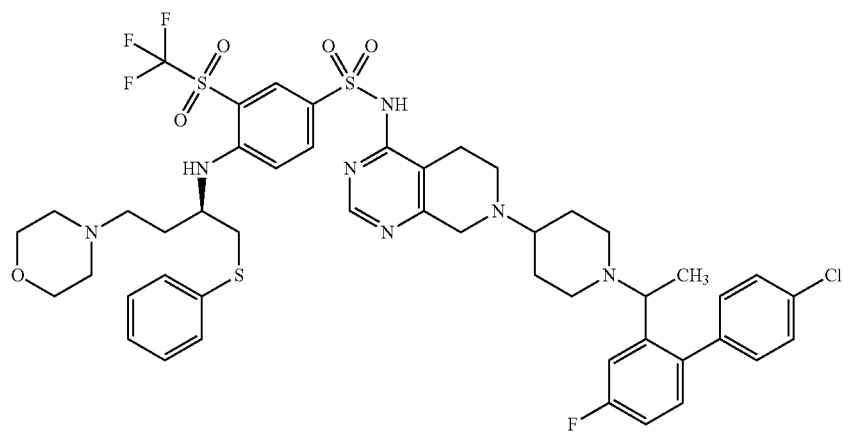 [SMILES: CC(c1cc(F)ccc1-c1ccc(Cl)cc1)N1CCC(N2CCc3c(ncnc3NS(=O)(=O)c3ccc(N[C@H](CCN4CCOCC4)CSc4ccccc4)c(S(=O)(=O)C(F)(F)F)c3)C2)CC1]

TOF MS ES+ (M+H$^+$): 1002.29; HPLC Retention time=4.26 minutes.

Example 32

(R)-N-(7-(1-((2-(4-chlorophenyl)-4,4-dimethylcyclohex-1-enyl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide

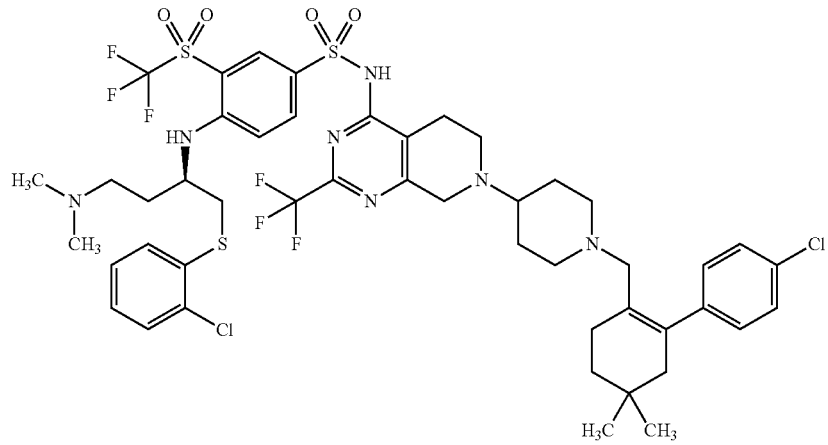 [SMILES: CN(C)CC[C@H](CSc1ccccc1Cl)Nc1ccc(S(=O)(=O)Nc2nc(C(F)(F)F)nc3c2CCN(C2CCN(CC4=C(c5ccc(Cl)cc5)CC(C)(C)CC4)CC2)C3)cc1S(=O)(=O)C(F)(F)F]

TOF MS ES+ (M+H$^+$): 1062.28; HPLC Retention time=4.09 minutes.

Example 33

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide

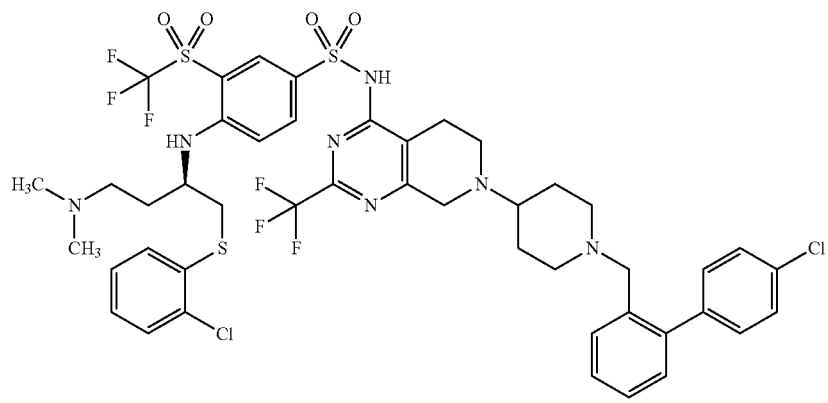 [SMILES: CN(C)CC[C@H](CSc1ccccc1Cl)Nc1ccc(S(=O)(=O)Nc2nc(C(F)(F)F)nc3c2CCN(C2CCN(Cc4ccccc4-c4ccc(Cl)cc4)CC2)C3)cc1S(=O)(=O)C(F)(F)F]

TOF MS ES+ (M+H$^+$): 1030.22; HPLC Retention time=3.83 minutes.

Example 34

N-(7-(1-(1-(4'-chlorobiphenyl-2-yl)ethyl)piperidin-4-yl)-2-(trifluoromethyl)-5,6,7,8-tetrahydropyrido[3,4-d]pyrimidin-4-yl)-4-((R)-1-(2-chlorophenylthio)-4-(dimethylamino) butan-2-ylamino)-3-(trifluoromethylsulfonyl)benzenesulfonamide

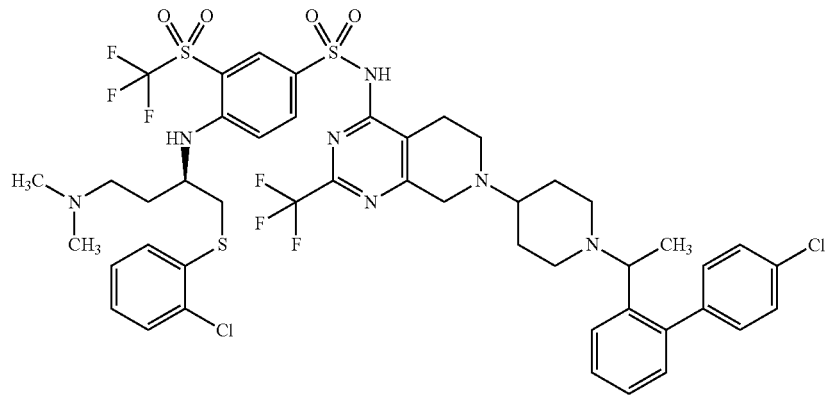 [SMILES: CC(c1ccccc1-c1ccc(Cl)cc1)N1CCC(N2CCc3c(nc(C(F)(F)F)nc3NS(=O)(=O)c3ccc(N[C@H](CCN(C)C)CSc4ccccc4Cl)c(S(=O)(=O)C(F)(F)F)c3)C2)CC1]

TOF MS ES+ (M+H$^+$): 1044.24; HPLC Retention time=4.58 minutes.

Example 35

N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-(4-methylpiperazin-1-yl)-1-(phenylthio)butan-2-ylamino)-3-(trifluoromethylsulfonyl)benzenesulfonamide

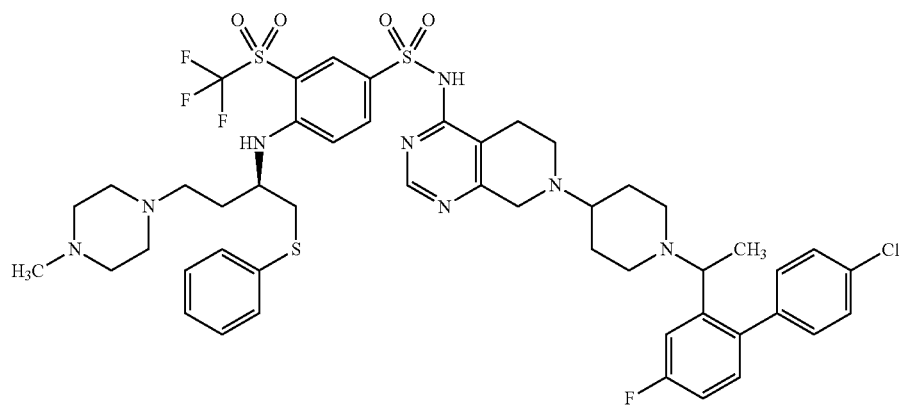 [SMILES: CC(c1cc(F)ccc1-c1ccc(Cl)cc1)N1CCC(N2CCc3c(ncnc3NS(=O)(=O)c3ccc(N[C@H](CCN4CCN(C)CC4)CSc4ccccc4)c(S(=O)(=O)C(F)(F)F)c3)C2)CC1]

TOF MS ES+ (M+H$^+$): 1033.32; HPLC Retention time=4.15 minutes.

Example 36

(R)-N-(7-(1-((4'-chloro-4-methoxybiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

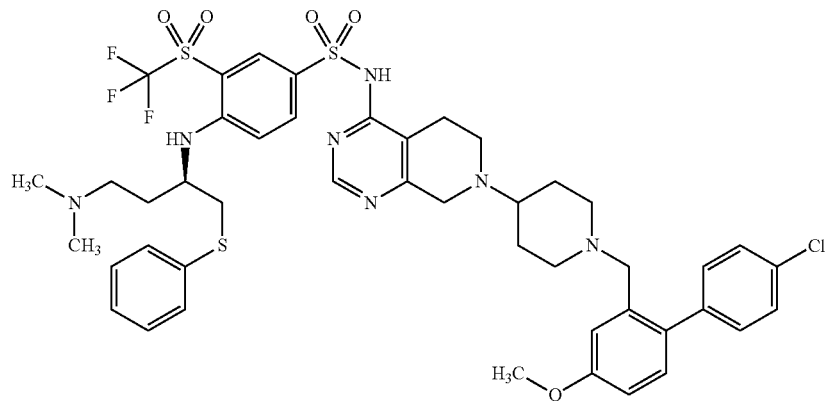 [SMILES: COc1ccc(-c2ccc(Cl)cc2)c(CN2CCC(N3CCc4c(ncnc4NS(=O)(=O)c4ccc(N[C@H](CCN(C)C)CSc5ccccc5)c(S(=O)(=O)C(F)(F)F)c4)C3)CC2)c1]

TOF MS ES+ (M+H$^+$): 958.28; HPLC Retention time=3.57 minutes.

Example 37

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(4-fluoro-phenylsulfanylmethyl)-propylamino]-3-trifluoromethanesulfonyl-benzenesulfonamide

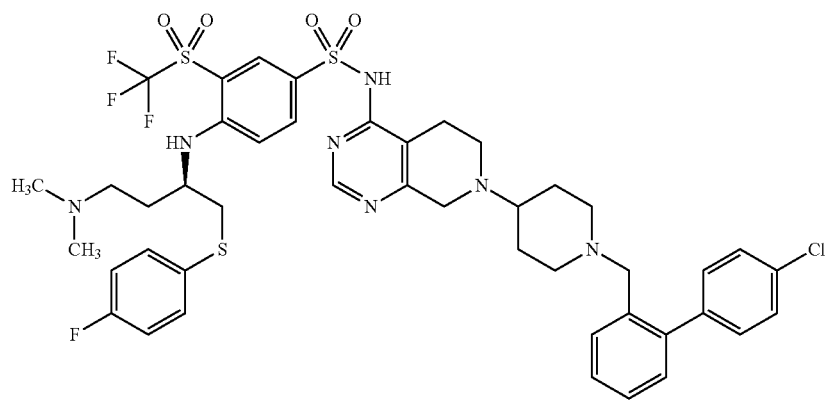 [SMILES: CN(C)CC[C@H](CSc1ccc(F)cc1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 946.26; HPLC 3.39 Retention time=minutes.

Example 38

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2,6-dichlorophenylthio)-4-(dimethylamino)butan-2-ylamino)-3-(trifluoromethylsulfonyl)benzenesulfonamide

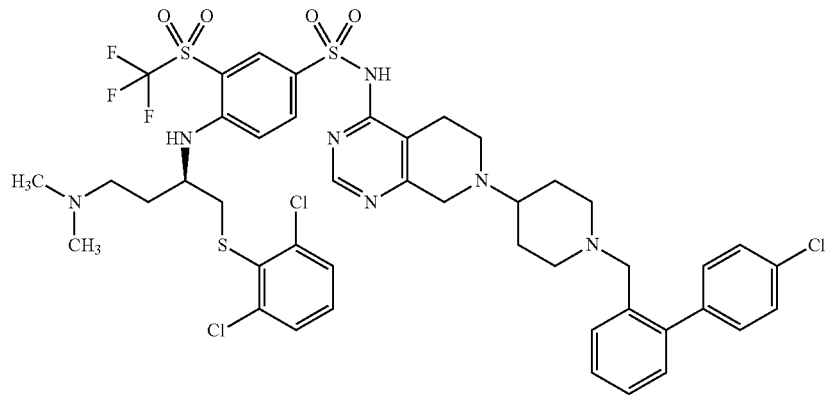 [SMILES: CN(C)CC[C@H](CSc1c(Cl)cccc1Cl)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

$^1$H NMR (400 MHz, MeOD) δ ppm 1.49-1.65 (m, 2 H) 1.82-2.00 (m, 3 H) 2.05 (t, J=11.12 Hz, 2 H) 2.11-2.25 (m, 1 H) 2.46-2.60 (m, 7 H) 2.66 (t, J=4.80 Hz, 2 H) 2.68-2.84 (m, 2 H) 2.84-2.98 (m, 4 H) 3.09-3.20 (m, 1 H) 3.20-3.29 (m, 1 H) 3.57 (s, 2 H) 161 (s, 2 H) 3.81 (dd, J=8.08, 5.05 Hz, 1 H) 6.59 (d, J=9.60 Hz, 1 H) 7.20-7.29 (m, 2 H) 7.31-7.46 (m, 8 H) 7.49-7.56 (m, 1 H) 7.95 (dd, J=9.09, 2.02 Hz, 1 H) 8.13 (s, 1 H) 8.34 (d, J=2.02 Hz, 1 H) TOF MS ES+ (M+H$^+$): 996.20; HPLC Retention time=3.55 minutes.

Example 39

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3,4-dichloro-phenylsulfanylmethyl)-3-dimethylamino-propylamino]-3-trifluoromethanesulfonyl-benzenesulfonamide

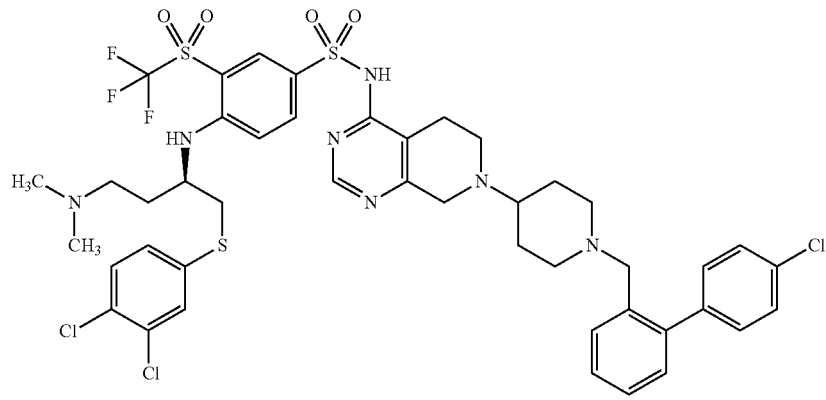 [SMILES: CN(C)CC[C@H](CSc1ccc(Cl)c(Cl)c1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 996.19; HPLC Retention time=3.55 minutes.

Example 40

(R)-N—O-(1-((4'-chlorobiphenyl-2-yl)methyl)piperidin-4-yl)-5,6,7,8-tetrahydropyrido[3,4-d]pyrimidin-4-yl)-4-(1-(2-chlorophenylthio)-4-(dimethylamino) butan-2-ylamino)-3-(trifluoromethylsulfonyl)benzenesulfonamide

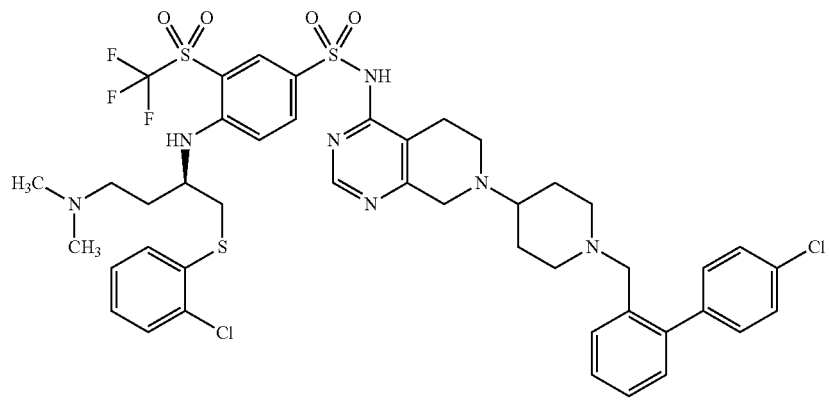

$^1$H NMR (400 MHz, CHLOROFORM-d) δ ppm 1.46 (t, J=10.36 Hz, 2 H) 1.58-1.88 (m, 4 H) 1.89-2.01 (m, 1 H) 2.11 (s, 6 H) 2.15-2.44 (m, 4 H) 2.49 (br. s., 2 H) 2.67 (br. s., 2 H) 2.71-2.84 (m, 2 H) 2.89-3.11 (m, 2 H) 125 (s, 2 H) 3.45-3.57 (m, 2 H) 3.57-3.66 (m, 1 H) 3.75-3.92 (m, 1 H) 6.53 (d, J=9.60 Hz, 1 H) 7.04-7.44 (m, 12 H) 7.62 (d, J=8.08 Hz, 1 H) 7.81 (d, J=9.09 Hz, 1 H) 8.08 (br. s., 1 H) 8.22 (s, 1 H) TOF MS ES+ (M+H$^+$): 962.24; HPLC retention time=3.45 minutes.

Example 41

(R)-N-(7-(1-((4'-chlorobiphenyl-2-yl)-methyl)piperidin-4-yl)-5,6,7,8-tetrahydropyrido[3,4-c]pyrimidin-4-yl)-4-(1-(3,5-dichlorophenylthio)-4-(dimethylamino) butan-2-ylamino)-3-(trifluoromethylsulfonyl)benzenesulfonamide

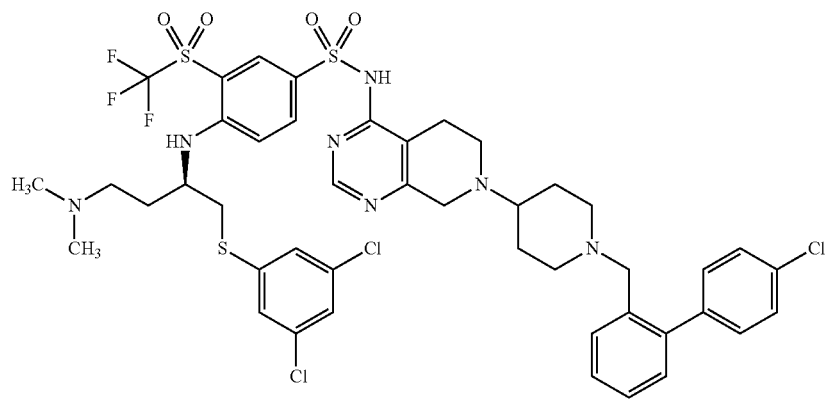 [SMILES: CN(C)CC[C@H](CSc1cc(Cl)cc(Cl)c1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

$^1$H NMR (400 MHz, MeOD) δ ppm 1.47-1.65 (m, 2 H) 1.82-1.96 (m, 3 H) 1.96-2.14 (m, 3 H) 2.40-2.57 (m, 7 H) 2.57-2.77 (m, 4 H) 2.81-2.96 (m, 4 H) 3.19-3.29 (m, 1 H) 3.35-3.44 (m, 1 H) 3.54 (s, 2 H) 3.59 (s, 2 H) 4.04 (dd, J=8.34, 4.80 Hz, 1 H) 6.92 (d, J=9.60 Hz, 1 H) 7.13 (s, 1 H) 7.19-7.28 (m, 3 H) 7.30-7.46 (m, 6 H) 7.52 (d, J=6.57 Hz, 1 H) 8.08 (dd, J=9.09, 2.53 Hz, 1 H) 8.14 (s, 1 H) 8.41 (d, J=2.02 Hz, 1 H) TOF MS ES+ (M+H$^+$): 996.19; HPLC retention time=3.60 minutes.

Example 42

N-(7-(1-(1-(4'chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide

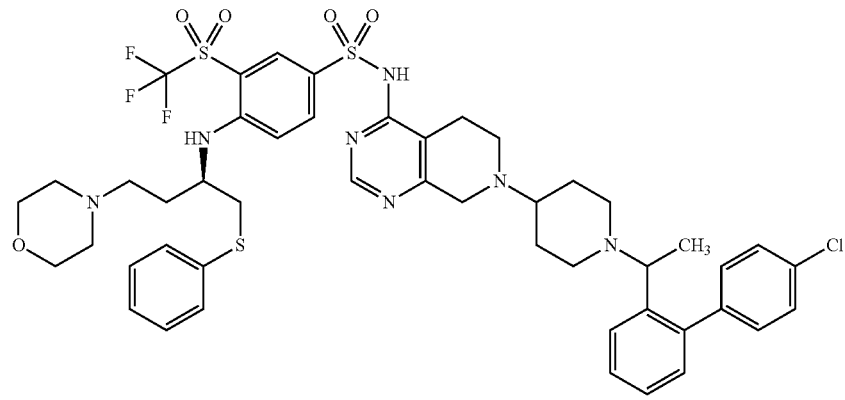 [SMILES: CC(c1ccccc1-c1ccc(Cl)cc1)N1CCC(N2CCc3c(ncnc3NS(=O)(=O)c3ccc(N[C@H](CCN4CCOCC4)CSc4ccccc4)c(S(=O)(=O)C(F)(F)F)c3)C2)CC1]

TOF MS ES+ (M+H$^+$): 984.30; HPLC Retention time=6.97 minutes.

Example 43

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide

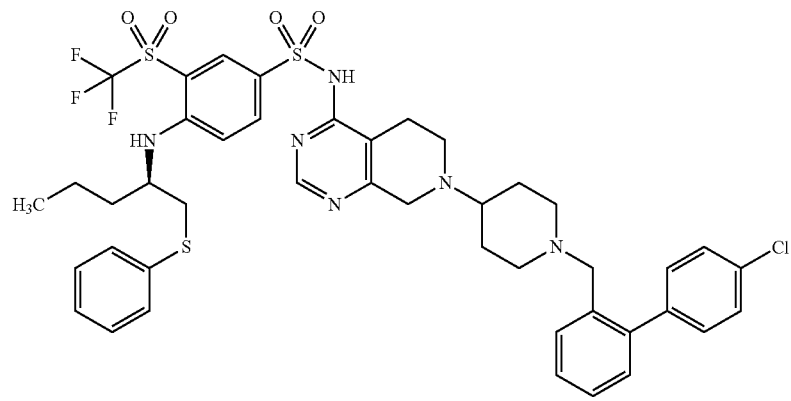 [SMILES: CCC[C@H](CSc1ccccc1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 899.25; HPLC Retention time=5.02 minutes.

Example 44

N-(7-(1((4'-chlorobiphenyl-2-yl)-methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl)benzenesulfonamide

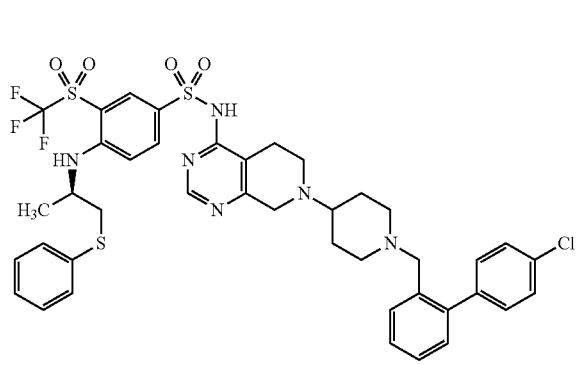 [SMILES: C[C@H](CSc1ccccc1)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 871.21; HPLC Retention time=4.75 minutes.

Example 45

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl)benzenesulfonamide

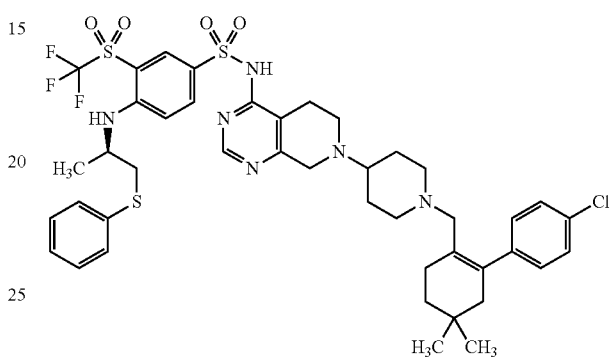

TOF MS ES+ (M+H$^+$): 903.28; HPLC retention time=5.07 minutes.

Example 46

(R)-N-(7-(1-(2-(but-2-ynyloxy)benzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

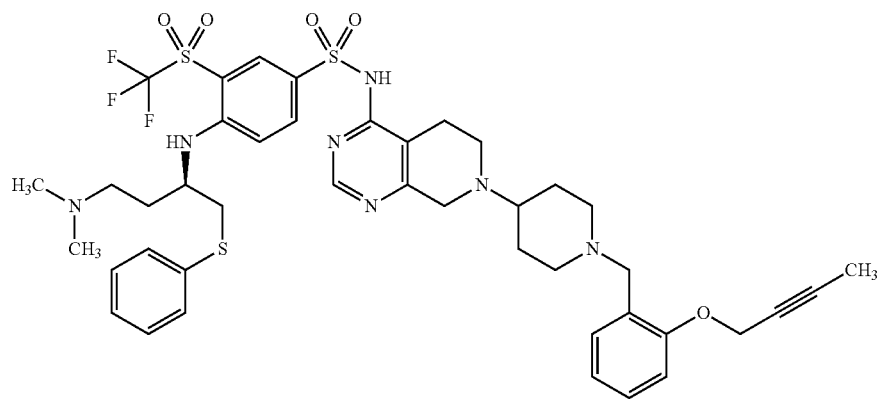 [SMILES: CC#CCOc1ccccc1CN1CCC(N2CCc3c(ncnc3NS(=O)(=O)c3ccc(N[C@H](CCN(C)C)CSc4ccccc4)c(S(=O)(=O)C(F)(F)F)c3)C2)CC1]

TOF MS ES+ (M+H$^+$): 886.31; HPLC retention time=3.07 minutes.

Example 47

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(2-fluoro-phenylsulfanylmethyl)-propylamino]-3-trifluoromethanesulfonyl-benzene sulfonamide

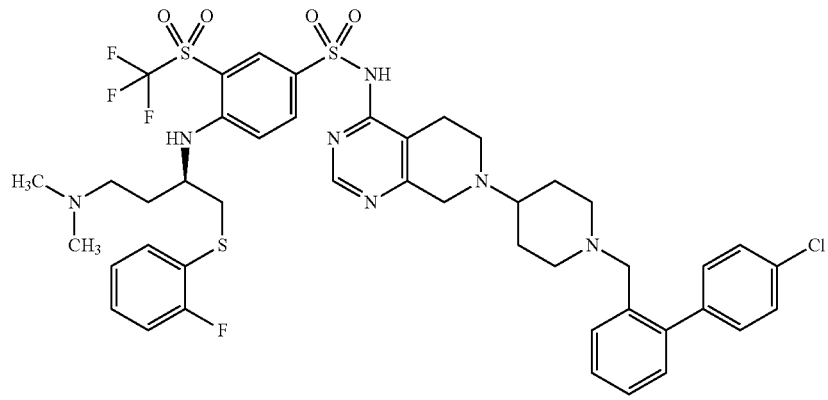 [SMILES: CN(C)CC[C@H](CSc1ccccc1F)Nc1ccc(S(=O)(=O)Nc2ncnc3c2CCN(C2CCN(Cc4ccccc4-c4ccc(Cl)cc4)CC2)C3)cc1S(=O)(=O)C(F)(F)F]

TOF MS ES+ (M+H$^+$): 946.26; HPLC retention time=3.36 minutes.

Example 48

N—[(S)-7-[1-(4'-Chloro-biphenyl-2-ylmethyl)-piperidin-4-yl]-6-methyl-5,6,7,8-tetrahydro-pyrido[3,4-d]pyrimidin-4-yl]-4-((R)-3-dimethylamino-1-phenylsulfanylmethyl-propylamino)-3 trifluoromethanesulfonyl-benzene sulfonamide

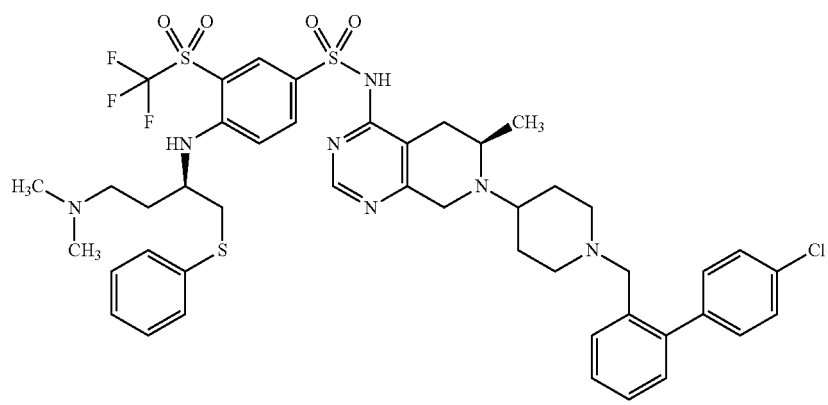 [SMILES: C[C@@H]1Cc2c(ncnc2NS(=O)(=O)c2ccc(N[C@H](CCN(C)C)CSc3ccccc3)c(S(=O)(=O)C(F)(F)F)c2)CN1C1CCN(Cc2ccccc2-c2ccc(Cl)cc2)CC1]

TOF MS ES+ (M+H$^+$): 942.29; HPLC retention time=3.42 minutes.

Example 49

N-{(R)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenyl-sulfanylmethyl-propylamino)-3-trifluoromethanesulfonyl-benzenesulfonamide

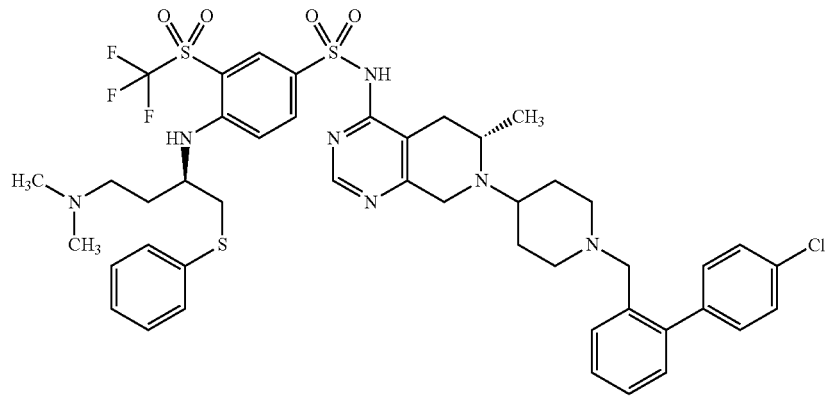 [SMILES: C[C@H]1Cc2c(ncnc2NS(=O)(=O)c2ccc(N[C@H](CCN(C)C)CSc3ccccc3)c(S(=O)(=O)C(F)(F)F)c2)CN1C1CCN(Cc2ccccc2-c2ccc(Cl)cc2)CC1]

TOF MS ES+ (M+H$^+$): 942.29; HPLC retention time=3.42 minutes.

Example 50

(R)-N-(2-chloro-7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

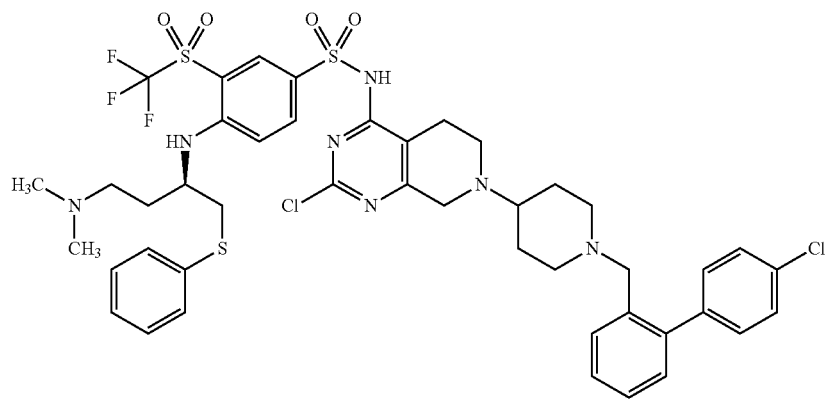 [SMILES: CN(C)CC[C@H](CSc1ccccc1)Nc1ccc(S(=O)(=O)Nc2nc(Cl)nc3c2CCN(C2CCN(Cc4ccccc4-c4ccc(Cl)cc4)CC2)C3)cc1S(=O)(=O)C(F)(F)F]

TOF MS ES+ (M+H$^+$): 962.24; HPLC retention time=3.58 minutes.

Example 51

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-(dimethylamino)-1-(phenyl thio)butan-2-ylamino)-3-(trifluoromethylsulfonyl) benzenesulfonamide

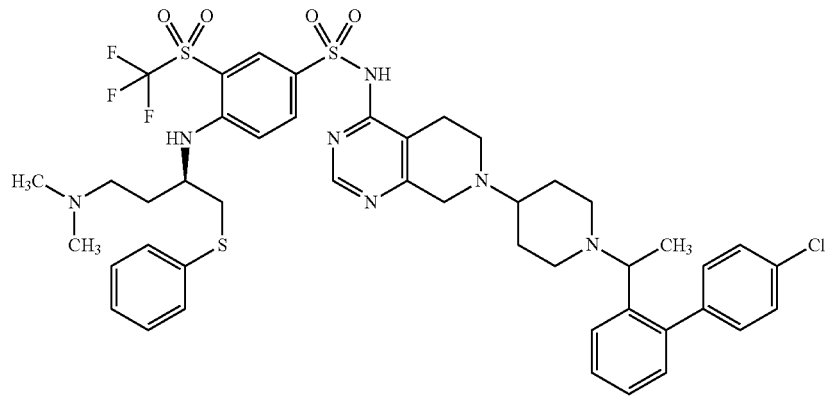 [SMILES: CC(c1ccccc1-c1ccc(Cl)cc1)N1CCC(N2CCc3c(ncnc3NS(=O)(=O)c3ccc(N[C@H](CCN(C)C)CSc4ccccc4)c(S(=O)(=O)C(F)(F)F)c3)C2)CC1]

$^1$H NMR (400 MHz, DMSO) δ 8.26 (d, J=2.02 Hz, 1H), 8.01 (s, 1H), 7.89 (dd, J=7.07, 2.02 Hz, 1H), 7.56 (d, J=8.08 Hz, 1H), 7.49 (d, 8.59 Hz, 1H), 7.40 (t, J=8.59 Hz, 1H), 7.36-7.26 (m, 7H), 7.21 (d, J=7.07 Hz, 1H), 7.15 (d, J=6.57 Hz, 1H), 6.91 (d, J=8.59 Hz, 1H), 6.77 (d, J=9.60 Hz, 1H), 3.96 (m, 2H), 3.52 (m, 2H), 2.98 (m, 2H), 2.79 (m, 2H), 2.72-2.62 (m, 3H), 2.47-2.33 (m, 8H), 1.96 (m, 1H), 1.82 (m, 1H), 1.70 (m, 1H), 1.45 (m, 1H), 1.35 (m, 1H), 1.21 (d, J=6.57 Hz, 3H); TOF MS ES+(M+H$^+$): 942.28; HPLC retention time=3.41 minutes.

Example 52

N-(7-(1((4'-chlorobiphenyl-2-yl)methyl)piperidin-4-yl)-5,6,7,8-tetrahydropyrido[3,4-d]pyrimidin-4-O-4-(2-(phenylthio)ethylamino)-3-(trifluoromethylsulfonyl) benzenesulfonamide

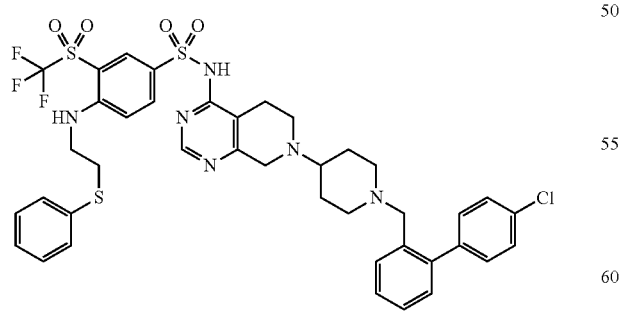

TOF MS ES+ (M+H$^+$): 857.20; HPLC retention time=4.62 minutes.

Example 53

(R)-N-(7-(1((4'-chlorobiphenyl)-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethyl)benzenesulfonamide

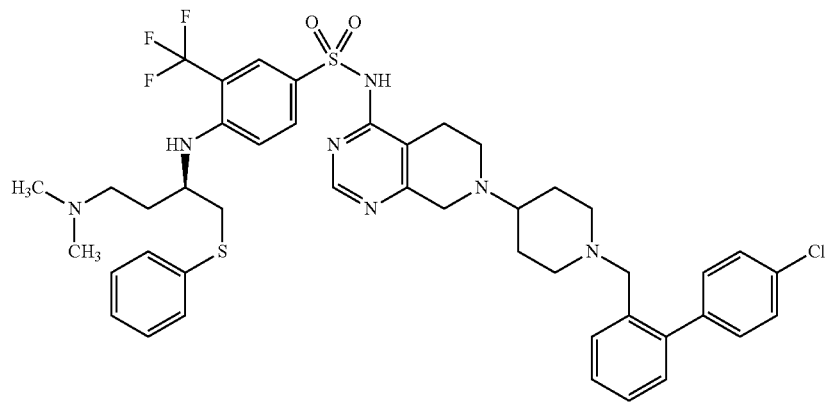 [SMILES: CN(C)CC[C@H](CSc1ccccc1)Nc1ccc(S(=O)(=O)Nc2ncnc3c2CCN(C2CCN(Cc4ccccc4-c4ccc(Cl)cc4)CC2)C3)cc1C(F)(F)F]

TOF MS ES+ (M+H$^+$): 864.31; HPLC retention time=3.26 minutes.

Example 54

(R)-N-(7-(1-((4'-chlorobiphenyl-2-yl)methyl)piperidin-4-yl)-5,6,7,8-tetrahydropyrido[3,4-d]pyrimidin-4-yl)-3-cyano-4-(4-(dimethylamino)-1-(phenylthio)butan-2-ylamino)benzenesulfonamide

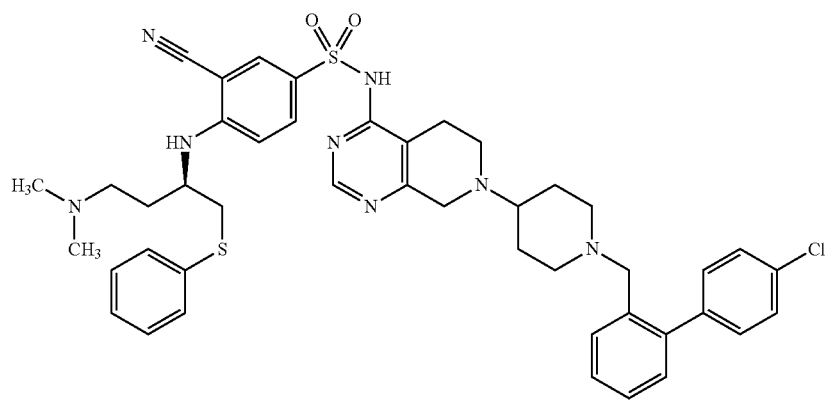 [SMILES: CN(C)CC[C@H](CSc1ccccc1)Nc1ccc(S(=O)(=O)Nc2ncnc3c2CCN(C2CCN(Cc4ccccc4-c4ccc(Cl)cc4)CC2)C3)cc1C#N]

TOF MS ES+ (M+H$^+$): 821.32; HPLC retention time=105 minutes.

Example 55

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide

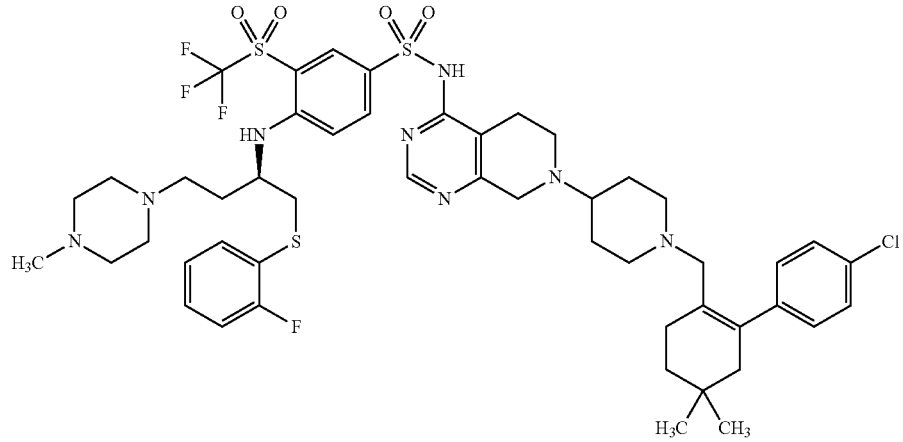 [SMILES: CN1CCN(CC[C@H](CSc2ccccc2F)Nc2ccc(S(=O)(=O)Nc3ncnc4c3CCN(C3CCN(CC5=C(c6ccc(Cl)cc6)CC(C)(C)CC5)CC3)C4)cc2S(=O)(=O)C(F)(F)F)CC1]

$^1$H NMR (400 MHz, MeOD) δ ppm 1.01 (s, 6 H) 1.46-1.58 (m, 2 H) 1.60-1.82 (m, 3 H) 1.87-1.99 (m, 2 H) 1.99-2.13 (m, 3 H) 2.13-2.31 (m, 4 H) 2.31-2.76 (m, 16 H) 2.81 (t, J=5.81 Hz, 2 H) 3.06-3.27 (m, 6 H) 3.55 (s, 2 H) 3.98 (dd, J=8.59, 4.55 Hz, 1H) 630-6.84 (m, 1 H) 6.96-7.13 (m, 4 H) 7.17-7.29 (m, 1 H) 7.29-7.43 (m, 3 H) 7.97 (dd, J=9.09, 2.02 Hz, 1 H) 8.13 (s, 1 H) 8.34 (d, J=2.53 Hz, 1 H) TOF MS ES+(M+H$^+$): 1033.37; HPLC retention time=3.74 minutes.

Example 56

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide

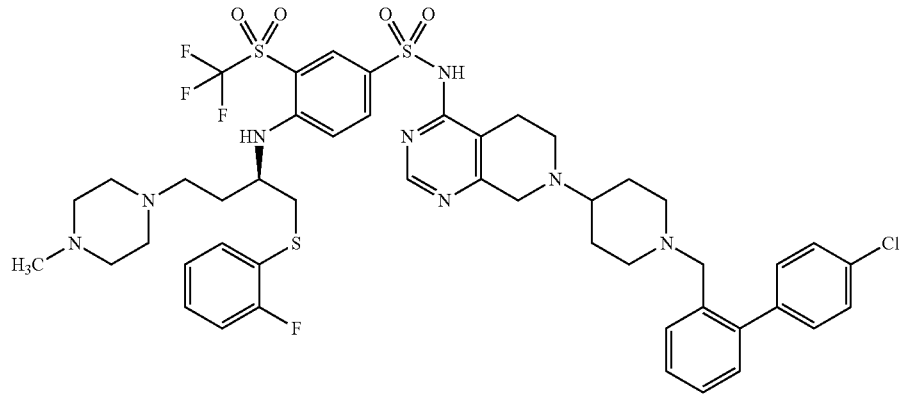 [SMILES: CN1CCN(CC[C@H](CSc2ccccc2F)Nc2ccc(S(=O)(=O)Nc3ncnc4c3CCN(C3CCN(Cc5ccccc5-c5ccc(Cl)cc5)CC3)C4)cc2S(=O)(=O)C(F)(F)F)CC1]

$^1$H NMR (400 MHz, MeOD) δ ppm 1.47-1.67 (m, 2 H) 1.73 (d, J=6.06 Hz, 1 H) 1.87 (br. s., 2 H) 2.04 (t, J=10.86 Hz, 3 H) 2.28-2.82 (m, 16 H) 2.83-3.01 (m, 4 H) 3.04-3.26 (m, 2 H) 3.58 (d, J=17.68 Hz, 4 H) 3.89-4.05 (m, 1 H) 6.70-6.85 (m, 2 H) 6.95-7.11 (m, 2 H) 7.17-7.30 (m, 2 H) 7.30-7.47 (m, 6 H) 7.47-7.59 (m, 1 H) 7.97 (dd, J=9.35, 2.27 Hz, 1 H) 8.13 (s, 1 H) 8.33 (d, J=2.02 Hz, 1 H) TOF MS ES+ (M+H$^+$): 1001.31; HPLC retention time=143 minutes.

Example 57

N-{7-[1-(4'-Fluoro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonyl-benzenesulfonamide

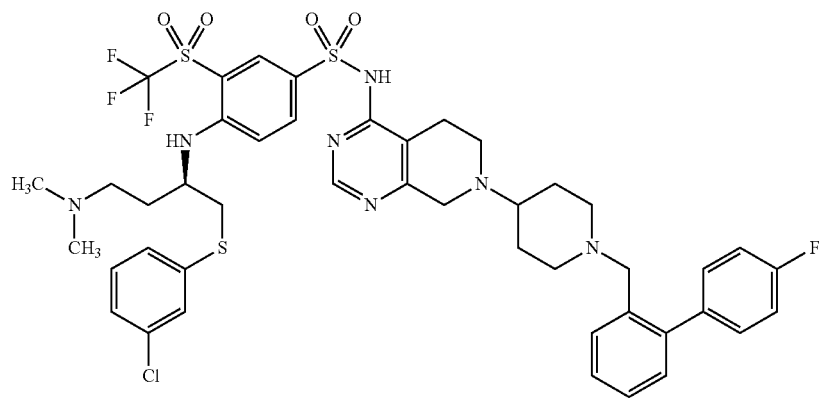 [SMILES: CN(C)CC[C@H](CSc1cccc(Cl)c1)Nc1ccc(S(=O)(=O)Nc2ncnc3c2CCN(C2CCN(Cc4ccccc4-c4ccc(F)cc4)CC2)C3)cc1S(=O)(=O)C(F)(F)F]

TOF MS ES+ (M+H$^+$): 946.27; HPLC retention time=3.36 minutes.

Example 58

(R)-N-(7-yl)-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-nitrobenzenesulfonamide

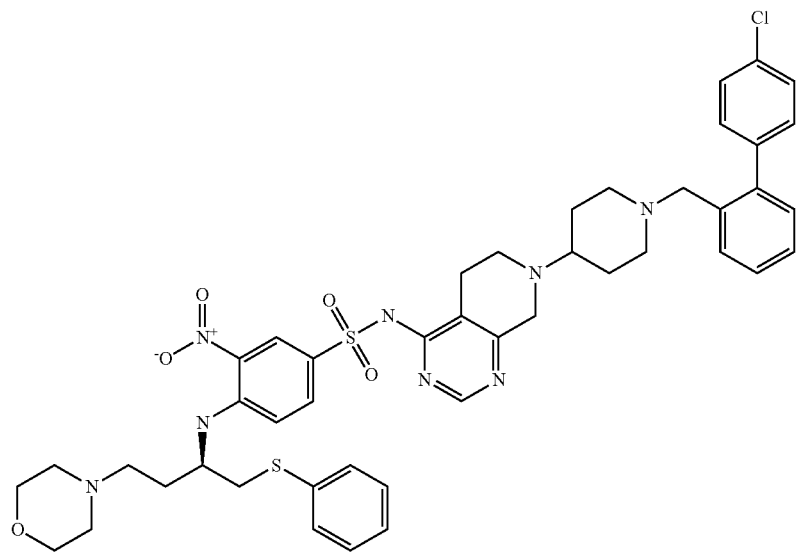

TOF MS ES+ (M+H+): 883.32 HPLC retention time 4.76 minutes.

Example 59

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide

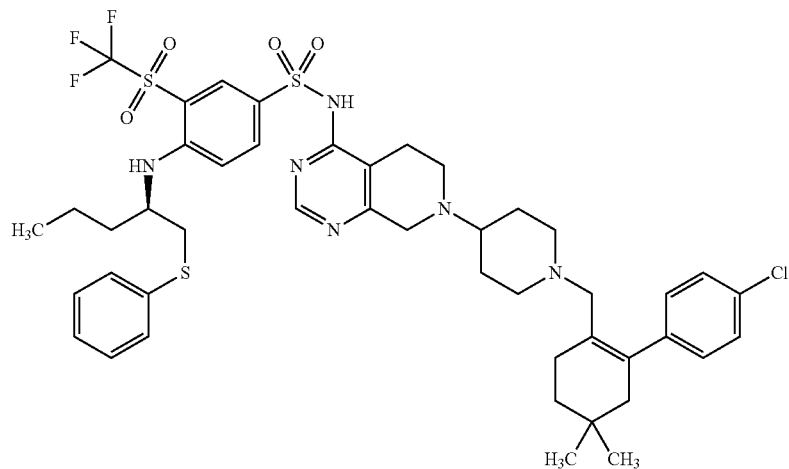 [SMILES: CCC[C@H](CSc1ccccc1)Nc1ccc(S(=O)(=O)Nc2ncnc3c2CCN(C2CCN(CC4=C(c5ccc(Cl)cc5)CC(C)(C)CC4)CC2)C3)cc1S(=O)(=O)C(F)(F)F]

TOF MS ES+ (M+H+): 931.31; HPLC retention time=5.33 minutes.

Example 60

(R)-N-(7-(4-((4'-chlorobiphenyl-2-yl)methyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

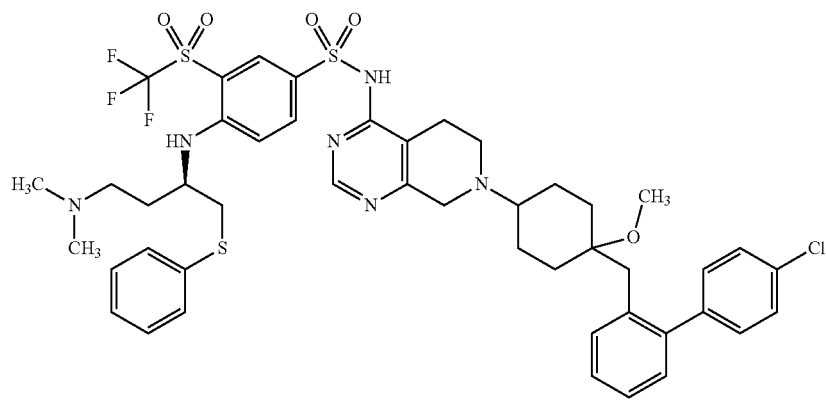 [SMILES: COC1(Cc2ccccc2-c2ccc(Cl)cc2)CCC(N2CCc3c(ncnc3NS(=O)(=O)c3ccc(N[C@H](CCN(C)C)CSc4ccccc4)c(S(=O)(=O)C(F)(F)F)c3)C2)CC1]

¹H NMR (400 MHz, CHLOROFORM-d) δ ppm 8.22 (dd, J=17.0, 2.0 Hz, 1 H), 7.98-8.12 (m, 1 H), 7.74 (dd, J=10.0, 2.5 Hz, 1 H), 7.53-7.68 (m, 1 H), 7.38 (d, J=7.5 Hz, 1 H,) 7.11-7.36 (m, 10 H), 7.09 (t, J=7.5 Hz, 1 H), 6.43 (dd, J=17.0, 10.0 Hz, 1 H), 3.73-3.86 (m, 1 H), 3.53 (br. s., 1 H), 3.33 (s, 1 H), 3.12 (s, 1 H), 2.88-3.09 (m, 4 H), 2.71-2.86 (m, 2 H), 2.67 (br, s., 1 H), 2.40 (br. s., 2 H), 2.10-2.36 (m, 7 H), 1.92-2.08 (m, 1 H), 1.66-1.80 (m, 1 H), 1.37-1.59 (m, 4 H), 1.33 (t, J=7.5 Hz, 2 H), 1.14-1.29 (m, 3 H), 0.90 (d, J=3.5 Hz, 2 H); TOF MS ES+ (M+H⁺): 957.29; HPLC retention times=cis/trans mixture: 3.96 and 4.02 minutes.

2.01-2.16 (m, 1 H), 1.17-1.98 (m, 14 H); TOF MS ES+ (M+H⁺): 925.21; HPLC retention time=3.67 minutes.

Example 62

N-(7-(4-((4'-chlorobiphenyl-2-yl)methylene)cyclo-hexyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide

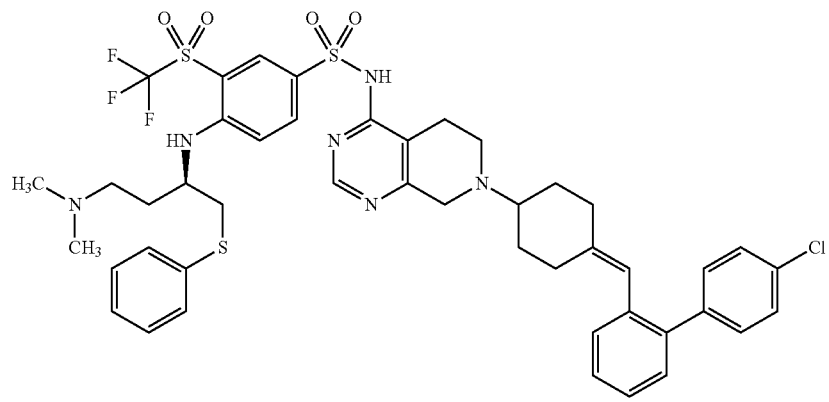

¹H NMR (400 MHz, CHLOROFORM-d) δ ppm 8.26 (s, 1 H), 8.10 (s, 1 H), 7.81 (dd, J=9.0, 2.01 Hz, 1 H), 7.57-7.75 (m, 1 H), 7.13-7.44 (m, 12 H), 6.48 (d, J=9.0 Hz, 1 H), 6.03 (s, 1 H), 3.77-3.95 (m, 1 H), 3.61 (s, 2 H), 2.90-3.15 (m, 2 H), 2.43-2.80 (m, 6 H), 1.85-2.41 (m, 10 H), 1.76 (t, J=11.0 Hz, 4 H), 1.26-1.48 (m, 2 H), 0.90-1.10 (m, 1 H); TOF MS ES+ (M+H⁺): 925.26; HPLC retention time=6.71 minutes.

Example 61

(R)-N-(7-(4-(2-bromobenzyl)-4-methoxycyclo-hexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

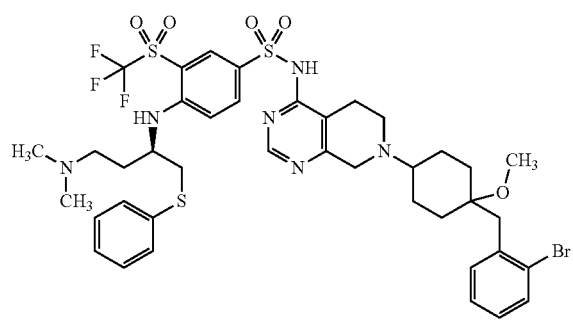 [SMILES: COC1(Cc2ccccc2Br)CCC(N2CCc3c(ncnc3NS(=O)(=O)c3ccc(N[C@H](CCN(C)C)CSc4ccccc4)c(S(=O)(=O)C(F)(F)F)c3)C2)CC1]

¹H NMR (400 MHz, CHLOROFORM-d) δ ppm 8.27-8.38 (m, 1 H), 8.07-8.20 (m, 1 H), 7.79-7.93 (m, 1 H), 7.61-7.79 (m, 1 H,) 7.49-7.60 (m, 1 H), 7.18-7.48 (m, 6 H), 7.10-7.05 (m, 1 H), 6.51 (d, J=10.0 Hz, 1 H), 3.82-4.02 (m, 1 H), 3.59-3.72 (m, 2 H), 3.26-3.41 (m, 2 H), 2.93-3.15 (m, 3 H), 2.79 (d, J=13.5 Hz, 2 H), 2.58 (d, Hz, 3 H), 2.26 (br. s., 5 H),

Example 63

N-(7-(4-benzylidenecyclohexyl)-5,6,7,8-tetrahydro-pyrido[3,4-d]pyrimidin-4-yl)-4-((R)-4-(dimethy-lamino)-1-(phenylthio)butan-2-ylamino)-3 trifluo-romethylsulfonyl)benzenesulfonamide

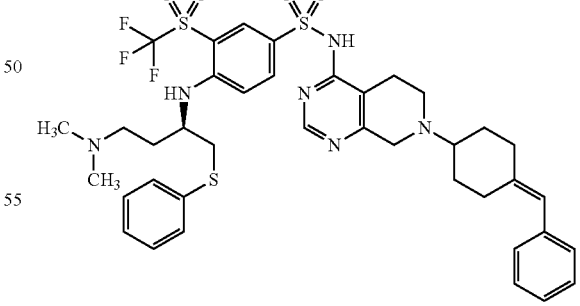

¹H NMR (400 MHz, CHLOROFORM-d) δ ppm 8.26 (s, 1 H), 8.10 (s, 1 H), 7.74-7.90 (m, 1 H), 7.04-7.46 (m, 9 H), 6.45 (d, J=9.0 Hz, 1 H), 6.24 (s, 1 H), 3.81 (d, J=3.51 Hz, 1 H), 3.63 (s, 2 H), 2.86-3.15 (m, 3 H), 2.78 (br. s., 3 H), 2.56 (br. s., 2 H), 2.36-2.50 (m, 2 H), 2.09-2.33 (m, 8 H), 1.84-2.08 (m, 5 H), 1.66-1.82 (m, 1 H), 1.30-1.61 (m, 2 H); TOF MS ES+ (M+H⁺): 815.27; HPLC retention time=3.64 minutes.

Example 64

(R)-N-(7-(4-((4'-chlorobiphenyl-2-yl)methyl)-4-hydroxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

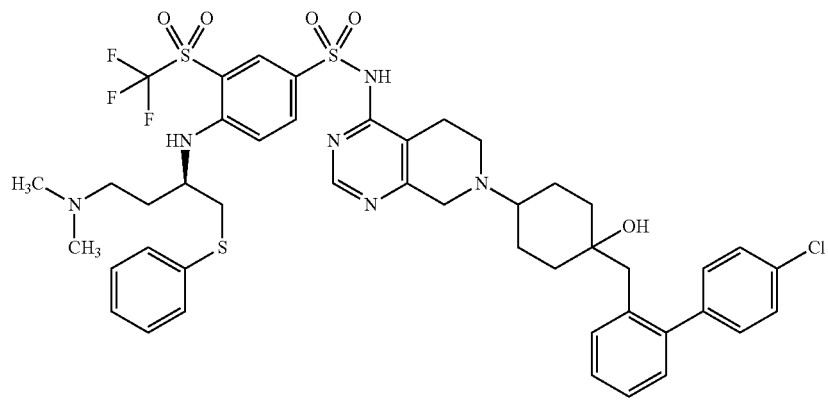 [SMILES: CN(C)CC[C@H](CSc1ccccc1)Nc1ccc(S(=O)(=O)Nc2ncnc3c2CCN(C2CCC(O)(Cc4ccccc4-c4ccc(Cl)cc4)CC2)C3)cc1S(=O)(=O)C(F)(F)F]

TOF MS ES+ (M+H$^+$): 943.27; HPLC retention times=cis/trans mixture: 3.70 and 3.81 minutes.

General Reductive Amination Procedure 3.

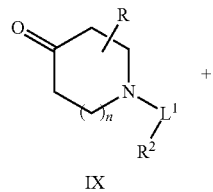

IX

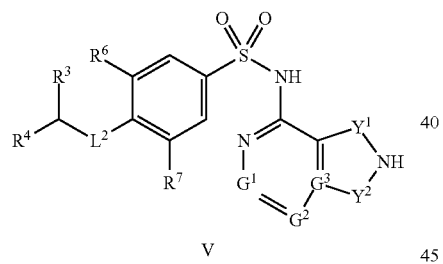

V

Amine V (1 eq) and ketone IX (1.2 eq) were dissolved in DCE (10 mL/mmol V), and NaHCO$_3$ (6 eq) was added. The reaction was stirred at ambient temperature for 3 hours, and then heated to 65° C. for 3 hours. Na(AcO)$_3$BH (3 eq) was then added, and the reaction was stirred at 65° C. for 16 hours. The reaction was diluted with CH$_2$Cl$_2$, washed with water followed by brine, dried over Na$_2$SO$_4$, filtered and concentrated. The crude residue was purified by flash chromatography on silica gel (0-10% methanol/CH$_2$Cl$_2$ followed by 20% 7N NH$_3$ in methanol/CH$_2$Cl$_2$).

Example 65

N-(7-(1((4'-Chlorobiphenyl-2-yl)methyl)-3-fluoropiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide

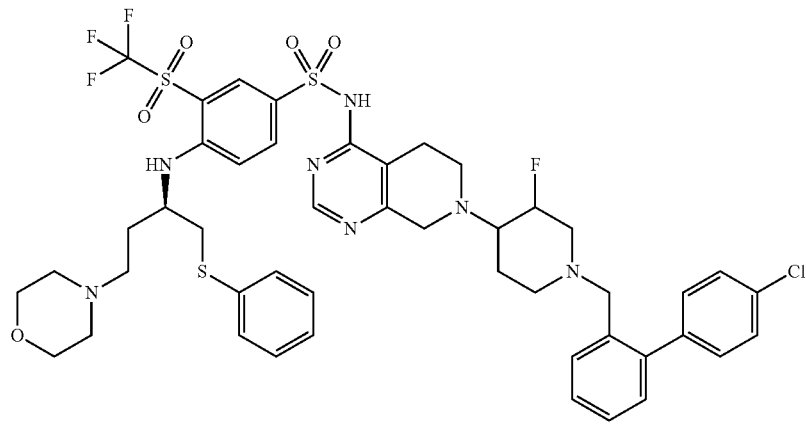 [SMILES: O=S(=O)(Nc1ncnc2c1CCN(C1CCN(Cc3ccccc3-c3ccc(Cl)cc3)CC1F)C2)c1ccc(N[C@H](CCN2CCOCC2)CSc2ccccc2)c(S(=O)(=O)C(F)(F)F)c1]

Following General Reductive Amination Procedure 2, (R)-4-(4-Morpholino-1-(phenylthio)butan-2-ylamino)-N-(5,6,7,8-tetrahydropyrido[3,4-d]pyrimidin-4-yl)-3-(trifluoromethylsulfonyl)benzenesulfonamide (34 mg, 0.05 mmol) and 1-((4'-chlorobiphenyl-2-yl)methyl)-3-fluoropiperidin-4-one (19 mg, 0.059 mmol) afforded the title compound (6 mg, 12% yield).

$^1$H NMR (400 MHz, CDCl$_3$) δ ppm 1.22 (m, 1H), 1.48-1.77 (m, 3H), 1.83-2.15 (m, 4H), 2.18-2.60 (m, 8H), 2.76-3.16 (m, 5H), 3.21-3.45 (m, 2H), 3.51-3.94 (m, 6H), 4.69-4.97 (m, 1H), 6.52 (d, J=9.60 Hz, 1H), 6.92 (d, J=8.59 Hz, 1H), 7.10-7.51 (m, 13H), 7.79 (dd, J=9.09, 2.02 Hz, 1H), 8.06 (br. s., 1H), 8.22 (br. s., 1H).

MS [M+H]$^+$=988.27

HPLC retention time: 3.66 minutes (Agilent 1100 HPLC system; Inertsil ODS3 100×3 mm C18 column; flow rate 1 mL/minute; 5-95% ACN/water with 0.1% formic acid; 7.75 minute run)

Examples 66-72 were prepared by reductive amination of ketones IX with amines V following General Procedure 3 above.

Example 66

N-(7-(1-((4'-chlorobiphenyl-2-yl)methyl)-3-fluoropiperidin-4-yl)-5,6,7,8tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide

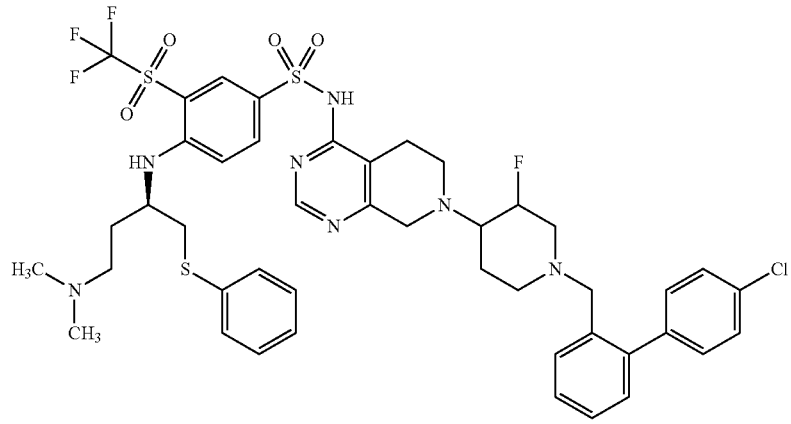 [SMILES: CN(C)CC[C@H](CSc1ccccc1)Nc1ccc(S(=O)(=O)Nc2ncnc3c2CCN(C2CCN(Cc4ccccc4-c4ccc(Cl)cc4)CC2F)C3)cc1S(=O)(=O)C(F)(F)F]

$^1$H NMR (400 MHz, ACETONITRILE-d$_3$) δ ppm 8.07-8.14 (m, 2H), 7.83 (dd, J=9.09, 2.02 Hz, 1H), 7.22-7.40 (m, 9H), 7.06-7.19 (m, 4H), 6.89 (d, J=9.09 Hz, 1H), 6.80 (d, J=9.60 Hz, 1H), 4.69-4.93 (m, 1H), 3.99 (dd, J=8.59, 5.05 Hz, 1H), 3.58 (s, 2H), 3.20-3.32 (m, 2H), 3.04-3.20 (m, 2H), 2.85-2.97 (m, 1H), 2.65-2.85 (m, 5H), 2.44 (s, 6H), 2.38 (t, J=5.81 Hz, 2H), 1.88-2.16 (m, 4H), 1.74-1.84 (m, 1H), 1.56 (d, J=12.63 Hz, 1H); MS [M+H]$^+$: 946.26.

Example 67

(R)-N-(7-(1((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

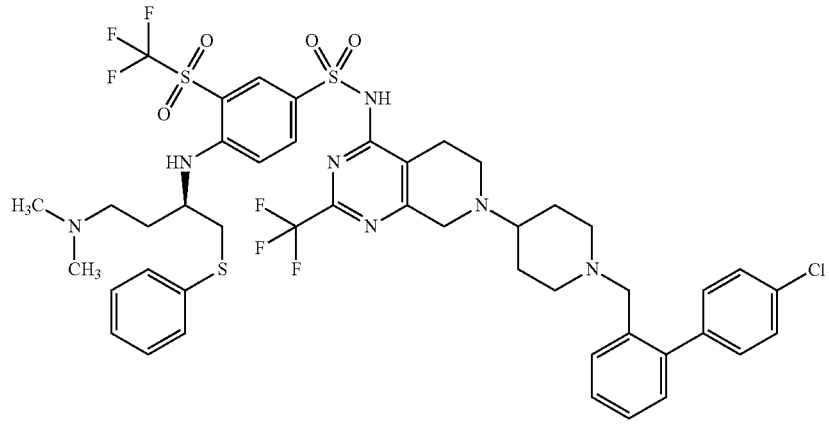 [SMILES: CN(C)CC[C@H](CSc1ccccc1)Nc1ccc(S(=O)(=O)Nc2nc(C(F)(F)F)nc3c2CCN(C2CCN(Cc4ccccc4-c4ccc(Cl)cc4)CC2)C3)cc1S(=O)(=O)C(F)(F)F]

$^1$H NMR (400 MHz, ACETONITRILE-$d_3$) δ ppm 8.11 (d, J=2.02 Hz, 1H), 8.01-8.06 (m, 1H), 7.44-7.49 (m, 1H), 7.39-7.43 (m, 3H), 7.28-7.37 (m, 4H), 7.16-7.26 (m, 4H), 7.05 (d, J=8.59 Hz, 1H), 6.61 (d, J=9.09 Hz, 1H), 3.84-3.94 (m, 1H), 3.48 (s, 2H), 3.34 (s, 2H), 3.13 (d, J=6.06 Hz, 2H), 2.78 (d, J=11.62 Hz, 2H), 2.72 (t, J=5.81 Hz, 2H), 2.52-2.60 (m, 1H), 2.46-2.52 (m, 2H), 2.32-2.42 (m, 2H), 2.23 (s, 6H), 2.11 (dd, J=5.05, 2.53 Hz, 1H), 1.89 (d, J=10.61 Hz, 1H), 1.71-1.80 (m, 4H), 1.41-1.53 (m, 2H); MS (ESI) ink (M+H)$^+$=996.26.

Example 68

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide

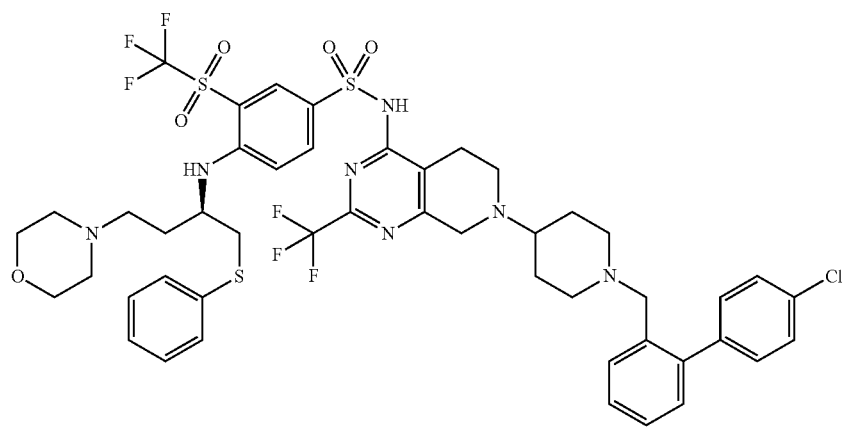 [SMILES: O=S(=O)(Nc1nc(C(F)(F)F)nc2c1CCN(C1CCN(Cc3ccccc3-c3ccc(Cl)cc3)CC1)C2)c1ccc(N[C@H](CCN2CCOCC2)CSc2ccccc2)c(S(=O)(=O)C(F)(F)F)c1]

$^1$H NMR (400 MHz, ACETONITRILE-$d_3$) δ ppm 8.12 (d, J=2.02 Hz, 1H), 8.02-8.07 (m, 1H), 7.50-7.55 (m, 1H), 7.39-

7.47 (m, 4H), 7.32-7.39 (m, 4H), 7.18-7.30 (m, 4H), 6.75 (d, J=9.09 Hz, 1H), 6.68 (d, J=8.59 Hz, 1H), 3.95-4.07 (m, 1H), 3.58 (s, 2H), 3.18 (dd, J=6.06, 4.04 Hz, 2H), 2.83-2.93 (m, 4H), 2.57 (br. s., 4H), 2.24-2.39 (m, 8H), 2.13-2.21 (m, 2H), 2.01-2.08 (m, 1H), 1.77-1.88 (m, 4H), 1.54-1.68 (m, 4H), 1.26-1.33 (m, 1H); MS (ESI) m/e (M+H)$^+$=1038.28.

Example 69

N-(7-(1-((4'-chlorobiphenyl-2-yl)methyl)-3-fluoropiperidin-4-yl)-2-(trifluoromethyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide

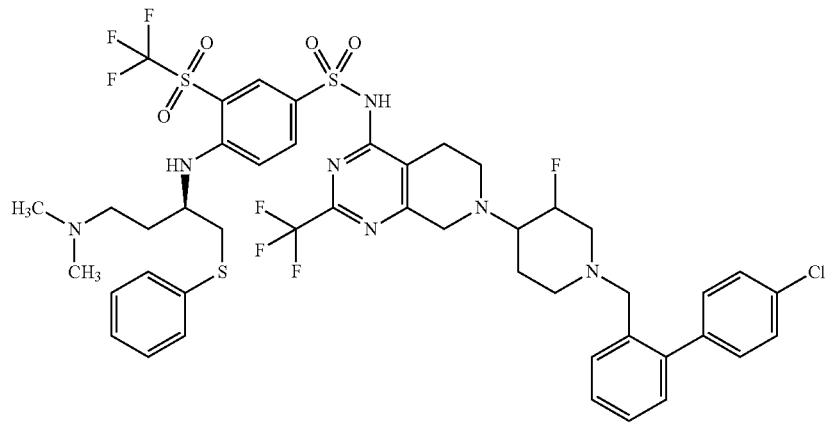 [SMILES: CN(C)CC[C@H](CSc1ccccc1)Nc1ccc(S(=O)(=O)Nc2nc(C(F)(F)F)nc3c2CCN(C2CCN(Cc4ccccc4-c4ccc(Cl)cc4)CC2F)C3)cc1S(=O)(=O)C(F)(F)F]

$^1$H NMR (400 MHz, ACETONITRILE-d$_3$) δ ppm 8.10 (d, J=2.02 Hz, 1H), 7.44-7.50 (m, 3H), 7.39-7.44 (m, 2H), 7.30-7.39 (m, 4H), 7.18-7.28 (m, 4H), 7.08 (d, J=8.08 Hz, 1H), 6.61 (d, J=9.09 Hz, 1H), 4.91 (d, J=50.53 Hz, 1H), 3.83-3.95 (m, 1H), 3.57 (s, 2H), 3.25-3.38 (m, 2H), 3.10-3.18 (m, 2H), 2.95-3.06 (m, 1H), 2.77-2.91 (m, 3H), 2.27-2.55 (m, 8H), 2.18-2.23 (m, 6H), 2.08-2.14 (m, 1H), 1.98-2.04 (m, 1H), 1.83-1.91 (m, 1H), 1.72-1.80 (m, 1H), 1.69 (br. s., 1H); MS (ESI) m/e (M+H)$^+$=1014.25.

Example 70

(R)-N-(7-yl)-(1-((2-(4-chlorophenyl)-5,5-dimethyl-cyclohex-1-enyl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide

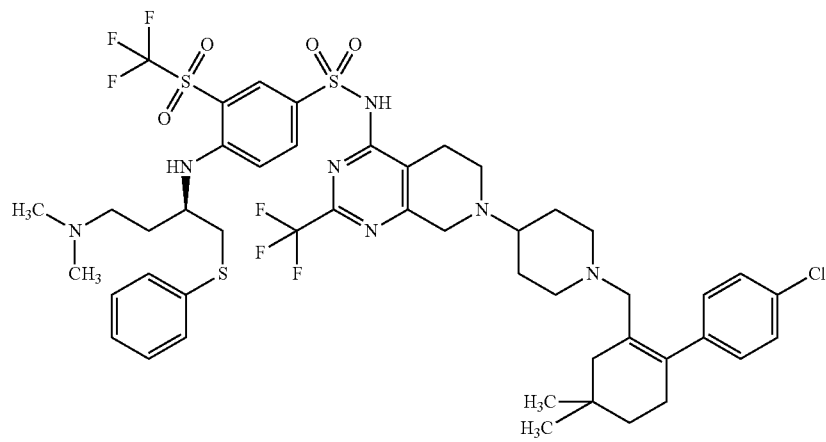 [SMILES: CN(C)CC[C@H](CSc1ccccc1)Nc1ccc(S(=O)(=O)Nc2nc(C(F)(F)F)nc3c2CCN(C2CCN(CC4=C(c5ccc(Cl)cc5)CCC(C)(C)C4)CC2)C3)cc1S(=O)(=O)C(F)(F)F]

¹H NMR (400 MHz, ACETONITRILE-d₃) δ ppm 8.13 (d, J=2.53 Hz, 1 H), 8.02-8.06 (m, 1H), 7.31-7.37 (m, 4H), 7.17-7.26 (m, 3H), 7.08 (d, J=8.59 Hz, 2H), 7.01 (d, J=8.59 Hz, 1H), 6.62 (d, J=9.09 Hz, 1H), 3.83-3.94 (m, 1H), 3.47 (s, 2H), 3.03-3.16 (m, 6H), 2.57-2.68 (m, 3H), 2.41-2.50 (m, 4H), 2.30 (s, 6H), 2.23-2.28 (m, 2H), 2.08-2.18 (m, 1H), 1.99 (br. s., 2H), 1.65-1.87 (m, 6H), 1.44 (t, J=6.57 Hz, 2H), 1.25-1.34 (m, 2H), 0.95 (s, 6H); MS (ESI) m/e (M+H)⁺=1028.33.

Example 71

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-nitrobenzenesulfonamide

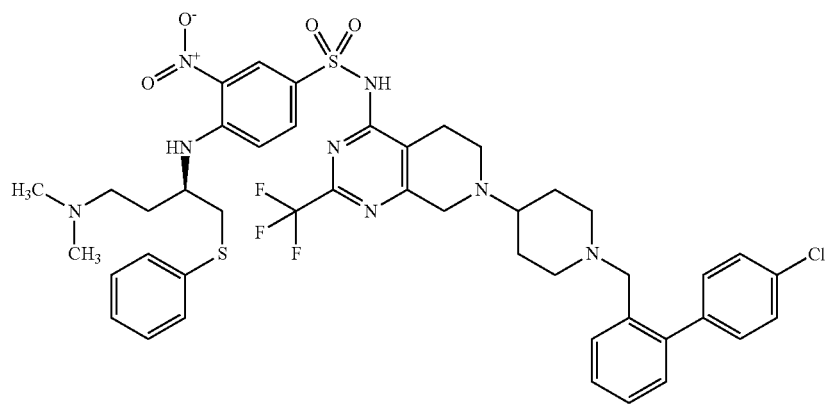 [SMILES: CN(C)CC[C@H](CSc1ccccc1)Nc1ccc(S(=O)(=O)Nc2nc(C(F)(F)F)nc3c2CCN(C2CCN(Cc4ccccc4-c4ccc(Cl)cc4)CC2)C3)cc1[N+](=O)[O-]]

¹H NMR (400 MHz, ACETONITRILE-d₃) δ ppm 8.61 (d, J=2.0 Hz, 1H), 8.31-8.34 (d, J=10.0 Hz, 1H), 7.88-7.91 (d, J=11.6 Hz, 1H), 7.15-7.57 (m, 12H), 6.71 (d, J=9.5 Hz, 1H), 3.99-4.04 (m, 1H), 3.48 (s, 2H), 3.34 (s, 2H), 3.17-3.23 (m, 2H), 2.56-2.82 (m, 7H), 2.49-2.53 (m, 2H), 2.36 (s, 6H), 2.07-2.27 (m, 1H), 1.71-1.76 (m, 5H), 1.46-1.52 (m, 2H); MS (ES1) m/e (M+H)⁺=909.30.

Example 72

(R)-N-(6-(1-((4'-chlorobiphenyl-2-yl)methyl)piperidin-4-yl)-6,7-dihydro-5H-pyrrolo[3,4-d]pyrimidin-4-yl)-4-(4-morpholino-1-(phenylthio)butan-2-ylamino)-3-(trifluoromethylsulfonyl)benzenesulfonamide

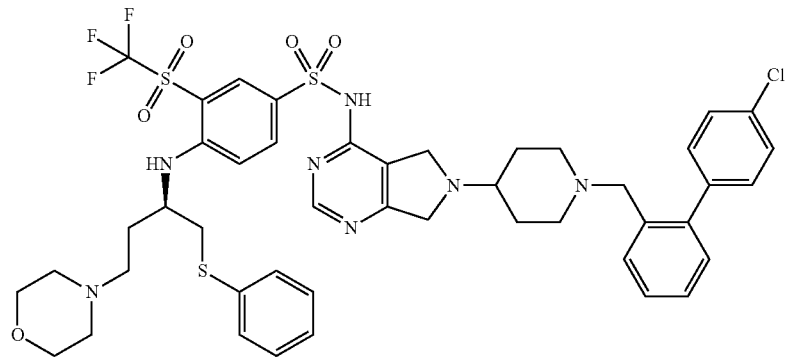 [SMILES: O=S(=O)(Nc1ncnc2c1CN(C1CCN(Cc3ccccc3-c3ccc(Cl)cc3)CC1)C2)c1ccc(N[C@H](CCN2CCOCC2)CSc2ccccc2)c(S(=O)(=O)C(F)(F)F)c1]

$^1$H NMR (400 MHz, MeOD) δ ppm 8.35 (d, J=2.02 Hz, 1H), 8.24 (s, 1H), 7.96 (dd, J=9.22, 2.15 Hz, 1H), 7.56-7.62 (m, 1H), 7.42-7.49 (m, 4H), 7.33-7.37 (m, 4H), 7.28-7.32 (m, 1H), 7.16-7.27 (m, 3H), 6.83 (d, J=8.84 Hz, 1H), 6.74 (d, J=9.35 Hz, 1H), 3.90 (br. s., 6H), 3.57-3.65 (m, 4H), 3.43-3.50 (m, 1H), 3.09-3.26 (m, 3H), 2.98-3.08 (m, 2H), 2.67-2.76 (m, 1H), 2.26-2.48 (m, 7H), 1.94-2.13 (m, 3H), 1.55-1.78 (m, 3H), 1.27-1.33 (m, 1H); MS (ESI) m/e (M+H)$^+$ =956.27.

General Reductive Amination Procedure 4.

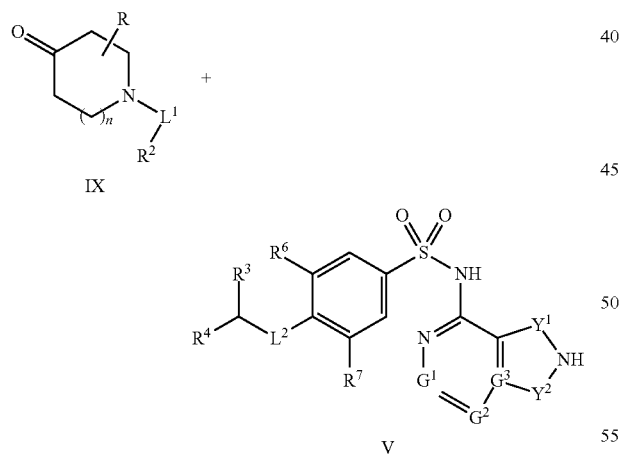

A solution of amine V (1 eq), ketone IX (1 eq), acetic acid (1 eq), sodium triacetoxyborodeuturide (1.5 eq) and molecular sieves (~400 mg/mmol V) in DCE (12.4 mL/mmol V) was stirred at 45° C. for 12 hours. The mixture was cooled to room temperature, filtered through Celite, and concentrated. The crude residue was purified by flash chromatography on silica gel (0-100% methanol in CH$_2$Cl$_2$).

Examples 73-91 were prepared using the general reductive amination procedure 4 described above.

Example 73

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzene sulfonamide

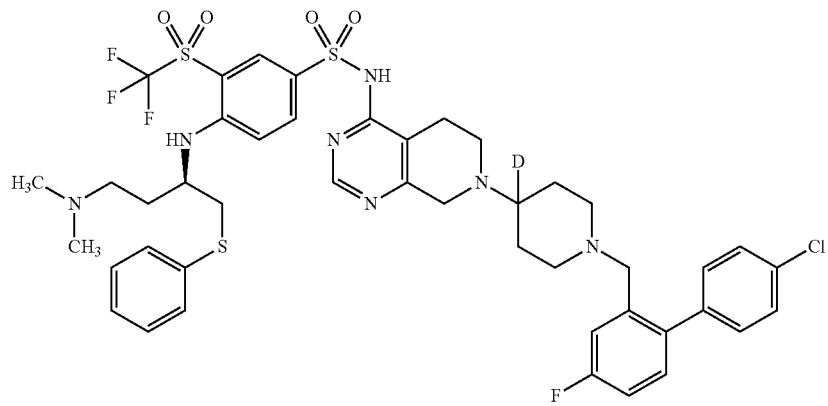 [SMILES: [2H]C1(N2CCc3c(ncnc3NS(=O)(=O)c3ccc(N[C@H](CCN(C)C)CSc4ccccc4)c(S(=O)(=O)C(F)(F)F)c3)C2)CCN(Cc2cc(F)ccc2-c2ccc(Cl)cc2)CC1]

TOF MS ES+ (M+H+): 947.27; HPLC retention time=3.45 minutes.

Example 74

N-(7-(1-((S)-1-(4'-chlorobiphenyl-2-yl)ethyl)-4-deuteropiperidin-4-yl)-2-(trifluoromethyl)-5,6,7,8-tetrahydropyrido[3,4-d]pyrimidin-4-yl)-4-((R)-1-(2-fluorophenylthio)-4-(4-methylpiperazin-1-yl)butan-2-ylamino-3-(trifluoromethylsulfonyl)benzenesulfonamide

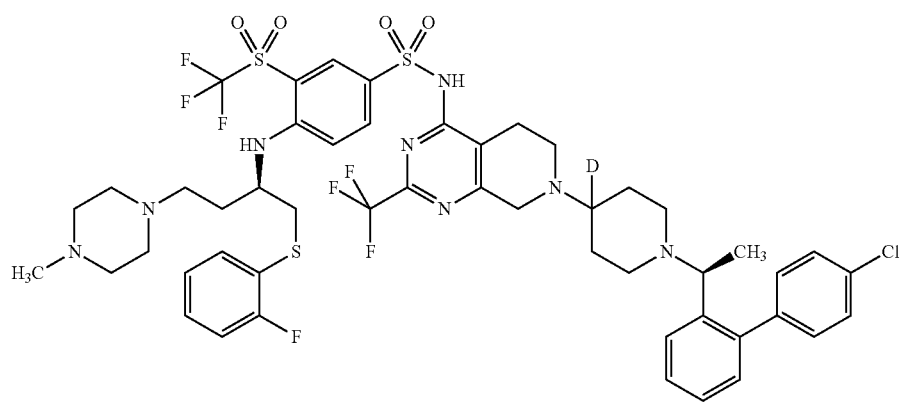 [SMILES: [2H]C1(N2CCc3c(nc(C(F)(F)F)nc3NS(=O)(=O)c3ccc(N[C@H](CCN4CCN(C)CC4)CSc4ccccc4F)c(S(=O)(=O)C(F)(F)F)c3)C2)CCN([C@@H](C)c2ccccc2-c2ccc(Cl)cc2)CC1]

TOF MS ES+ (M+H+): 1048.32; HPLC retention time=3.89 minutes.

Example 75

(R)-N-(7-(1-((2-(4-chlorophenyl)-4,4-dimethylcyclohex-1-enyl)methyl)-4-deuteropiperidin-4-yl)-2-(dimethylamino)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide

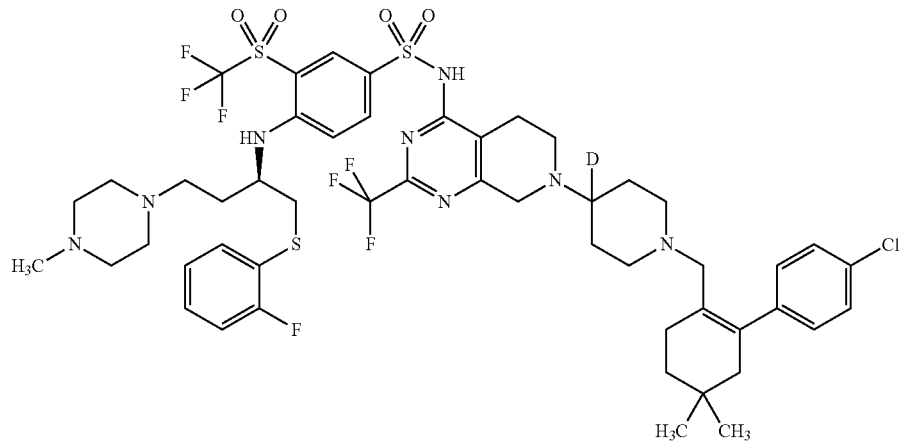 [SMILES: [2H]C1(N2CCc3c(nc(C(F)(F)F)nc3NS(=O)(=O)c3ccc(N[C@H](CCN4CCN(C)CC4)CSc4ccccc4F)c(S(=O)(=O)C(F)(F)F)c3)C2)CCN(CC2=C(c3ccc(Cl)cc3)CC(C)(C)CC2)CC1]

TOF MS ES+ (M+H$^+$): 1077.42; HPLC retention time=4.37 minutes.

Example 76

(R)-N-(7-(4((4'-chlorobiphenyl-2-yl)methyl)-4-methoxy-1-dueterocyclohexyl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide

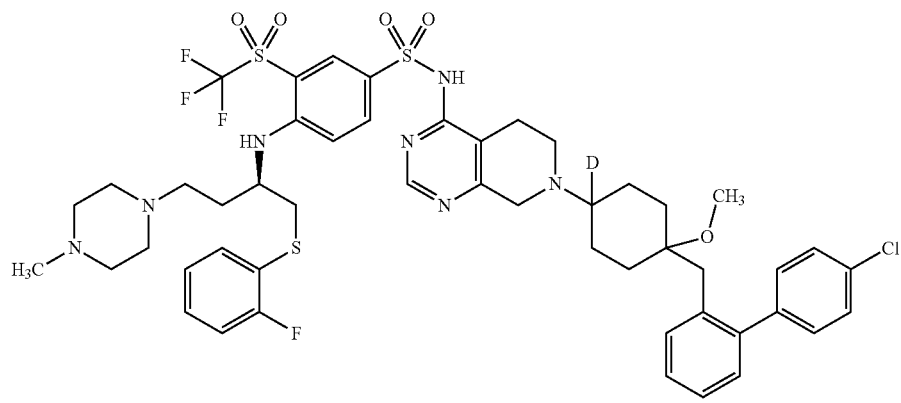 [SMILES: [2H]C1(N2CCc3c(ncnc3NS(=O)(=O)c3ccc(N[C@H](CCN4CCN(C)CC4)CSc4ccccc4F)c(S(=O)(=O)C(F)(F)F)c3)C2)CCC(Cc2ccccc2-c2ccc(Cl)cc2)(OC)CC1]

TOF MS ES+ (M+H$^+$): 1029.32; HPLC retention time=4.92 minutes.

Example 77

4-((R)-1-Benzyloxymethyl-3-dimethylamino-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide

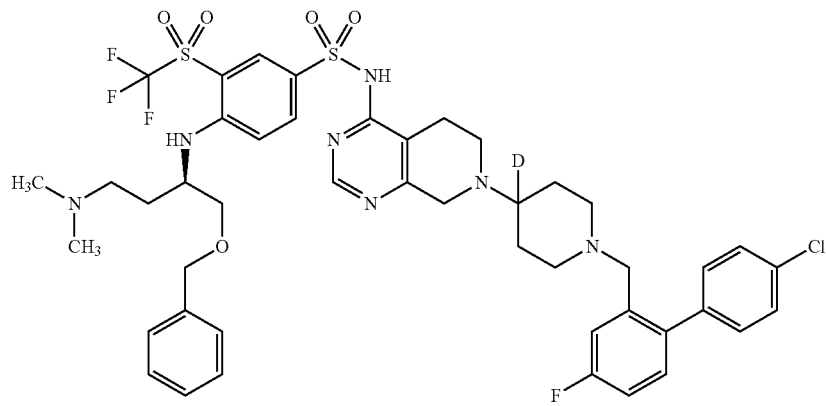 [SMILES: [2H]C1(N2CCc3c(ncnc3NS(=O)(=O)c3ccc(N[C@H](CCN(C)C)COCc4ccccc4)c(S(=O)(=O)C(F)(F)F)c3)C2)CCN(Cc2cc(F)ccc2-c2ccc(Cl)cc2)CC1]

TOF MS ES+ (M+H$^+$): 945.31 HPLC retention time=3.47 minutes.

Example 78

N-(7-(1-[2-(4-Chloro-phenyl)-4,4-dimethyl-cyclohex-1-enylmethyl]-4-deutero-piperidin-4-yl)-5,6,7,8-tetrahydro-pyrido[3,4-d]pyrimidin-4-yl)-4-[(R)-3-(isopropyl-methyl-amino)-1-phenylsulfanylmethyl-propylamino]-3-trifluoromethanesulfonyl-benzenesulfonamide

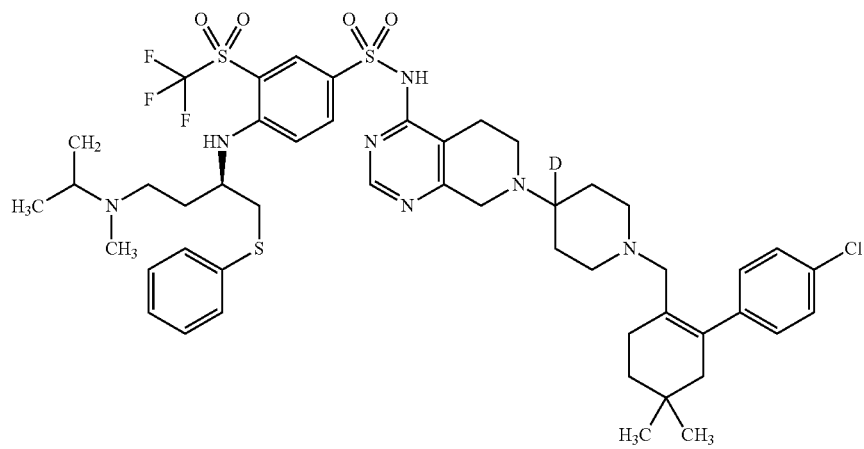 [SMILES: [2H]C1(N2CCc3c(ncnc3NS(=O)(=O)c3ccc(N[C@H](CCN(C)C(C)C)CSc4ccccc4)c(S(=O)(=O)C(F)(F)F)c3)C2)CCN(CC2=C(c3ccc(Cl)cc3)CC(C)(C)CC2)CC1]

TOF MS ES+ (M+H$^+$): 989.38; HPLC retention time=3.71 minutes.

Example 79

4-((R)-3-Amino-1-phenylsulfanylmethyl-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide

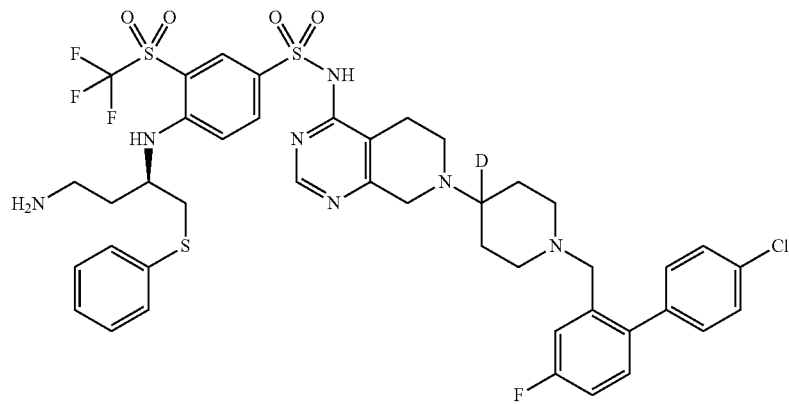 [SMILES: [2H]C1(N2CCc3c(ncnc3NS(=O)(=O)c3ccc(N[C@H](CCN)CSc4ccccc4)c(S(=O)(=O)C(F)(F)F)c3)C2)CCN(Cc2cc(F)ccc2-c2ccc(Cl)cc2)CC1]

TOF MS ES+ (M+H$^+$): 919.24; HPLC retention time=3.34 minutes.

Example 80

4-((2R)-4-(8-oxa-3-azabicyclo[3.2.1]octan-3-yl)-1-(phenylthio)butan-2-ylamino)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-3-(trifluoromethylsulfonyl)benzenesulfonamide

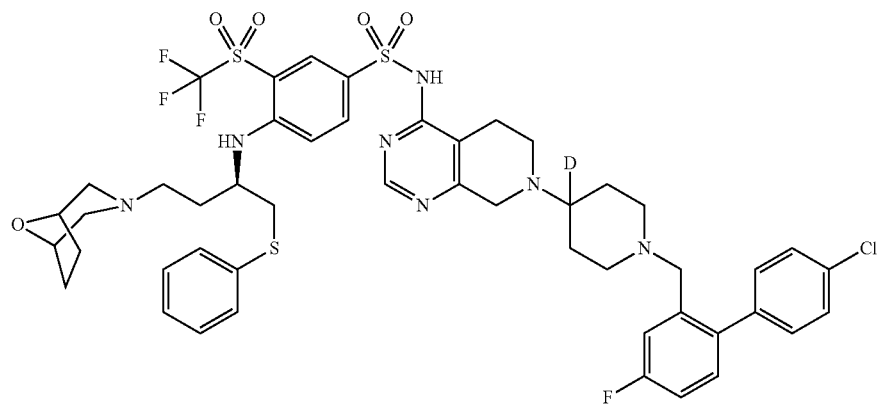 [SMILES: [2H]C1(N2CCc3c(ncnc3NS(=O)(=O)c3ccc(N[C@H](CCN4CC5CCC(C4)O5)CSc4ccccc4)c(S(=O)(=O)C(F)(F)F)c3)C2)CCN(Cc2cc(F)ccc2-c2ccc(Cl)cc2)CC1]

TOF MS ES+ (M+H$^+$): 1015.30; HPLC retention time=3.61 minutes.

Example 81

4-((2R)-4-(8-oxa-3-azabicyclo[3.2.1]octan-3-yl)-1-(phenylthio)butan-2-ylamino)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-3-(trifluoromethylsulfonyl)-benzenesulfonamide

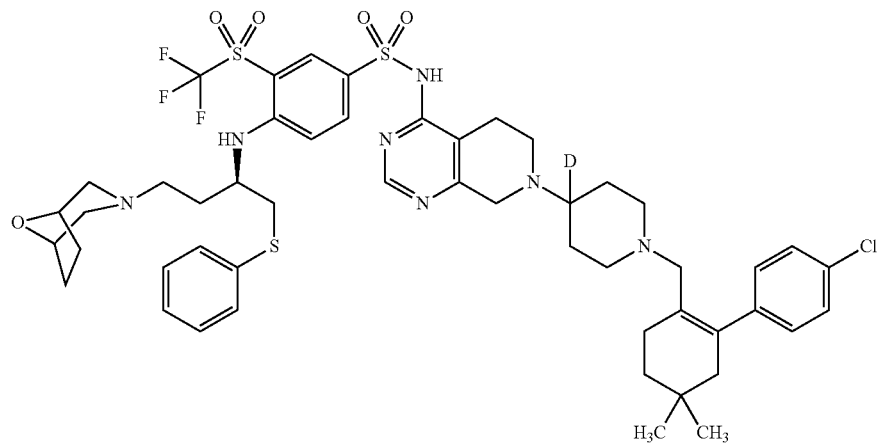 [SMILES: [2H]C1(N2CCc3c(ncnc3NS(=O)(=O)c3ccc(N[C@H](CCN4CC5CCC(C4)O5)CSc4ccccc4)c(S(=O)(=O)C(F)(F)F)c3)C2)CCN(CC2=C(c3ccc(Cl)cc3)CC(C)(C)CC2)CC1]

TOF MS ES+ (M+H$^+$): 1029.37 HPLC retention time=7.89 minutes.

Example 82

(R)-N-(7-(1-((4'-chloro-4 fluorobiphenyl-2-yl)methyl)-4-dueteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl) benzene sulfonamide

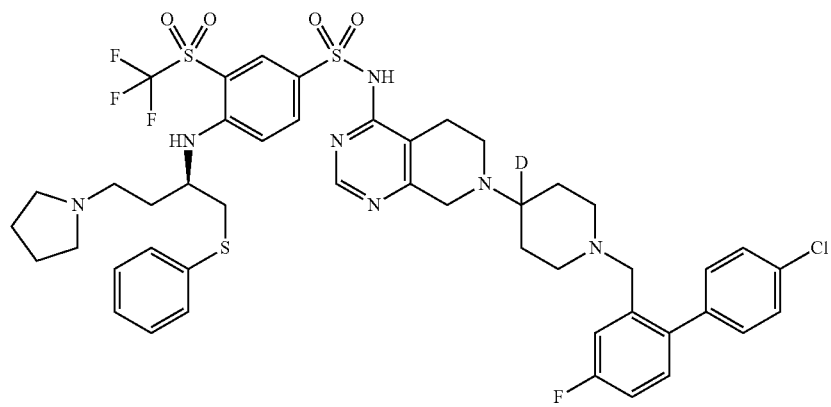 [SMILES: [2H]C1(N2CCc3c(ncnc3NS(=O)(=O)c3ccc(N[C@H](CCN4CCCC4)CSc4ccccc4)c(S(=O)(=O)C(F)(F)F)c3)C2)CCN(Cc2cc(F)ccc2-c2ccc(Cl)cc2)CC1]

TOF MS ES+ (M+H$^+$): 973.29; HPLC retention time=3.46 minutes.

Example 83

(R)—N—O-7-(1-((2-(4-chlorophenyl)-4,4-dimethyl-cyclohex-1-enyl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide

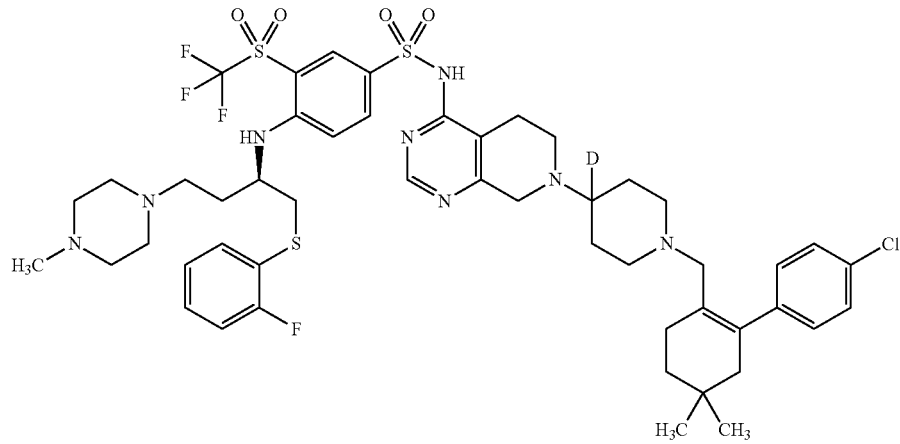 [SMILES: [2H]C1(N2CCc3c(ncnc3NS(=O)(=O)c3ccc(N[C@H](CCN4CCN(C)CC4)CSc4ccccc4F)c(S(=O)(=O)C(F)(F)F)c3)C2)CCN(CC2=C(c3ccc(Cl)cc3)CC(C)(C)CC2)CC1]

TOF MS ES+ (M+H$^+$): 1034.38; HPLC retention time=3.33 minutes.

Example 84

N-{7-[4-Deutero-1-(4'-chloro-4-fluoro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide

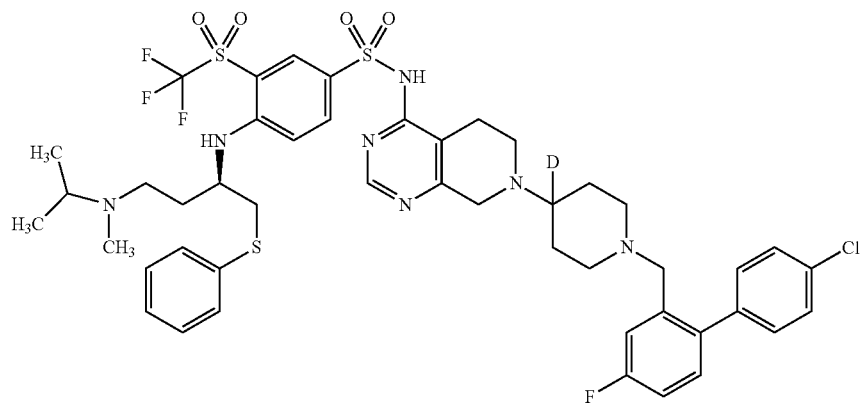 [SMILES: [2H]C1(N2CCc3c(ncnc3NS(=O)(=O)c3ccc(N[C@H](CCN(C)C(C)C)CSc4ccccc4)c(S(=O)(=O)C(F)(F)F)c3)C2)CCN(Cc2cc(F)ccc2-c2ccc(Cl)cc2)CC1]

TOF MS ES+ (M+H$^+$): 975.30; HPLC retention time=3.51 minutes.

Example 85

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide

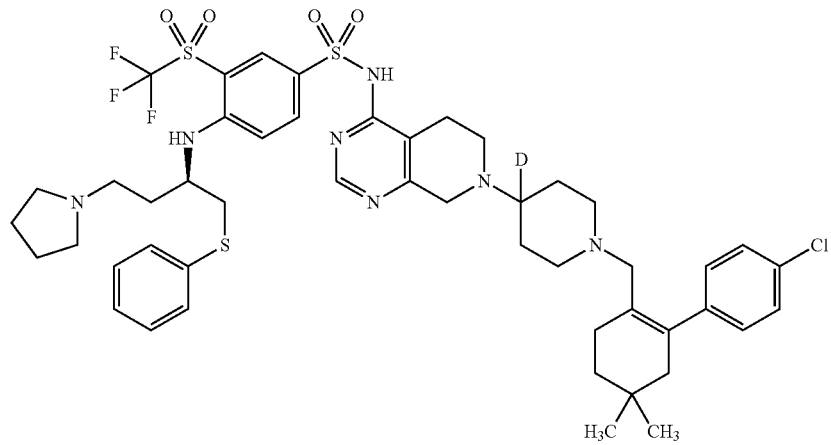 [SMILES: [2H]C1(N2CCc3c(ncnc3NS(=O)(=O)c3ccc(N[C@H](CCN4CCCC4)CSc4ccccc4)c(S(=O)(=O)C(F)(F)F)c3)C2)CCN(CC2=C(c3ccc(Cl)cc3)CC(C)(C)CC2)CC1]

TOF MS ES+ (M+H$^+$): 987.36; HPLC retention time=3.71 minutes.

Example 86

N-(7-{1-[(R)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide

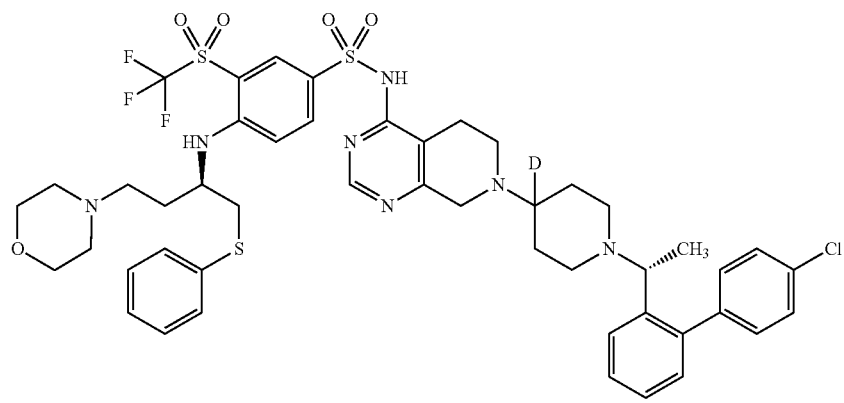 [SMILES: [2H]C1(N2CCc3c(ncnc3NS(=O)(=O)c3ccc(N[C@H](CCN4CCOCC4)CSc4ccccc4)c(S(=O)(=O)C(F)(F)F)c3)C2)CCN([C@H](C)c2ccccc2-c2ccc(Cl)cc2)CC1]

TOF MS ES+ (M+H$^+$): 985.31; HPLC retention time=3.45 minutes.

Example 87

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide

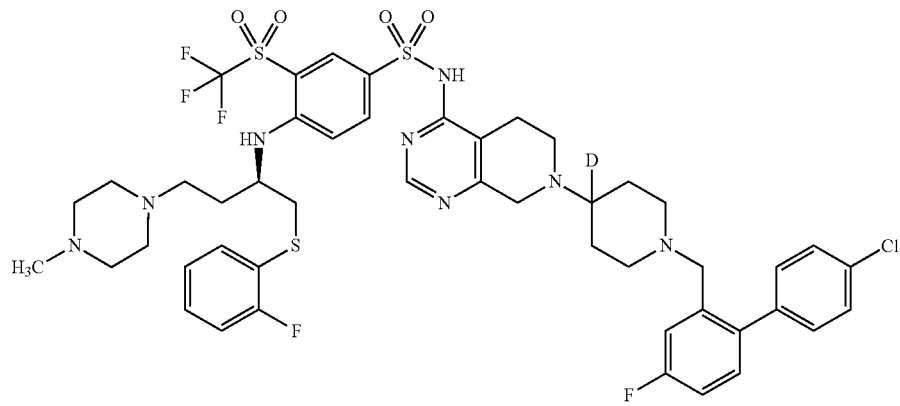 [SMILES: [2H]C1(N2CCc3c(ncnc3NS(=O)(=O)c3ccc(N[C@H](CCN4CCN(C)CC4)CSc4ccccc4F)c(S(=O)(=O)C(F)(F)F)c3)C2)CCN(Cc2cc(F)ccc2-c2ccc(Cl)cc2)CC1]

TOF MS ES+ (M+H$^+$): 1020.31; HPLC retention time=3.49 minutes.

Example 88

N-(7-{1-[(S)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide

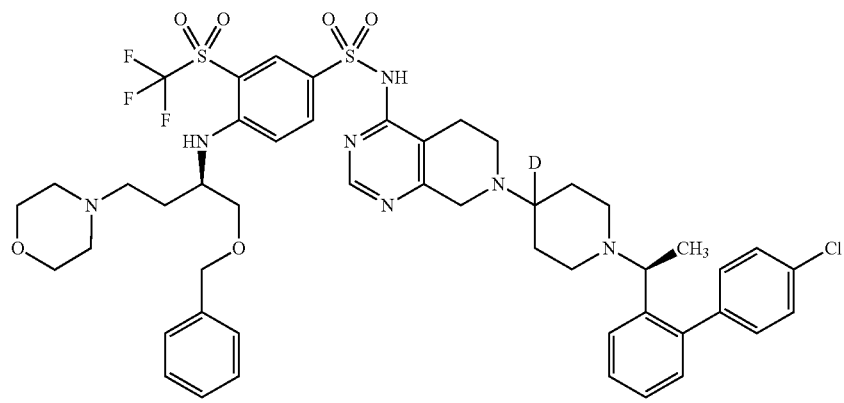 [SMILES: [2H]C1(N2CCc3c(ncnc3NS(=O)(=O)c3ccc(N[C@H](CCN4CCOCC4)COCc4ccccc4)c(S(=O)(=O)C(F)(F)F)c3)C2)CCN([C@@H](C)c2ccccc2-c2ccc(Cl)cc2)CC1]

TOF MS ES+ (M+H$^+$): 985.31; HPLC retention time=3.46 minutes.

Example 89

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(4-ethylpiperazin-1-yl)-1-(phenylthio)butan-2-ylamino)-3-(trifluoromethylsulfonyl)benzenesulfonamide

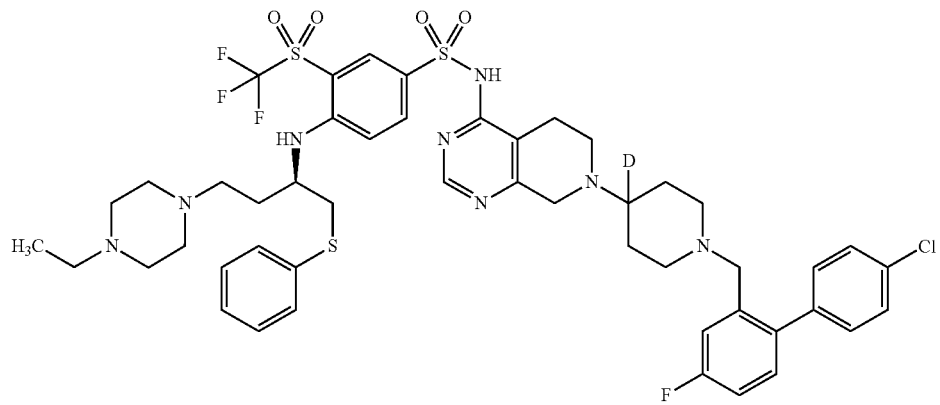 [SMILES: [2H]C1(N2CCc3c(ncnc3NS(=O)(=O)c3ccc(N[C@H](CCN4CCN(CC)CC4)CSc4ccccc4)c(S(=O)(=O)C(F)(F)F)c3)C2)CCN(Cc2cc(F)ccc2-c2ccc(Cl)cc2)CC1]

TOF MS ES+ (M+H$^+$): 1016.33 HPLC retention time=3.51 minutes.

Example 90

N-(7-(1-(1-(2-(4-chlorophenyl)-4,4-dimethylcyclohex-1-enyl)ethyl) 4-deuteropiperidin-4-yl)-5,6,7,8-tetrahydropyrido[3,4-d]pyrimidin-4-yl)-4-((R)-4-D-morpholino-1-(phenylthio)butan-2-ylamino)-3-(trifluoromethylsulfonyl)benzenesulfonamide

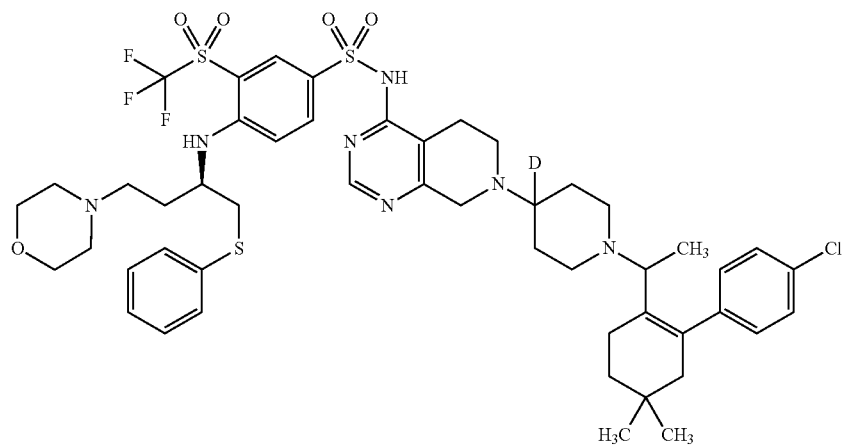 [SMILES: [2H]C1(N2CCc3c(ncnc3NS(=O)(=O)c3ccc(N[C@H](CCN4CCOCC4)CSc4ccccc4)c(S(=O)(=O)C(F)(F)F)c3)C2)CCN(C(C)C2=C(c3ccc(Cl)cc3)CC(C)(C)CC2)CC1]

TOF MS ES+ (M+H$^+$): 1017.37; HPLC retention time=3.76 minutes.

Example 91

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide

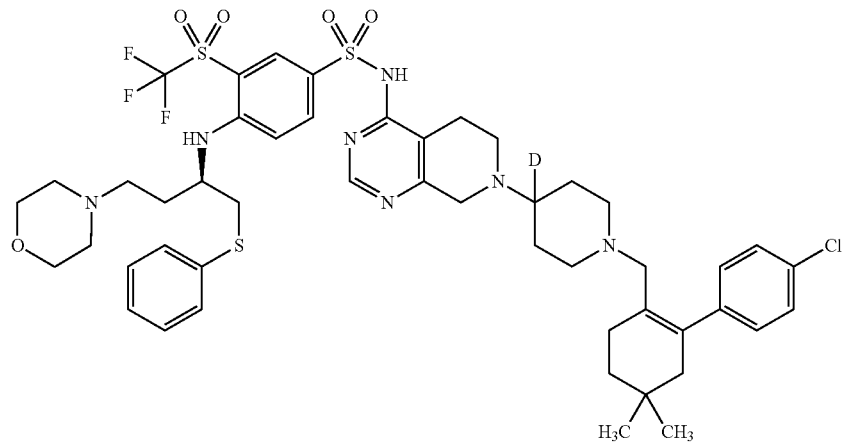 [SMILES: [2H]C1(N2CCc3c(ncnc3NS(=O)(=O)c3ccc(N[C@H](CCN4CCOCC4)CSc4ccccc4)c(S(=O)(=O)C(F)(F)F)c3)C2)CCN(CC2=C(c3ccc(Cl)cc3)CC(C)(C)CC2)CC1]

TOF MS ES+(M+14): 1003.35 HPLC retention time=3.73 minutes.

Synthesis of Examples 92-93 by reductive amination of ketones IX with amines V

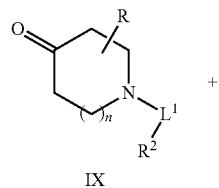

IX

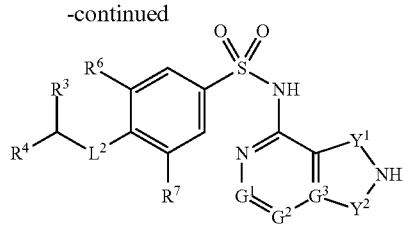

V

Example 92

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-morpholin-4-yl-1-phenylsulfanylmethyl-propylamino)-3-trifluoromethanesulfonyl-benzenesulfonamide

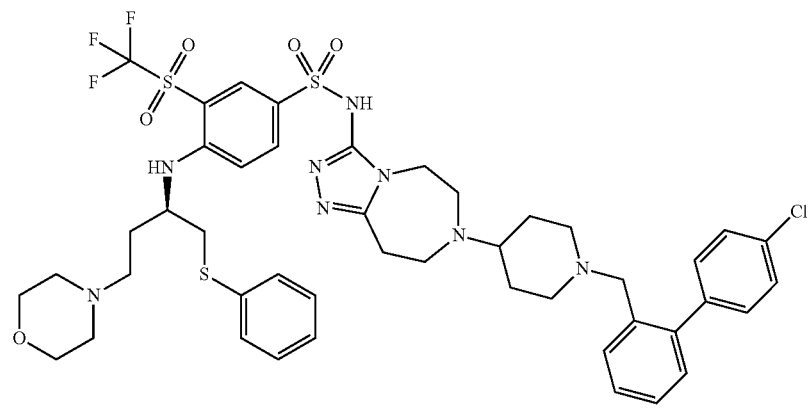 [SMILES: O=S(=O)(Nc1nnc2n1CCN(C1CCN(Cc3ccccc3-c3ccc(Cl)cc3)CC1)CC2)c1ccc(N[C@H](CCN2CCOCC2)CSc2ccccc2)c(S(=O)(=O)C(F)(F)F)c1]

To a vial containing 44(R)-3-morpholin-4-yl-1-phenylsulfanylmethyl-propylamino)-N-(5,6,7,8-tetrahydro-4H-1,2,3a,6-tetraaza-azulen-3-yl)-3-trifluoromethanesulfonyl benzenesulfonamide (50 mg, 0.072 mmol) and 1-(4'-chloro-biphenyl-2-ylmethyl)-piperidin-4-one (21.73 mg, 0.072 mmol) was added dichloromethane (1.5 mL) and methanol (1.5 mL) under nitrogen. The reaction mixture was stirred in an ice bath for 10 minutes, and then acetic acid (2.176 mg, 0.036 mmol) was added. After stirring in the ice bath for another 30 minutes, sodium cyanoborohydride (27.3 mg, 0.434 mmol) was added, and the reaction was heated to 45° C. and stirred for 14 hours. The reaction mixture was concentrated under reduced pressure, and then diluted with dichloromethane and water. Organics were extracted three times with dichloromethane. The combined organic layers were washed with brine, dried over $Na_2SO_4$, filtered and concentrated under reduced pressure. This crude material was purified via flash chromatography on silica gel (10-15% 2N $NH_3$ in methanol in $CH_2Cl_2$) to afford the title compound (5.5 mg, 8% yield).

$^1$H NMR (600 MHz, DMSO-$d_6$) δ ppm 8.03 (d, J=2.27 Hz, 1H), 7.88 (dd, J=9.06, 1.89 Hz, 1H), 7.40-7.50 (m, 5H), 7.14-7.39 (m, 9H), 6.99 (d, J=9.44 Hz, 1H), 6.85 (d, J=9.06 Hz, 1H), 4.06 (d, J=5.67 Hz, 1H), 4.00 (t, J=7.37 Hz, 1H), 3.80 (d, J=6.80 Hz, 1H), 3.47 (d, J=2.64 Hz, 4H), 3.24-3.31 (m, 4H), 2.77-2.83 (m, 2H), 2.64-2.76 (m, 5H), 2.41-2.47 (m, 1H), 2.19-2.36 (m, 5H), 2.15 (d, J=6.80 Hz, 2H), 1.93 (d, J=5.67 Hz, 1H), 1.81 (q, J=11.96 Hz, 2H), 1.71 (td, J=13.88, 5.85 Hz, 1H), 1.50-1.61 (m, 2H), 1.31-1.42 (m, 2H).

HR-MS (m/z, MH$^+$): 973.30

HPLC retention time: 3.50 minutes (Agilent 1100 HPLC system; Inertsil ODS3 100×3 mm C18 column; flow rate of 1.0 mL/minute; gradient of 5-95% acetonitrile/water with 0.1% FA)

Example 93

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-dimethylamino-1-phenyl-sulfanylmethyl-propylamino)-3-trifluoromethanesulfonyl-benzenesulfonamide To a vial containing 4-((R)-3-Dimethylamino-1-phenylsulfanylmethyl-propylamino)-N-(5,6,7,8-tetrahydro-4H-1,2,3a,6-tetraaza-azulen-3-yl)-3-trifluoromethanesulfonyl-benzenesulfonamide (1200 mg, 0.185 mmol) and 1-(4'-chloro-biphenyl-2-ylmethyl)-piperidin-4-one (55.5 mg, 0.185 mmol) was added methanol (6 mL) under nitrogen. The reaction mixture was stirred in an ice bath for 10 minutes, and then acetic acid (5.56 mg, 0.093 mmol) was added. After stirring in the ice bath for another 30 minutes, sodium cyanoborohydride (34.9 mg, 0.556 mmol) was added, and the reaction was stirred at ambient temperature for 14 hours. The reaction mixture was concentrated under reduced pressure and filtered. This crude material was purified via flash chromatography on silica gel (10-15% 2N $NH_3$ in methanol in $CH_2Cl_2$) to afford the title compound (24 mg, 20% yield).

$^1$H NMR (400 MHz, DMSO-$d_6$) δ ppm 8.03 (d, J=2.02 Hz, 1H), 7.88 (dd, J=9.09, 2.53 Hz, 1H), 7.31-7.51 (m, 10H), 7.24-7.31 (m, 3H), 7.15-7.23 (m, 2H), 6.91 (d, J=9.60 Hz, 1H), 4.01 (br, s, 1H), 3.80 (d, J=7.58 Hz, 2H), 3.15-3.27 (m, 2H), 2.79 (d, J=5.56 Hz, 2H), 2.65-2.75 (m, 6H), 2.31-2.48 (m, 3H), 2.12-2.22 (m, 1H), 2.08 (s, 6H), 1.65-1.96 (m, 5H), 1.49-1.60 (m, 2H), 1.29-1.43 (m, 2H).

HR-MS (m/z, MH+): meas. 931.28

HPLC retention time: 3.39 minutes (Agilent 1100 HPLC system; Inertsil ODS3 100×3 mm C18 column; flow rate of 1.0 mL/minute; gradient of 5-95% acetonitrile/water with 0.1% formic acid)

Examples 94-96 were prepared by reductive amination of ketones VI with amines V and removal of protecting group to afford Intermediates VII, followed by reductive amination with carbonyl compounds VIII.

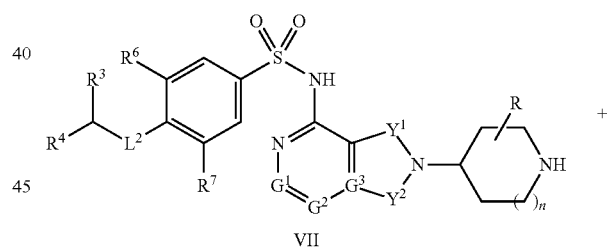

VII

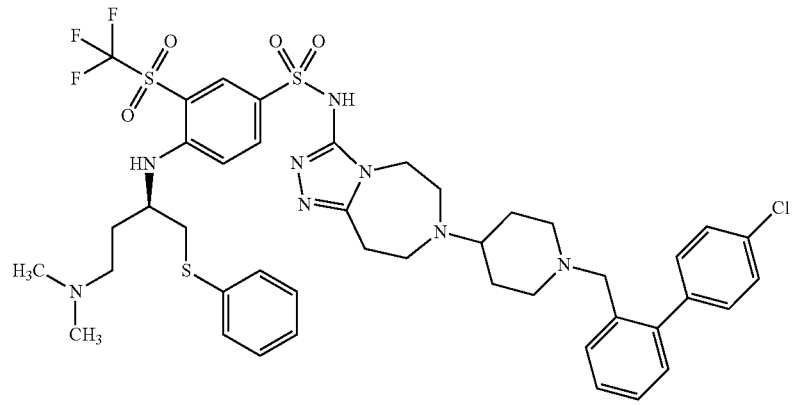 [SMILES: CN(C)CC[C@H](CSc1ccccc1)Nc1ccc(S(=O)(=O)Nc2nnc3n2CCN(C2CCN(Cc4ccccc4-c4ccc(Cl)cc4)CC2)CC3)cc1S(=O)(=O)C(F)(F)F]

-continued

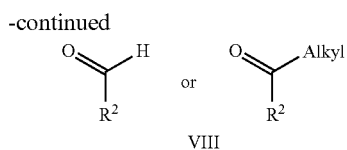

VIII

Example 94

N-{7-[1-(4'-Chloro-biphenyl-2-ylmethyl)-piperidin-4-yl]-5,6,7,8-tetrahydro-[1,2,4]triazolo[4,3-a]pyrazin-3-yl}-4-(R)-3-morpholin-4-yl-1-phenylsulfanylmethyl-propylamino)-3-trifluoromethanesulfonyl-benzenesulfonamide

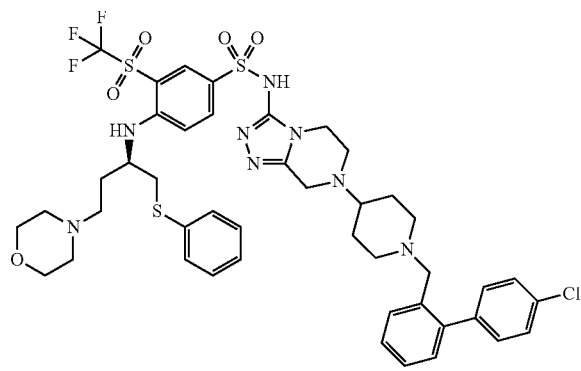 [SMILES: O=S(=O)(Nc1nnc2n1CCN(C1CCN(Cc3ccccc3-c3ccc(Cl)cc3)CC1)C2)c1ccc(N[C@H](CCN2CCOCC2)CSc2ccccc2)c(S(=O)(=O)C(F)(F)F)c1]

STEP A: To a vial containing 4-((R)-3-morpholin-4-yl-1-phenyl-sulfanylmethyl-propylamino)-N-(5,6,7,8-tetrahydro-[1,2,4]triazolo[4,3-a]pyrazin-3-yl)-3-trifluoromethanesulfonyl-benzenesulfonamide (50 mg, 0.074 mmol) and 4-oxo-piperidine-1-carboxylic acid tert-butyl ester (14.74 mg, 0.074 mmol) was added methanol (2 mL) under nitrogen. The reaction mixture was stirred in an ice bath for 10 minutes, and then acetic acid (0.424 µL, 7.40 µmol) was added. The reaction mixture was stirred for another 30 minutes. Sodium cyanoborohydride (41.85 mg, 0.666 mmol) was then added, and the reaction was stirred at ambient temperature for 72 hours. The reaction mixture was concentrated, filtered and purified via flash chromatography on silica gel (10-50% 7N NH$_3$ in methanol in CH$_2$Cl$_2$) to afford 4-{3-[4-((R)-3-Morpholin-4-yl-1-phenylsulfanylmethyl-propylamino)-3-trifluoromethanesulfonyl-benzenesulfonylamino]-5,6-dihydro-8H-[1,2,4]triazolo[4,3-a]pyrazin-7-yl}-piperidine-1-carboxylic acid tert-butyl ester (65 mg, 100% yield). MS [m/z; (M+1)$^+$]: 859.7

STEP B: To a solution of 4-{3-[4-((R)-3-morpholin-4-yl-1-phenylsulfanyl-methyl-propylamino)-3-trifluoromethane-sulfonyl-benzenesulfonylamino]-5,6-dihydro-8H-[1,2,4]triazolo[4,3-a]pyrazin-7-yl}-piperidine-1-carboxylic acid tert-butyl ester (65 mg, 0.076 mmol) in CH$_2$Cl$_2$ (2 mL) under nitrogen was added trifluoroacetic acid (0.146 mL, 1.892 mmol), and the reaction was stirred for 2 hours. The reaction mixture was then concentrated under reduced pressure. The residue was dissolved in methanol and converted to the free base by elution through a Si-Carbonate SPE filter to afford 4-((R)-3-Morpholin-4-yl-1-phenylsulfanylmethyl-propylamino)-N-(7-piperidin-4-yl-5,6,7,8-tetrahydro-[1,2,4]triazolo[4,3-a]pyrazin-3-yl)-3-trifluoromethanesulfonyl-benzenesulfonamide (37 mg, 65% yield). MS [m/z; (M+1)$^+$]: 759.7

STEP C: To a vial containing 4-((R)-3-morpholin-4-yl-1-phenylsulfanyl-methyl-propylamino)-N-(7-piperidin-4-yl-5,6,7,8-tetrahydro-[1,2,4]triazolo[4,3-a]pyrazin-3-yl)-3-trifluoromethanesulfonyl-benzenesulfonamide (37 mg, 0.049 mmol) and 4'-chloro-biphenyl-2-carbaldehyde (21.13 mg, 0.098 mmol) was added methanol (1.5 mL) under nitrogen. The reaction mixture was stirred in an ice bath for 10 minutes and then acetic acid (2.794, 0.049 mmol) was added. After stirring in the ice bath for an additional 30 minutes, sodium cyanoborohydride (18.38 mg, 0.293 mmol) was added. The reaction was then allowed to warm to ambient temperature and stir for 72 hours. The solvent was removed in vacuo, and the residue purified via flash chromatography on silica gel (10-50% methanol in CH$_2$Cl$_2$) to afford the title compound (18 mg, 39% yield).

$^1$H NMR (400 MHz, DMSO-d$_6$)) δ ppm 1.26-1.38 (m, 1H), 1.44 (q, J=9.87 Hz, 2H), 1.51-1.78 (m, 4H), 1.87-2.01 (m, 1H), 2.09-2.19 (m, 2H), 2.20-2.34 (m, 4H), 2.34-2.40 (m, 2H), 2.41-2.47 (m, 1H), 2.65-2.74 (m, 1H), 2.74-2.82 (m, 2H), 3.28 (d, J=7.03 Hz, 1H), 3.45-3.53 (m, 8H), 3.58 (s, 2H), 4.05 (d, J=5.52 Hz, 1H), 6.84 (d, J=9.03 Hz, 1H), 6.95 (d, J=9.54 Hz, 1H), 7.15-7.22 (m, 2H), 7.27 (t, J=7.78 Hz, 2H), 7.30-7.38 (m, 4H), 7.39-7.51 (m, 6H), 7.90 (dd, J=9.03, 1.51 Hz, 1H), 8.06 (s, 1H).

HR-MS (m/z, MH$^+$): meas. 959.28

HPLC retention time: 3.60 minutes (Agilent 1100 HPLC system; Inertsil ODS3 100×3 mm C18 column; flow rate of 1.0 mL/minute; gradient of 5-95% acetonitrile/water with 0.1% FA)

Example 95

N-{7-[1-(4'-Chloro-biphenyl-2-ylmethyl)-azepan-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide

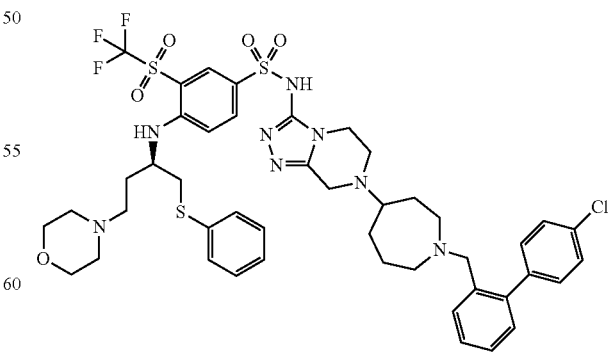

STEP A: To a vial containing 44(R)-3-morpholin-4-yl-1-phenyl-sulfanylmethyl-propylamino)-N-(5,6,7,8-tetrahydro-[1,2,4]triazolo[4,3-a]pyrazin-3-yl)-3-trifluoromethanesulfonyl-benzenesulfonamide (80 mg, 0.118 mmol) and 4-oxo-azepane-1-carboxylic acid tert-butyl ester (63.1 mg, 0.296 mmol) was added methanol (4 mL) under nitrogen. The reaction mixture was stirred in an ice bath for 10 minutes and then acetic acid (8.13 µL, 0.142 mmol) was added. After stirring in the ice bath for an additional 15 minutes, sodium cyanoborohydride (59.5 mg, 0.947 mmol) was added. The reaction was then allowed to warm to ambient temperature and stir for 72 hours. The reaction mixture was then concentrated, filtered and purified via flash chromatography on silica gel (10-50% 7N $NH_3$ in methanol in $CH_2Cl_2$) to afford 4-{3-[4-((R)-3-Morpholin-4-yl-1-phenylsulfanylmethyl-propylamino)-3-trifluoromethanesulfonyl-benzenesulfonylamino]-5,6-dihydro-8H-[1,2,4]triazolo[4,3-a]pyrazin-7-yl}-azepane-1-carboxylic acid tert-butyl ester (76 mg, 74% yield). MS [m/z; (M+1)$^+$]: 873.8

STEP B: To a solution of 4-{3-[4-((R)-3-morpholin-4-yl-1-phenylsulfanyl-methyl-propylamino)-3-trifluoromethane-sulfonyl-benzenesulfonylamino]-5,6-dihydro-8H-[1,2,4]triazolo[4,3-a]pyrazin-7-yl}-azepane-1-carboxylic acid tert-butyl ester (76 mg, 0.087 mmol) in $CH_2Cl_2$ (2 mL) under nitrogen was added trifluoroacetic acid (0.168 mL, 2.176 mmol), and the reaction was stirred for 2.5 hours. The reaction mixture was concentrated, water and $CH_2Cl_2$ were added, and the solution was basified to pH approximately 8 with saturated $Na_2CO_3$. The aqueous layer was extracted three times with $CH_2Cl_2$. The combined organic layers were washed with brine, dried over $Na_2SO_4$, filtered and concentrated under reduced pressure to afford N-(7-Azepan-4-yl-5,6,7,8-tetrahydro-[1,2,4]triazolo[4,3-a]pyrazin-3-yl)-4-((R)-3-morpholin-4-yl-1-phenylsulfanylmethyl-propylamino)-3-trifluoromethanesulfonyl-benzenesulfonamide (62 mg, 92% yield). MS [m/z; (M+1)$^+$]: 773.6

STEP C: To a vial containing N-(7-azepan-4-yl-5,6,7,8-tetrahydro-[1,2,4]triazolo[4,3-a]pyrazin-3-yl)-4-((R)-3-morpholin-4-yl-1-phenylsulfanylmethyl-propylamino)-3-trifluoromethanesulfonyl-benzenesulfonamide (62 mg, 0.080 mmol) and 4'-chloro-biphenyl-2-carbaldehyde (52.1 mg, 0.241 mmol) was added methanol (2.5 mL) under nitrogen. The reaction was stirred in an ice bath for 10 minutes and then acetic acid (5.51 µL, 0.096 mmol) was added. After stirring in the ice bath for an additional 15 minutes, sodium cyanoborohydride (40.3 mg, 0.642 mmol) was added. The reaction was then allowed to warm to ambient temperature and stir for 72 hours. The reaction mixture was concentrated, filtered and purified via flash chromatography on silica gel (10-50% methanol in $CH_2Cl_2$) to afford the title compound (50 mg, 64% yield).

$^1$H NMR (400 MHz, DMSO-d$_6$) δ ppm 8.06 (d, J=2.01 Hz, 1H), 7.90 (d, J=7.53 Hz, 1H), 7.39-7.52 (m, 6H), 7.31-7.38 (m, 4H), 7.27 (t, J=7.78 Hz, 2H), 7.18-7.22 (m, 2H), 6.95 (d, J=9.54 Hz, 1H), 6.84 (d, J=9.03 Hz, 1H), 4.05 (d, J=5.52 Hz, 1H), 3.58 (s, 2H), 3.44-3.52 (m, 8H), 3.22-3.33 (m, 2H), 2.64-2.86 (m, 4H), 2.45 (d, J=5.02 Hz, 1H), 2.23-2.40 (m, 7H), 2.11-2.20 (m, 2H), 1.88-1.98 (m, 1H), 1.57-1.77 (m, 4H), 1.44 (q, J=9.87 Hz, 21-1).

HR-MS (m/z, MH+): measured 973.29

HPLC retention time: 3.57 minutes (Agilent 1100 HPLC system; Inertsil ODS3 100×3 mm C18 column; flow rate of 1.0 mL/minute; gradient of 5-95% acetonitrile/water with 0.1% formic acid)

Example 96

N-{7-[1-(4'-Chloro-biphenyl-2-ylmethyl)-2-methyl-piperidin-4-yl]-5,6,7,8-tetrahydro-[1,2,4]triazolo[4,3-a]pyrazin-3-yl}-4-((R)-3-morpholin-4-yl-1-phenyl-sulfanylmethyl-propylamino)-3-trifluoromethanesulfonyl-benzenesulfonamide

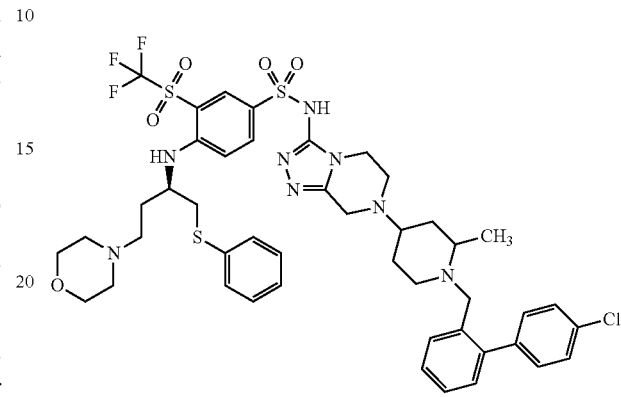

STEP A: To a vial containing 4-((R)-3-morpholin-4-yl-1-phenylsulfanyl-methyl-propylamino)-N-(5,6,7,8-tetrahydro-[1,2,4]triazolo[4,3-a]pyrazin-3-yl)-3-trifluoromethane-sulfonyl-benzenesulfonamide (60 mg, 0.089 mmol) and 2-methyl-4-oxo-piperidine-1-carboxylic acid tert-butyl ester (47.3 mg, 0.222 mmol) was added methanol (3 mL) under nitrogen. The reaction mixture was stirred in an ice bath for 10 minutes and then acetic acid (6.104, 0.107 mmol) was added. After stirring in the ice bath for an additional 15 minutes, sodium cyanoborohydride (44.6 mg, 0.710 mmol) was then added, and the reaction was stirred at ambient temperature for 15 hours. The reaction mixture was concentrated, filtered, and purified via flash chromatography on silica gel (10-50% 7N $NH_3$ in methanol in $CH_2Cl_2$) to afford 2-methyl-4-{3-[4-((R)-3-morpholin-4-yl-1-phenylsulfanylmethyl-propylamino)-3-trifluoromethanesulfonyl-benzenesulfonylamino]-5,6-dihydro-8H-[1,2,4]triazolo[4,3-a]pyrazin-7-yl}-piperidine-1-carboxylic acid tert-butyl ester (42 mg, 53% yield). MS [m/z; (M+1)$^+$]: 873.8

STEP B: To a solution of 2-methyl-4-{3-[4-((R)-3-morpholin-4-yl-1-phenylsulfonylmethylpropyl-amino)-3-trifluoromethanesulfonyl-benzenesulfonylamino]-5,6-dihydro-8H-[1,2,4]triazolo[4,3-a]pyrazin-7-yl}-piperidine-1-carboxylic acid tert-butyl ester (42 mg, 0.048 mmol) in $CH_2Cl_2$ (1 mL) under nitrogen was added trifluoroacetic acid (0.093 mL, 1.203 mmol) and the reaction was stirred for 2.5 hours. The reaction mixture was then concentrated and diluted with water and $CH_2Cl_2$. It was then basified to pH approximately 8 with saturated $Na_2CO_3$. The aqueous layer was extracted three times with $CH_2Cl_2$. The combined organic layers were washed with brine, dried over $Na_2SO_4$, filtered, and concentrated under reduced pressure to afford N-[7-(2-methyl-piperidin-4-yl)-5,6,7,8-tetrahydro-[1,2,4]triazolo[4,3-a]pyrazin-3-yl]-4-((R)-3-morpholin-4-yl-1- phenylsulfanylmethyl-propylamino)-3-trifluoromethane-sulfonyl-benzenesulfonamide (22 mg, 59% yield). MS [m/z; (M+1)+]: 773.6

STEP C: To a vial containing N-[7-(2-methyl-piperidin-4-yl)-5,6,7,8-tetrahydro-[1,2,4]triazolo[4,3-a]pyrazin-3-yl]-4-((R)-3-morpholin-4-yl-1-phenylsulfanylmethyl-propylamino)-3-trifluoro methanesulfonyl-benzenesulfonamide (20 mg, 0.026 mmol), 4'-chloro-biphenyl-2-carbaldehyde (16.82 mg, 0.078 mmol) and zinc chloride (3.53 mg, 0.034 mol) was added methanol (1 mL) under nitrogen and the mixture was stirred for 10 minutes. Sodium cyanoborohydride (13.01 mg, 0.207 mmol) was then added, and the reaction was stirred at ambient temperature for 14 hours. The reaction mixture was then concentrated and partitioned between ethyl acetate and 2 M NaOH. The aqueous layer was extracted three times with EtOAc. The combined organic layers were washed with 1M NaOH, dried under $Na_2SO_4$, filtered and concentrated under reduced pressure. The crude material was purified via HPLC (0.1% TFA Modifier in water in MeCN) to afford the title compound as a TFA salt (5 mg, 18% yield).

$^1$H NMR (400 MHz, DMSO-$d_6$) δ ppm 13.15 (d, J=10.54 Hz, 1H), 8.08-8.18 (m, 1H), 7.90-8.01 (m, 1H), 7.66-7.84 (m, 1H), 7.51-7.61 (m, 4H), 7.34-7.44 (m, 3H), 7.28-7.34 (m, 2H), 7.22-7.27 (m, 2H), 7.14-7.21 (m, 1H), 7.02-7.11 (m, 1H), 6.84 (t, J=8.03 Hz, 1H), 4.06-4.21 (m, 3H), 3.89-4.03 (m, 4H), 3.62-3.71 (m, 3H), 3.54-3.64 (m, 4H), 3.48-3.56 (m, 2H), 3.15-3.28 (m, 1H), 2.95-3.14 (m, 4H), 2.81-2.92 (m, 2H), 2.63-2.76 (m, 3H), 2.03-2.22 (m, 2H), 1.75 (d, J=12.55 Hz, 1H), 1.57 (br. s., 1H), 1.31 (d, J=8.01 Hz, 1H), 1.21-1.27 (m, 2H), 0.94 (d, J=7.03 Hz, 1H).

HR-MS (m/z, MH+): 973.29

HPLC retention time: 3.59 minutes (Agilent 1100 HPLC system; Inertsil ODS3 100×3 mm C18 column; flow rate of 1.0 mL/minute; gradient of 5-95% acetonitrile/water with 0.1% formic acid)

Suzuki Coupling with 3-chloro-Phenylboronic Acid.

Example 97

N-{7-[1-(3'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide

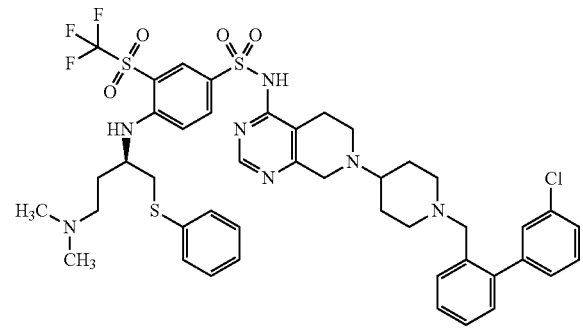 [SMILES: CN(C)CC[C@H](CSc1ccccc1)Nc1ccc(S(=O)(=O)Nc2ncnc3c2CCN(C2CCN(Cc4ccccc4-c4cccc(Cl)c4)CC2)C3)cc1S(=O)(=O)C(F)(F)F]

A microwave vial equipped with a stir bar was charged with sodium carbonate (11.8 mg, 0.11 mmol). The vial was then placed in an oven and dried for 30 minutes. It was then removed from the oven and allowed to cool to room temperature under nitrogen. Example 7 (50 mg, 0.056 mmol), 3-chloro-phenylboronic acid (13.1 mg, 0.084 mmol) and Pd(PPh$_3$)$_4$(3.2 mg, 0.0028 mmol) were added, followed by DME: EtOH: water (2 mL, 2:1:1 ratio). The resulting mixture was degassed by bubbling nitrogen through the solution, and then heated conventionally to 80° C. for 16 hours. The reaction was then cooled to room temperature and filtered. The filtrate was concentrated and the crude residue was purified by flash chromatography on silica gel (0-100% methanol in CH$_2$Cl$_2$) to afford the title compound (26 mg, 50% yield).

$^1$H NMR (400 MHz, MeOD) δ ppm: 8.35 (s, 1H), 8.12 (s, 1H), 7.95 (dd, J=2.01, 9.03 Hz, 1H), 7.52 (s, 1H), 7.46-7.50 (m, 1H), 7.12-7.43 (m, 1H), 6.71 (d, J=9.54 Hz, 1H), 3.93 (m, 1H), 3.60 (s, 2H), 3.49 (s, 2H), 3.10-3.27 (m, 2H), 2.62-2.96 (m, 8H), 2.49-2.58 (m, 7H), 2.12 (m, 1H), 1.97-2.07 (m, 2H), 1.84-1.95 (m, 3H), 1.51-1.63 (m, 2H).

HR-MS (m/z, MH+): measured 928.55

HPLC retention time=3.38 minutes (Agilent 1100 HPLC system; Inertsil ODS3 100×3 mm C18 column; flow rate of 1.0 mL/minute; gradient: 5-95% acetonitrile/water with 0.1% FA over 7.75 minutes).

The following compounds were prepared by Suzuki coupling of Example 7 with the requisite boronic acid following the procedure for Example 97 above.

Example 98

N-(7-yl)-((2'-chlorobiphenyl-2-yl)methyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide

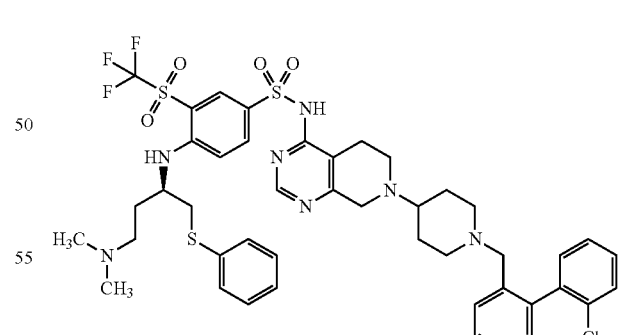

TOF MS ES+ (M+H$^+$): 928.27; HPLC retention time=3.32 minutes.

Example 99

(R)-4-(4-(dimethylamino)-1-(phenylthio)butan-2-ylamino)-N-(7-(1-((4'-(trifluoromethyl)biphenyl-2-yl)-methyl)piperidin-4-yl)-5,6,7,8-tetrahydropyrido[3,4-d]pyrimidin-4-yl)-3-(trifluoromethylsulfonyl)benzenesulfonamide

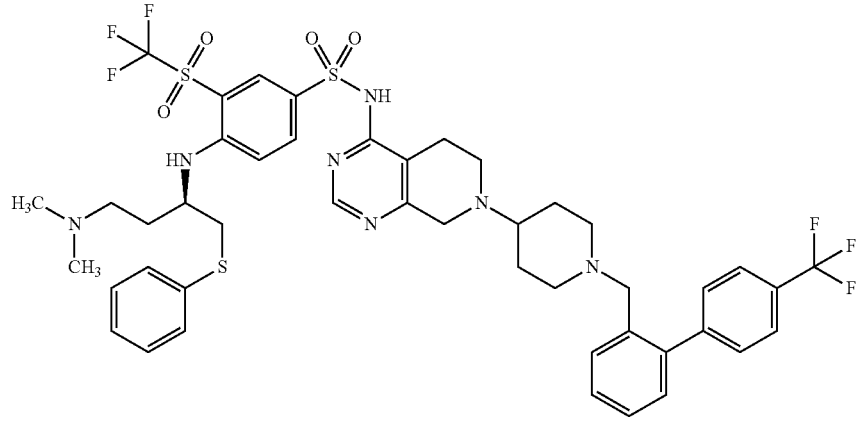 [SMILES: CN(C)CC[C@H](CSc1ccccc1)Nc1ccc(S(=O)(=O)Nc2ncnc3c2CCN(C2CCN(Cc4ccccc4-c4ccc(C(F)(F)F)cc4)CC2)C3)cc1S(=O)(=O)C(F)(F)F]

TOF MS ES+ (M+H$^+$): 962.30; HPLC Retention time=3.69 minutes.

PHARMACOLOGICAL DATA

Biology Assay Section
Method for determining IC50s

The present method includes utility of a Surface plasmon resonance (SPR)-based biosensor (Biacore™ GE Healthcare, Uppsala, Sweden) to characterize BCL-2 inhibitors.

Biacore™ utilizes the phenomenon of surface plasmon resonance (SPR) to detect and measure binding interactions. In a typical Biacore experiment, one of the interacting molecules (ligand) is immobilized on a flexible dextran matrix while the interacting partner (analyte) is allowed to flow across that surface. A binding interaction results in an increase in mass on the sensor surface and a corresponding direct change in the refractive index of the medium in the vicinity of the sensor surface. Changes in refractive index or signal are recorded in resonance units (R.U.) Signal changes due to association and dissociation of complexes are monitored in a non-invasive manner, continuously and in real-time, the results of which are reported in the form of a sensorgram. The SPR assay is configured to examine solution inhibition of BCL-2 binding to peptide derivatized sensor surfaces to generate 1050 values as a measure of inhibitor potency.

Solution Inhibition Assay Format:

Biacore™ A100 (GE Healthcare, Uppsala, Sweden) was used to conduct all experiments reported herein. Sensor surface preparation and all interaction analyses experiments were performed at 25° C. Reagents were purchased from GE Healthcare. Running buffer containing 10 mM Hepes, pH7.4, 150 mM sodium chloride, 1.25 mM Dithiothreitol, 3% Dimethyl sulfoxide and 0.05% polysorbate 20 were utilized throughout all analyses.

Biotinylated BAK, BAD and NOXA peptides were diluted to 10 nM in running buffer and captured onto a sensor surface pre-derivatized with streptavidin (sensor chip SA) to peptide surface densities in the range 50-100 R.U. Peptide captured surfaces were blocked with 500 μM PEO$_2$-Biotin. A blank detection spot in each flowcell was similarly blocked with PEO$_2$-biotin and served as a reference spot in the competition assay.

Interaction analyses were performed by first equilibrating each sample within a 6 point three fold compound dilution series in the range 16 μM to 0.004 nM with 56 nM BCL2 for one hour during instrument start-up procedures. Protein compound mixtures were then injected over each peptide surface in parallel for 60 seconds at a flow-rate of 30 μL/min. 56 nM BCL2 control samples were also prepared and run at regular intervals during the assay. Surface regeneration was performed at the end of each analysis cycle by two 30 second injections of 10 mM Glycine, pH 2.5, 1M Sodium Chloride, 0.05% polysorbate 20. Samples and control compound samples were run in duplicate and controls are also run at regular intervals during the assay to monitor surface and assay performance.

Data analyses are carried out using Biacore™ A100 evaluation software v1.1 to validate assay quality. Binding level report points were used relative to BCL2 control samples to calculate % inhibition values for each compound protein mixture. These data are then plotted versus compound concentration and analyzed in Tibco® Spotfire® v2.1 via logistic regression to calculate IC$_{50}$ values for each compound. Table 4 shows the IC$_{50}$ value of selected compounds.

TABLE 4

| Example | Name | Bcl-2 Biacore IC$_{50}$ (nM) |
|---|---|---|
| 1 | N-{7-[1-(4'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-nitro-benzenesulfonamide | 100 |
| 2 | (R)-N-(7-(1-((2-(4-chlorophenyl)-5,5-dimethyl-cyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-nitrobenzenesulfonamide | 31 |
| 3 | N-(7-((2S)-1((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-nitrobenzenesulfonamide | 62 |
| 4 | N-(7-((2S)-1-((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide, trifluoroacetate salt | 22 |

TABLE 4-continued

| Example | Name | Bcl-2 Biacore IC$_{50}$ (nM) |
|---|---|---|
| 5 | (R)-4-(4-(dimethylamino)-1-(phenylthio)butan-2-ylamino)-N-(7-(1-((4'-fluorobiphenyl-2-yl)methyl)piperidin-4-yl)-5,6,7,8-tetrahydropyrido[3,4-d]pyrimidin-4-yl)-3-(trifluoromethylsulfonyl)benzenesulfonamide | 25 |
| 6 | (R)-N-(7-(1((4'-bromobiphenyl-2-yl)methyppiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 19 |
| 7 | (R)-N-(7-(1-(2-bromobenzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 506 |
| 8 | N-{7-[2-(4-Chloro-phenyl)-5,5-dimethyl-cyclohex-1-enylmethyl]-5,6,7,8-tetrahydro-pyrido[3,4-d]pyrimidin-4-yl}-4-((R)-3-morpholin-4-yl-1-phenylsulfanylmethyl-propylamino)-3-trifluoromethanesulfonylbenzenesulfonamide | 76 |
| 9 | (R)-N-(7-(1-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide | 144 |
| 10 | (R)-N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 31 |
| 11 | (R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide. | 20 |
| 12 | (R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3,5-difluorobenzenesulfonamide | 3065 |
| 13 | N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide | 502 |
| 14 | N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide | 696 |
| 15 | N-(4-(N-(7-(1-((4'-chloro-4-fluorobiphenyl-2-yl)methyl)piperidin-4-yl)-5,6,7,8-tetrahydropyrido[3,4-d]pyrimidin-4-yl)sulfamoyl)-2-(trifluoromethylsulfonyl)phenyl)-N-(2-(phenylthio)ethyl)acetamide | 757 |
| 16 | (R)-N-(7-(1-((2-(4-chlorophenyl)-4,4-dimethylcyclohex-1-enyl)methyl)piperidin-4-yl)-5,6,7,8-tetrahydropyridop[3,4-d]pyrimidin-4-yl)-4-(4-morpholino-1-(phenylthio)butan-2-ylamino)-3-(trifluoromethylsulfonyl)benzenesulfonamide | 41 |
| 17 | (R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 22 |
| 18 | N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide | 579 |
| 19 | (R)-N-(7-(1-((4'-chloro-5-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(tritluoromethylsulfonyl)benzenesulfonamide | 35 |
| 20 | (R)-N-(7-(1-((4'-chloro-4-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 22 |
| 21 | (R)-N-(7-(1-((4'-chloro-3-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 30 |
| 22 | (R)-3-(4-(N-(7-(1-((4'-chlorobiphenyl-2-yl)methyl)piperidin-4-yl)-5,6,7,8-tetrahydropyrido[3,4-d]pyrimidin-4-yl)sulfamoyl)-2-nitrophenylamino)-N,N-dimethyl-4-(phenylthio)butanamide | 75 |
| 23 | N-{7-[1-(4'-Chloro-biphenyl-2-ylmethyl)-piperidin-4-yl]-5,6,7,8-tetrahydro-pyrido[3,4-d]pyrimidin-4-yl}-4[(R)-3-(4-ethyl-piperazin-1-yl)-1-phenylsulfanylmethyl-propylamino)-3-trifluoromethanesulfonyl-benzenesulfonamide | 51 |
| 24 | N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide | 89 |
| 25 | 4-((R)-1-Benzyloxymethyl-3-dimethylamino-propylamino)-N-{7-[1-(4'-chloro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide | 142 |
| 26 | N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonyl-benzenesulfonamide | 48 |
| 27 | N-(7-(1-((2-(4-chlorophenyl)-4,4-dimethylcyclohex-1-enyl)methyl)-2-methylpiperidin-4-yl)-5,6,7,8-tetrahydropyrido[3,4-d]pyrimidin-4-yl)-4-((R)-4-morpholino-1-(phenylthio) butan-2-ylamino)-3-(trifluoromethylsulfonyl)benzenesulfonamide | 206 |
| 28 | (R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide | 44 |
| 29 | N-(7-(1-(1-(4'-chlorobiphenyl-2-yl)ethyl)piperidin-4-yl)-5,6,7,8-tetrahydropyrido[3,4-d]pyrimidin-4-yl)-4-((R)-1-(2-chlorophenylthio)-4-(dimethylamino)butan-2-ylamino)-3-(trifluoromethylsulfonyl)benzenesulfonamide | 73 |
| 30 | (R)-N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)-4-(piperidin-1-yl)butan-2-ylamino)-3-(trifluoromethylsulfonyl)benzenesulfonamide | 128 |
| 31 | N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide | 84 |
| 32 | (R)-N-(7-(1-((2-(4-chlorophenyl)-4,4-dimethylcyclohex-1-enyl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide | 87 |
| 33 | (R)-N-(7-(1((4'-chlorobiphenyl-2-yl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide | 73 |
| 34 | N-(7-(1-(1-(4'-chlorobiphenyl-2-yl)ethyl)piperidin-4-yl)-2-(trifluoromethyl)-5,6,7,8-tetrahydropyrido[3,4-d]pyrimidin-4-yl)-4-((R)-1-(2-chlorophenylthio)-4-(dimethylamino) butan-2-ylamino)-3-(trifluoromethylsulfonyl)benzenesulfonamide | 99 |

TABLE 4-continued

| Example | Name | Bcl-2 Biacore IC$_{50}$ (nM) |
|---|---|---|
| 35 | N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-(4-methylpiperazin-1-yl)-1-(phenylthio)butan-2-ylamino)-3-(trifluoromethylsulfonyl)benzenesulfonamide | 80 |
| 36 | (R)-N-(7-(1-((4'-chloro-4-methoxybiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 34 |
| 37 | N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(4-fluoro-phenylsulfanylmethyl)-propylamino[-3-trifluoromethanesulfonyl-benzenesulfonamide | 58 |
| 38 | (R)-N-(7-(1-((4'-chlorobiphenyl-2-yl)methyl)piperidin-4-yl)-5,6,7,8-tetrahydropyrido[3,4-d]pyrimidin-4-yl)-4-(1-(2,6-dichlorophenylthio)-4-(dimethylamino)butan-2-ylamino)-3-(trifluoromethylsulfonyl)benzenesulfonamide | 41 |
| 39 | N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3,4-dichloro-phenylsulfanylmethyl)-3-dimethylamino-propylamino]-3-trifluoromethanesulfonyl-benzene-sulfonamide | 41 |
| 40 | (R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide | 32 |
| 41 | (R)-N-(7-(1-((4'-chlorobiphenyl-2-yl)methyl)piperidin-4-yl)-5,6,7,8-tetrahydropyrido[3,4-d]pyrimidin-4-yl)-4-(1-(3,5-dichlorophenylthio)-4-(dimethylamino)butan-2-ylamino)-3-(trifluoromethylsulfonyl)benzenesulfonamide | 259 |
| 42 | N-(7-(1-1-(4'-chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide | 97 |
| 43 | (R)-N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide | 2419 |
| 44 | N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl)benzenesulfonamide | 235 |
| 45 | N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl)benzenesulfonamide | 365 |
| 46 | (R)-N-(7-(1-(2-(but-2-ynyloxy)benzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide, trifluoroacetate salt | 1770 |
| 47 | N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(2-fluoro-phenylsulfanylmethyl)-propylamino]-3-trifluoromethanesulfonyl-benzenesulfonamide | 25 |
| 48 | N-{(S)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3 trifluoromethanesulfonyl-benzene sulfonamide | 353 |
| 49 | N-{(R)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzene sulfonamide | 33 |
| 50 | (R)-N-(2-chloro-7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 31 |
| 51 | N-(7-(1-1-(4'-chlorobiphenyl-2-yl)ethyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide | 35 |
| 52 | N-(7-(1((4'-chlorobiphenyl-2-yl)methyl)piperidin-4-yl)-5,6,7,8-tetrahydropyrido[3,4-d]pyrimidin-4-yl)-4-(2-(phenylthio)ethylamino)-3-(trifluoromethylsulfonyl) benzenesulfonamide | 1307 |
| 53 | (R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 66 |
| 54 | (R)-N-(7-(1-((4'-chlorobiphenyl-2-yl)methyl)piperidin-4-yl)-5,6,7,8-tetrahydropyrido[3,4-d]pyrimidin-4-yl)-3-cyano-4-(4-(dimethylamino)-1-(phenylthio)butan-2-ylamino) benzenesulfonamide | 173 |
| 55 | (R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide | 35 |
| 56 | (R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide | 27 |
| 57 | N-{7-[1-(4'-Fluoro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonyl-benzenesulfonamide | 99 |
| 58 | (R)-N-(7-(1-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-nitrobenzenesulfonamide | 66 |
| 59 | N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide | 579 |
| 60 | (R)-N-(7-(4-((4'-chlorobiphenyl-2-yl)methyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 63 |
| 61 | (R)-N-(7-(4-(2-bromobenzyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 306 |
| 62 | N-(7-(4-((4'-chlorobiphenyl-2-yl)methylene)cyclohexyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide | 174 |
| 63 | N-(7-(4-benzylidenecyclohexyl)-5,6,7,8-tetrahydropyrido[3,4-d]pyrimidin-4-yl)-4-((R)-4-(dimethylamino)-1-(phenylthio)butan-2-ylamino)-3 trifluoromethylsulfonyl)benzenesulfonamide | 1184 |
| 64 | (R)-N-(7-(4-((4'-chlorobiphenyl-2-yl)methyl)-4-hydroxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 70 |

TABLE 4-continued

| Example | Name | Bcl-2 Biacore IC$_{50}$ (nM) |
|---|---|---|
| 65 | N-(7-(1-((4'-Chlorobiphenyl-2-yl)methyl)-3-fluoropiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide | 181 |
| 66 | N-(7-(1-((4'-chlorobiphenyl-2-yl)methyl)-3-fluoropiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide | 36 |
| 67 | (R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 42 |
| 68 | (R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide | 235 |
| 69 | N-(7-(1-((4'-chlorobiphenyl-2-yl)methyl)-3-fluoropiperidin-4-yl)-2-(trifluoromethyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide | 47 |
| 70 | (R)-N-(7-(1-((2-(4-chlorophenyl)-5,5-dimethylcyclohex-1-enyl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 51 |
| 71 | (R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-nitrobenzenesulfonamide | 20 |
| 72 | (R)-N-(6-(1-((4'-chlorobiphenyl-2-yl)methyl)piperidin-4-yl)-6,7-dihydro-5H-pyrrolo[3,4-d]pyrimidin-4-yl)-4-(4-morpholino-1-(phenylthio)butan-2-ylamino)-3-(trifluoromethylsulfonyl)benzenesulfonamide | 971 |
| 73 | (R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide | 26 |
| 74 | N-(7-(1-((S)-1-(4'-chlorobiphenyl-2-yl)ethyl)-4-deuteropiperidin-4-yl)-2-(trifluoromethyl)-5,6,7,8-tetrahydropyrido[3,4-d]pyrimidin-4-yl)-4-((R)-1-(2-fluorophenylthio)-4-(4-methylpiperazin-1-yl)butan-2-ylamino)-3-(trifluoromethylsulfonyl)benzenesulfonamide | 41 |
| 75 | (R)-N-(7-(1-((2-(4-chlorophenyl)-4,4-dimethylcyclohex-1-enyl)methyl)-4-deuteropiperidin-4-yl)-2-(dimethylamino)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide | 66 |
| 76 | (R)-N-(7-(4-((4'-chlorobiphenyl-2-yl)methyl)-4-methoxy-1-dueterocyclohexyl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide | N/A |
| 77 | 4-((R)-1-Benzyloxymethyl-3-dimethylamino-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide | N/A |
| 78 | N-(7-{1-[2-(4-Chloro-phenyl)-4,4-dimethyl-cyclohex-1-enylmethyl]-4-deutero-piperidin-4-yl}-5,6,7,8-tetrahydro-pyrido[3,4-d]pyrimidin-4-yl)-4-[(R)-3-(isopropyl-methyl-amino)-1-phenylsulfanylmethyl-propylamino]-3-trifluoromethanesulfonyl-benzenesulfonamide | 41 |
| 79 | 4-((R)-3-Amino-1-phenylsulfanylmethyl-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide | 84 |
| 80 | 4-((2R)-4-(8-oxa-3-azabicyclo[3.2.1]octan-3-yl)-1-(phenylthio)butan-2-ylamino)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-3-(trifluoromethylsulfonyl)benzenesulfonamide | 225 |
| 81 | 4-((2R)-4-(8-oxa-3-azabicyclo[3.2.1]octan-3-yl)-1-(phenylthio)butan-2-ylamino)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-3-(trifluoromethylsulfonyl)benzenesulfonamide | 312 |
| 82 | (R)-N-(7-(1-((4'-chloro-4-fluorobiphenyl-2-yl)methyl)-4-dueteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide | 109 |
| 83 | (R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide | 28 |
| 84 | N-{7-[4-Deutero-1-(4'-chloro-4-fluoro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide | 73 |
| 85 | (R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide | 30 |
| 86 | N-(7-{1-[(R)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide | 46 |
| 87 | (R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide | 32 |
| 88 | N-(7-{1-[(S)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide | 2308 |
| 89 | (R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(4-ethylpiperazin-1-yl)-1-(phenylthio)butan-2-ylamino)-3-(trifluoromethylsulfonyl)benzenesulfonamide | 35 |
| 90 | N-(7-(1-(1-((2-(4-chlorophenyl)-4,4-dimethylcyclohex-1-enyl)ethyl) 4-deuteropiperidin-4-yl)-5,6,7,8-tetrahydropyrido[3,4-d]pyrimidin-4-yl)-4-((R)-4-D-morpholino-1-(phenylthio)butan-2-ylamino)-3-(trifluoromethylsulfonyl)benzenesulfonamide | 149 |
| 91 | (R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide | 41 |
| 92 | N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-morpholin-4-yl-1-phenylsulfanylmethyl-propylamino)-3- | 194 |

TABLE 4-continued

| Example | Name | Bcl-2 Biacore IC$_{50}$ (nM) |
|---|---|---|
| 93 | N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-dimethylamino-1-phenyl-sulfanylmethyl-propylamino)-3-trifluoromethanesulfonyl-benzenesulfonamide | 24 |
| 94 | N-{7-[1-(4'-Chloro-biphenyl-2-ylmethyl)-piperidin-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide | 405 |
| 95 | N-{7-[1-(4'-Chloro-biphenyl-2-ylmethyl)-azepan-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide | 1900 |
| 96 | N-{7-[1-(4'-Chloro-biphenyl-2-ylmethyl)-2-methyl-piperidin-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide, trifluoroacetate salt | 144 |
| 97 | N-{7-[1-(3'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide | 49 |
| 98 | N-(7-(1-((2'-chlorobiphenyl-2-yl)methyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide | 36 |
| 99 | (R)-4-(4-(dimethylamino)-1-(phenylthio)butan-2-ylamino)-N-(7-(1-((4'-(trifluoromethyl)biphenyl-2-yl)methyl)piperidin-4-yl)-5,6,7,8-tetrahydropyrido[3,4-d]pyrimidin-4-yl)-3-(trifluoromethylsulfonyl)benzenesulfonamide | 37 |

What is claimed is:

1. A compound of formula (Ib):

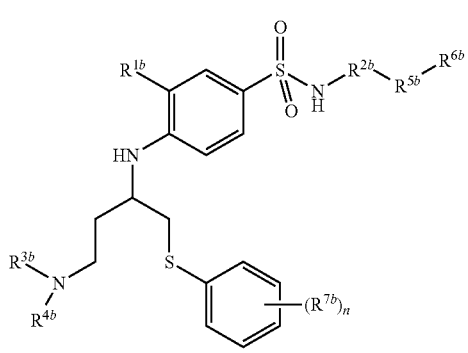

(Ib)

wherein

R$^{1b}$ is H, NO$_2$, SO$_2$CF$_3$, SO$_2$(C$_1$-C$_6$)alkyl, halo-substituted (C$_1$-C$_6$)alkyl, halogen, (C$_3$-C$_{14}$)cycloalkyl, or CN;

R$^{2b}$ is a divalent bicyclic radical selected from:

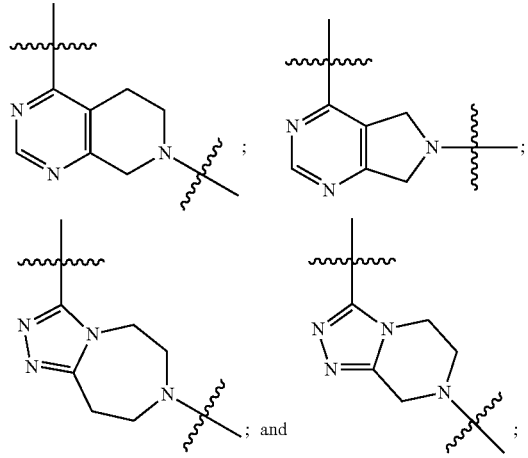

wherein R$^{2b}$ may unsubstituted or substituted with one or more of halogen, OH, (C$_1$-C$_6$)alkyl, halo-substituted (C$_1$-C$_6$)alkyl, CN or NH$_2$;

R$^{3b}$ and R$^{4b}$ are independently selected from hydrogen, methyl and isopropyl; or R$^{3b}$ and R$^{4b}$ together form a group selected from morpholino; piperidinyl, pyrrolidinyl, 8-oxa-3-azabicyclo[3.2.1]octan-3-yl and piperazinyl substituted with a group selected from methyl and ethyl;

R$^{5b}$ is selected from:

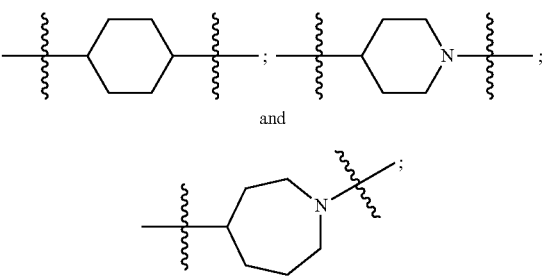

which is unsubstituted or substituted with (C$_1$-C$_6$)alkyl, halogen, OH, (C$_1$-C$_3$)alkoxy, NH$_2$, or deuterium;

R$^{6b}$ is L$_b$-R$^{8b}$;

R$^{7b}$ is halogen;

L$_b$ is selected from methylene, =CH— and —CH(CH$_3$)— wherein L$_b$ is unsubstituted or substituted by one or more (C$_1$-C$_4$)alkyl, halo-substituted(C$_1$-C$_4$)alkyl, or (C$_3$-C$_8$)cycloalkyl;

R$^{8b}$ is selected from phenyl, biphenyl, 4,4-dimethyl-2,3,4,5-tetrahydro-1,1'-biphenyl and 3,3-dimethyl-2,3,4,5-tetrahydro-1,1'-biphenyl; each of which is unsubstituted or substituted with one or more substituents each independently selected from halogen, methoxy, OH, (C$_1$-C$_6$) alkyl, halo-substituted(C$_1$-C$_6$)alkyl, or CN; and n is 0, 1, 2, 3, or 4;

or a pharmaceutically acceptable salt thereof.

2. A method of treating chronic lymphocytic leukemia comprising the step of administering to a subject in need thereof (i) a therapeutically effective amount of a compound of claim 1, or a pharmaceutically acceptable salt thereof, or (ii) a pharmaceutical composition comprising a compound of claim 1, or a pharmaceutically acceptable salt thereof, and at least one pharmaceutically acceptable excipient.

3. A pharmaceutical composition comprising a compound of formula I according to claim 1, or a pharmaceutically acceptable salt thereof, and a pharmaceutically acceptable carrier or excipient.

4. A compound, or pharmaceutically acceptable salt thereof, selected from:

N-{7-[1-(4'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-nitro-benzenesulfonamide;

(R)-N-(7-(1-((2-(4-chlorophenyl)-5,5-dimethyl-cyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

N-(7-((2S)-1((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-nitrobenzene-sulfonamide;

N-(7-((2S)-1-(4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethyl-sulfonyl)benzenesulfonamide, trifluoroacetate salt;

(R)-4-(4-(dimethylamino)-1-(phenylthio)butan-2-ylamino)-N-(7-(1-((4'-fluorobiphenyl-2-yl)methyl)piperidin-4-yl)-5,6,7,8-tetrahydropyrido[3,4-d]pyrimidin-4-yl)-3-(trifluoromethylsulfonyl)benzenesulfonamide;

(R)-N-(7-(1-((4'-bromobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-(2-bromobenzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-{7-[2-(4-Chloro-phenyl)-5,5-dimethyl-cyclohex-1-enylmethyl]-5,6,7,8-tetrahydro-pyrido[3,4-d]pyrimidin-4-yl}-4-((R)-3-morpholin-4-yl-1-phenylsulfanylmethyl-propylamino)-3-trifluoromethanesulfonylbenzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

(R)-N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3,5-difluorobenzenesulfonamide;

N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide;

N-(4-(N-(7-(1-((4'-chloro-4-fluorobiphenyl-2-yl)methyl)piperidin-4-yl)-5,6,7,8-tetrahydropyrido[3,4-d]pyrimidin-4-yl)sulfamoyl)-2-(trifluoromethylsulfonyl)phenyl)-N-(2-(phenylthio)ethyl)acetamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide;

(R)-N-(7-(1-((4'-chloro-5-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chloro-4-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chloro-3-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-3-(4-(N-(7-(1-((4'-chlorobiphenyl-2-yl)methyl)piperidin-4-yl)-5,6,7,8-tetrahydropyrido[3,4-d]pyrimidin-4-yl)sulfamoyl)-2-nitrophenylamino)-N,N-dimethyl-4-(phenylthio)butanamide;

N-{7-[1-(4'-Chloro-biphenyl-2-ylmethyl)-piperidin-4-yl]-5,6,7,8-tetrahydro-pyrido[3,4-d]pyrimidin-4-yl}-4[(R)-3-(4-ethyl-piperazin-1-yl)-1-phenylsulfanylmethyl-propylamino]-3-trifluoromethanesulfonylbenzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

4-((R)-1-Benzyloxymethyl-3-dimethylamino-propylamino)-N-{7-[1-(4'-chloro-biphenyl-2-ylmethyl)-piperidin-4-yl]-5,6,7,8-tetrahydro-pyrido[3,4-d]pyrimidin-4-yl}-3-trifluoromethanesulfonylbenzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonylbenzenesulfonamide;

N-(7-(1-((2-(4-chlorophenyl)-4,4-dimethylcyclohex-1-enyl)methyl)-2-methylpiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido

[3,4-d]pyrimidin-4-yl)-4-(1-(2-chlorophenylthio)-4-(dimethylamino)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-1-(2-chlorophenylthio)-4-(dimethylamino)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)-4-(piperidin-1-yl)butan-2-ylamino)-3-(trifluoromethylsulfonyl)benzenesulfonamide;

N-(7-(1-(1-(4'-chloro-4-fluorobiphenyl-2-yl)ethyl)piperidin-4-yl)-5,6,7,8-tetrahydropyrido [3,4-d]pyrimidin-4-yl)-4-((R)-4-morpholino-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

N-(7-(1-(1-(4'-chlorobiphenyl-2-yl)ethyl)piperidin-4-yl)-2-(trifluoromethyl)-5,6,7,8-tetrahydropyrido[3,4-d]pyrimidin-4-yl)-4-((R)-1-(2-chlorophenylthio)-4-(dimethylamino) butan-2-ylamino)-3-(trifluoromethylsulfonyl)benzenesulfonamide;

N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-(4-methylpip erazin-1-yl)-1-(phenylthio)butan-2-ylamino)-3-(trifluoromethylsulfonyl)benzenesulfonamide;

(R)-N-(7-(1-((4'-chloro-4-methoxybiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(4-fluoro-phenylsulfanylmethyl)-propylamino]-3-trifluoromethanesulfonyl-benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2,6-dichlorophenylthio)-4-(dimethylamino)butan-2-ylamino)-3-(trifluoromethylsulfonyl)benzenesulfonamide;

N-{7-[1-(4'-Chlorobiphenyl-2-ylmethyl)-piperidin-4-yl]-5,6,7,8-tetrahydro-pyrido[3,4-d]pyrimidin-4-yl}-4-[(R)-1-(3,4-dichloro-phenylsulfanylmethyl)-3-dimethylamino-propylamino]-3-trifluoromethanesulfonyl-benzene-sulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(3,5-dichlorophenylthio)-4-(dimethylamino)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl) benzenesulfonamide;

N-(7-(1((4'-chlorobiphenyl-2-yl)methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl) benzenesulfonamide;

N-(7-(1-((2-(4-chlorophenyl)-4,4-dimethylcyclohex-1-enyl)methyl)piperidin-4-yl)-5,6,7,8-tetrahydropyrido [3,4-d]pyrimidin-4-yl)-4-(1-(phenylthio)propan-2-ylamino)-3-(trifluoromethylsulfonyl) benzenesulfonamide;

(R)-N-(7-(1-(2-(but-2-ynyloxy)benzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide, trifluoroacetate salt;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(2-fluoro-phenylsulfanylmethyl)-propylamino]-3-trifluoromethanesulfonyl-benzenesulfonamide;

N-{(S)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3trifluoromethanesulfonyl-benzene sulfonamide;

N-{(R)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzene sulfonamide;

(R)-N-(2-chloro-7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

N-(7-(1-((4'-chlorobiphenyl-2-yl)methyl)piperidin-4-yl)-5,6,7,8-tetrahydropyrido[3,4-d]pyrimidin-4-yl)-4-(2-(phenylthio)ethylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-3-cyano-4-(4-(dimethylamino)-1-(phenylthio)butan-2-ylamino) benzenesulfonamide;

(R)-N-(7-(1-((2-(4-chlorophenyl)-4,4-dimethylcyclohex-1-enyl)methyl)piperidin-4-yl)-5,6,7,8-tetrahydropyrido [3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-{7-[1-(4'-Fluoro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonyl-benzenesulfonamide;

(R)-N-(7-(1-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-nitrobenzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide;

(R)-N-(7-(4-((4'-chlorobiphenyl-2-yl)methyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(4-(2-bromobenzyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(4-((4'-chlorobiphenyl-2-yl)methylene)cyclohexyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

N-(7-(4-benzylidenecyclohexyl)-5,6,7,8-tetrahydropyrido[3,4-d]pyrimidin-4-yl)-4-((R)-4-(dimethylamino)-1-(phenylthio)butan-2-ylamino)-3trifluoromethylsulfonyl) benzenesulfonamide;

(R)-N-(7-(4-((4'-chlorobiphenyl-2-yl)methyl)-4-hydroxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((4'-Chlorobiphenyl-2-yl)methyl)-3-fluoropiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

N-(7-(1-((4'-chlorobiphenyl-2-yl)methyl)-3-fluoropiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

N-(7-(1-((4'-chlorobiphenyl-2-yl)methyl)-3-fluoropiperidin-4-yl)-2-(trifluoromethyl)-5,6,7,8-tetrahydropyrido[3,4-d]pyrimidin-4-yl)-4((R)-4-(dimethylamino)-1-(phenylthio)butan-2-ylamino)-3-(trifluoromethylsulfonyl)benzenesulfonamide;

(R)-N-(7-(1-((2-(4-chlorophenyl)-5,5-dimethylcyclohex-1-enyl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

(R)-N-(6-(1-((4'-chlorobiphenyl-2-yl)methyl)piperidin-4-yl)-6,7-dihydro-5H-pyrrolo[3,4-d]pyrimidin-4-yl)-4-(4-morpholino-1-(phenylthio)butan-2-ylamino)-3-(trifluoromethylsulfonyl)benzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((S)-1-(4'-chlorobiphenyl-2-yl)ethyl)-4-deuteropiperidin-4-yl)-2-(trifluoromethyl)-5,6,7,8-tetrahydropyrido[3,4-d]pyrimidin-4-yl)-4-((R)-1-(2-fluorophenylthio)-4-(4-methylpiperazin-1-yl)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)-4-deuteropiperidin-4-yl)-2-(dimethylamino)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)-N-(7-(4-((4'-chlorobiphenyl-2-yl)methyl)-4-methoxy-1-dueterocyclohexyl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

4-((R)-1-Benzyloxymethyl-3-dimethylamino-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide;

N-(7-{1-[2-(4-Chloro-phenyl)-4,4-dimethyl-cyclohex-1-enylmethyl]-4-deutero-piperidin-4-yl}-5,6,7,8-tetrahydro-pyrido[3,4-d]pyrimidin-4-yl)-4-[(R)-3-(isopropyl-methyl-amino)-1-phenylsulfanylmethyl-propylamino]-3-trifluoromethanesulfonyl-benzenesulfonamide;

4-((R)-3-amino-1-phenylsulfanylmethyl-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide;

4-((2R)-4-(8-oxa-3-azabicyclo[3.2.1]octan-3-yl)-1-(phenylthio)butan-2-ylamino)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-3-(trifluoromethylsulfonyl)benzenesulfonamide;

4-((2R)-4-(8-oxa-3-azabicyclo[3.2.1]octan-3-yl)-1-(phenylthio)butan-2-ylamino)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-3-(trifluoromethylsulfonyl)benzenesulfonamide;

(R)-N-(7-(1-((4'-chloro-4-fluorobiphenyl-2-yl)methyl)-4-dueteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide;

(R)-N-(7-(1-((2-4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-{7-[4-Deutero-1-(4'-chloro-4-fluoro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide;

N-(7-{1-[(R)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-(7-{1-[(S)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide;

(R)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(4-ethylpiperazin-1-yl)-1-(phenylthio)butan-2-ylamino)-3-(trifluoromethylsulfonyl)benzenesulfonamide;

N-(7-(1-(1-(2-(4-chlorophenyl)-4,4-dimethylcyclohex-1-enyl)ethyl)4-deuteropiperidin-4-yl)-5,6,7,8-tetrahydropyrido[3,4-d]pyrimidin-4-yl)-4-((R)-4-D-morpholino-1-(phenylthio)butan-2-ylamino)-3-(trifluoromethylsulfonyl)benzenesulfonamide;

(R)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-morpholin-4-yl-1-phenylsulfanylmethyl-propylamino)-3-trifluoromethanesulfonyl-benzenesulfonamide;

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-dimethylamino-1-phenyl-sulfanylmethyl-propylamino)-3-trifluoromethanesulfonyl-benzenesulfonamide;

N-{7-[1-(4'-Chloro-biphenyl-2-ylmethyl)-piperidin-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide;

N-{7-[1-(4'-Chloro-biphenyl-2-ylmethyl)-azepan-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide;

N-{7-[1-(4'-Chloro-biphenyl-2-ylmethyl)-2-methyl-piperidin-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide, trifluoroacetate salt;

N-{7-[1-(3'-Chloro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide;

N-(7-(1-((2'-chlorobiphenyl-2-yl)methyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide; and (R)-4-(4-(dimethylamino)-1-(phenylthio)butan-2-ylamino)-N-(7-(1-((4'-(trifluoromethyl)biphenyl-2-yl)methyl)piperidin-4-yl)-5,6,7,8-tetrahydropyrido[3,4-d]pyrimidin-4-yl)-3-(trifluoromethylsulfonyl)benzenesulfonamide.

\* \* \* \* \*